US011485701B2

(12) United States Patent
Coats et al.

(10) Patent No.: US 11,485,701 B2
(45) Date of Patent: Nov. 1, 2022

(54) INSECT REPELLENT COMPOUNDS AND COMPOSITIONS, AND METHODS THEREOF

(71) Applicant: Iowa State University Research Foundation, Inc., Ames, IA (US)

(72) Inventors: Joel R. Coats, Ames, IA (US); Edmund J. Norris, Ames, IA (US); James Scott Klimavicz, Ames, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 0 days.

(21) Appl. No.: 15/684,770

(22) Filed: Aug. 23, 2017

(65) Prior Publication Data

US 2019/0047937 A1 Feb. 14, 2019

Related U.S. Application Data

(60) Provisional application No. 62/378,466, filed on Aug. 23, 2016.

(51) Int. Cl.

| | |
|---|---|
| C07C 69/75 | (2006.01) |
| A01N 37/06 | (2006.01) |
| A01N 37/08 | (2006.01) |
| A01N 37/10 | (2006.01) |
| A01N 43/16 | (2006.01) |
| C07D 311/16 | (2006.01) |
| C07D 333/24 | (2006.01) |
| C07D 307/68 | (2006.01) |
| C07D 333/38 | (2006.01) |
| A01N 43/30 | (2006.01) |
| C07D 305/06 | (2006.01) |
| C07C 69/74 | (2006.01) |
| A01N 49/00 | (2006.01) |
| C07D 305/08 | (2006.01) |
| C07C 69/24 | (2006.01) |
| C07C 69/07 | (2006.01) |
| C07C 69/618 | (2006.01) |
| C07C 69/533 | (2006.01) |
| C07C 255/19 | (2006.01) |
| C07C 69/63 | (2006.01) |
| C07C 69/587 | (2006.01) |
| A01N 37/02 | (2006.01) |
| A01N 43/08 | (2006.01) |
| A01N 43/10 | (2006.01) |
| A01N 53/00 | (2006.01) |
| C07C 67/08 | (2006.01) |
| C07C 69/04 | (2006.01) |
| C07C 69/22 | (2006.01) |
| C07C 69/612 | (2006.01) |
| C07C 69/635 | (2006.01) |
| C07C 69/757 | (2006.01) |
| C07C 69/76 | (2006.01) |

(Continued)

(52) U.S. Cl.
CPC .............. *C07C 69/75* (2013.01); *A01N 37/02* (2013.01); *A01N 37/06* (2013.01); *A01N 37/08* (2013.01); *A01N 37/10* (2013.01); *A01N 43/08* (2013.01); *A01N 43/10* (2013.01); *A01N 43/16* (2013.01); *A01N 43/30* (2013.01); *A01N 49/00* (2013.01); *A01N 53/00* (2013.01); *C07C 67/08* (2013.01); *C07C 69/04* (2013.01); *C07C 69/07* (2013.01); *C07C 69/22* (2013.01); *C07C 69/24* (2013.01); *C07C 69/533* (2013.01); *C07C 69/587* (2013.01); *C07C 69/612* (2013.01); *C07C 69/618* (2013.01); *C07C 69/63* (2013.01); *C07C 69/635* (2013.01); *C07C 69/74* (2013.01); *C07C 69/757* (2013.01); *C07C 69/76* (2013.01); *C07C 205/43* (2013.01); *C07C 255/19* (2013.01); *C07D 305/06* (2013.01); *C07D 305/08* (2013.01); *C07D 307/68* (2013.01); *C07D 311/16* (2013.01); *C07D 333/24* (2013.01); *C07D 333/38* (2013.01); *C07D 333/40* (2013.01); *C07C 2601/02* (2017.05); *C07C 2601/04* (2017.05); *C07C 2601/08* (2017.05); *C07C 2601/14* (2017.05); *C07C 2601/16* (2017.05); *C07C 2602/42* (2017.05)

(58) Field of Classification Search
None
See application file for complete search history.

(56) References Cited

U.S. PATENT DOCUMENTS 3,493,650 A * 2/1970 Dunkel .................. A61Q 15/00
424/65
3,673,237 A 6/1972 Janiak
(Continued)

FOREIGN PATENT DOCUMENTS

JP 2004-123985 4/2004
WO 2000/21364 A2 4/2000
(Continued)

OTHER PUBLICATIONS

Modak et al. Chem. Commun., 49, 252-254, 253 (2013) (Year: 2013).*

(Continued)

*Primary Examiner* — Samantha L Shterengarts
(74) *Attorney, Agent, or Firm* — Troutman Pepper Sanders Hamilton LLP (Rochester)

(57) ABSTRACT

The present invention relates to monoterpenoid and phenylpropanoid containing derivative compounds, methods of making the compounds, compositions comprising the compounds, and methods of repelling pests using the compounds and/or compositions.

9 Claims, 8 Drawing Sheets

(51) Int. Cl.
  C07C 205/43    (2006.01)
  C07D 333/40    (2006.01)

(56) References Cited

U.S. PATENT DOCUMENTS

| | | | |
|---|---|---|---|
| 4,735,358 A | 4/1988 | Morita et al. | |
| 4,882,873 A | 11/1989 | Purnell | |
| 5,662,914 A | 9/1997 | Shorey et al. | |
| 5,750,129 A | 5/1998 | Wakarchuk | |
| 6,337,071 B1 | 1/2002 | Molyneux | |
| 6,524,605 B1 | 2/2003 | Coats et al. | |
| 7,524,888 B2 | 4/2009 | Coats et al. | |
| 7,939,091 B2 | 5/2011 | Coats et al. | |
| 8,207,157 B2 | 6/2012 | Bernier et al. | |
| 8,642,663 B2* | 2/2014 | Bencsits | A01N 49/00 514/722 |
| 9,340,757 B2* | 5/2016 | Cunningham | C11B 9/0038 |
| 9,399,030 B2* | 7/2016 | Sagawa | A61K 31/22 |
| 2003/0138471 A1 | 7/2003 | Coats et al. | |
| 2003/0185867 A1* | 10/2003 | Kerschner | A61K 8/342 424/401 |
| 2004/0103388 A1 | 5/2004 | Aleshin et al. | |
| 2007/0154504 A1 | 7/2007 | Coats et al. | |
| 2012/0082628 A1* | 4/2012 | Haught | A61K 8/37 424/51 |
| 2016/0122271 A1* | 5/2016 | Indradas | C07C 43/166 510/102 |

FOREIGN PATENT DOCUMENTS

| | | |
|---|---|---|
| WO | 2008/043183 | 4/2008 |
| WO | 2010/115065 A2 | 10/2010 |
| WO | 2012/001668 A1 | 1/2012 |
| WO | 2016/190227 A1 | 12/2016 |

OTHER PUBLICATIONS

Ortar, Giorgio. Modulation of thermos-transient receptor potential (thermos-TRP) channels by thymol-based compounds. Bioorganic & Medicinal Chemistry Letters. 22 (2012), 3535-3539.*
Komsta, Zofia. Diastereoselective Synthesis of Tetrahydrofurans from Aryl 3-Chloropropylsulfoxides and Aldehydes. J. Org. Chem. 75(10), 2010, 3251-3259, Supplemental Data S1-S105.*
Database Registry Chemical Abstracts Service, Columbus, Ohio, Accession No. RN 37139-89-2. Entered STN: Nov. 16, 1984.*
Database Registry Chemical Abstracts Service, Columbus, Ohio, Accession No. RN 545446-55-7. Entered STN: Jul. 10, 2003.*
Tokuoka, Yoshikazu. Enhancement in Skin Permeation of 5-Aminolevulinic Acid Using ¬¬|¬-Menthol and its Derivatives. Drug Development and Industrial Pharmacy. 34: 595-601, 2008.*
Park & Coats, "Cyanogenic Glycosides: Alternative Insecticides?," The Korean Journal of Pesticide Science 6(2):51-57 (2002).
Gereszek et al.,"Effects of Dietary Conjugated Linoleic Acid on European Corn Borer (Lepidoptera: Crambidae) Survival, Fatty Acid Profile, and Fecundity," Physiology, Biochemistry, and Toxicology 101(2):430-438 (2008).
Paluch et al., "Quantitative Structure—Activity Relationship of Botanical Sesquiterpenes: Spatial and Contact Repellency to the Yellow Fever Mosquito, Aedes aegypti," J. Agric. Food Chem. 57:7618-7625 (2009).
Paluch et al., "Mosquito Repellents: A Review of Chemical Structure Diversity and Olfaction," Pest Manag. Sci. 66:925-935 (2010).
Seiber et al., "Biopesticides: State of the Art and Future Opportunities," J. Agric. Food Chem. 62:11613-11619 (2014).
Tong & Coats, "Effects of Monoterpenoid Insecticides on [3H]-TBOB Binding in House Fly GABA Receptor and 36Cl—Uptake in American Cockroach Ventral Nerve Cord," Pestcide Biochemistry and Physiology 98:317-324 (2010).
Tong & Coats, "Quantitative Structure-Activity Relationships of Monoterpenoid Binding Activities to the Housefly GABA Receptor," Pest Manag. Sci. 68:1122-1129 (2012).
Binning et al., "Susceptibility to Bt Proteins is Not Required For Agrotis Ipsilon Aversion to Bt Maize," Pest Manag. Sci. 71:601-606 (2015).
Gross et al., "Pharmacological Characterization of a Tyramine Receptor From The Southern Cattle Tick, Rhipicephalus (Boophilus) Microplus," Insect Biochemistry and Molecular Biology 63:47-53 (2015).
Anderson & Coats, "Acetylcholinesterase Inhibition by Nootkatone and Carvacrol in Arthropods," Pesticide Biochemistry and Physiology 102:124-128 (2012).
Tsao et al., "Monoterpenoids and Their Synthetic Derivatives as Leads for New Insect-Control Agents," Synthesis and Chemistry of Agrochemicals IV 28:312-324 (1995).
Sfara et al., "Fumigant Insecticidal Activity and Repellent Effect of Five Essential Oils and Seven Monoterpenes on First-Instar Nymphs of Rhodnius Prolixus," Journal of Medical Entomology, 46(3):511-515 (2009).
Liu et al., "Identification of Repellent and Insecticidal Constituents of the Essential Oil of Artemisia rupestris L. Aerial Parts Against Liposcelis Bostrychophila Badonnel," Molecules, 18:10733-10746 (2013).
Chen et al., "Screening Tests of Esters of Chrysanthemumic Acid as Synergists and Insecticides," United States Department of Agriculture, Agricultrual Research Service, Entomol Research Branch ARS-33-23:1-10 (1956).
Moureu et al., "Derivatives of Cyclopentaneacetic Acid," Bulletin De Chimique De France 475-479 (1949).
Rice et al., "Structural Requirements for Monoterpenoid Activity Against Insects," American Chemical Society 557:92-108 (1994).
Grodnitzky et al., "Using Classic and Quantum Parameters to Determine Monoterpenoids' Insecticidal Quantitative Structure-Activity Relationships," American Chemical Society 800:238-250 (2001).
Angeles-Lopez et al, "Antinociceptive Effect of Extracts and Compounds From Hofmeisteria Schaffneri," Journal of Ethnopharmacology 131(2):425-432 (2010).
Xu et al., "Thymyl Esters Derivatives and a New Natural Product Modhephanone from Pulicaria Mauritanica Coss. (Asteraceae) Root Oil" Flavour and Fragrance Journal 30(1):83-90 (2015).
International Search Report dated Jan. 19, 2018 for PCT/US2017/048259.
First Examination Report (dated Oct. 28, 2020)—India Patent Application 201947006976.
Norris et al., "Comparison of the Insecticidal Characteristics of Commercially Available Plant Essential Oils Against Aedes aegypti and Anopheles gambiae (Diptera: Culicidae)," J. Med. Entomol. 52(5):993-1002 (2015).
International Preliminary Report on Patentability for PCT/US2017/048259 (dated Feb. 26, 2019).
Invitation to Pay Additional Fees Issued in PCT/US2017/048259 (dated Nov. 27, 2017).
Hearing Notice in India Patent Application 201947006976 (dated Jul. 9, 2021).
Informal Translation of the Office Action in Brazil Application BR112019003054-9 (dated Nov. 9, 2021).
Carroll et al., "Elemol and Amyris Oil Repel the Ticks Ixodes scapularis and Amblyomma americanum (Acari: Ixodidae) in Laboratory Bioassays," Exp. Appl. Acarol. 51:383-392 (2010).
Paluch et al., "Influence of Elm Foliar Chemistry on the Host Suitability of the Japanese Beetle, Popillia japonica, and the Gypsy Moth, Lymantria dispar," J. Agric. Urban Entomol. 23(4):209-223 (2006).
Zhu et al., "Adult Repellency and Larvicidal Activity of Five Plant Essential Oils Against Mosquitoes," Journal of the American Mosquito Control Association 22(3):515-522 (2006).
Park et al., "Mode of Action of Cyanohydrins in Insects," J. Pestic. Sci. 30(2): 99-102 (2005).
Schultz et al., "Catnip, Nepeta cataria (Lamiales: Lamiaceae)—a Closer Look: Seasonal Occurrence of Nepetalactone Isomers and Comparative Repellency of Three Terpenoids to Insects," Environ. Entomol. 33(6):1562-1569 (2004).

(56) References Cited

OTHER PUBLICATIONS

Park et al., "Fumigation Toxicity of Volatile Natural and Synthetic Cyanohydrins to Stored-Product Pests and Activity as Soil Fumigants," Pest Manag. Sci. 60:833-838 (2004).
Lee et al., "Fumigation Toxicity of Monoterpenoids to Several Stored Product Insects," J. Stored Prod. Res. 39:77-85 (2003).
Park et al., "QSAR Evaluation of Cyanohydrins' Fumigation Toxicity to House Fly (*Musca domestica*) and Lesser Grain Borer (*Rhyzopertha dominica*)," J. Agric. Food Chem. 50:5617-5620 (2002).
Grodnitzky et al., "QSAR Evaluation of Monoterpenoids' Insecticidal Activity," J. Agric. Food Chem. 50:4576-4580 (2002).
Park et al., "Cyanogenic Glycosides: Alternative Insecticides?," The Korean Journal of Pesticide Science 6(2):51-57 (2002).
Fassbinder et al., "Monoterpenoids as Possible Control Agents for Varroa Destructor," Journal of Apicultural Research 41(3-4):83-88 (2002).
Peterson et al., "Behavioral Activity of Catnip (Lamiaceae) Essential Oil Components to the German Cockroach (Blattodea: Blattellidae)," J. Econ. Entomol. 95(2):377-380 (2002).
Tsao et al., "Glucosinolate Breakdown Products as Insect Fumigants and Their Effect on Carbon Dioxide Emission of Insects," BMC Ecology 2(5):1-7 (2002).
Peterson et al., "Identification of Components of Osage Orange Fruit (*Maclura pomifera*) and Their Repellency to German Cockroaches," J. Essent. Oil Res. 14:233-236 (2002).
Tsao et al., "Plant Growth Regulatory Effect and Insecticidal Activity of the Extracts of the Tree of Heaven (*Ailanthus altissima* L.)," BMC Ecology 2(1):1-6 (2002).
Peterson et al., "Effects of Two Isoflavanoids, Osajin and Pomiferin, From Maclura Pomifera for Growth and Feeding Disruption in Ostrinia Nubilalis," J. Pesticide Sci. 26:261-265 (2001).
Peterson et al., "Osajin and Pomiferin, Two Isoflavones Purified From Osage Orange Fruits, Tested for Repellency to the Maize Weevil (Coleoptera: Curculionidae)," Environ. Entomol. 29(6):1133-1137 (2000).
Peterson et al., "Insecticidal Components in the Meal of Crambe Abyssinica," J. Agric. Urban Entomol. 17(1):27-35 (2000).
Peterson et al., "Insecticidal Activity of Cyanohydrin and Monoterpenoid Compounds," Molecules 5:648-654 (2000).
Carr et al., "The Interaction of Chlorinated Alicyclic Insecticides with Brain GABAA Receptors in Channel Catfish (*Ictalurus punctatus*)," Journal of Toxicology and Environmental Health, Part A 56:543-553 (1999).
Lee et al., "Influence of Dietary Applied Monoterpenoids and Derivatives on Survival and Growth of the European Corn Borer (Lepidoptera: Pyralidae)," J. Econ. Entomol. 92(1):56-67 (1999).
Peterson et al., "Glucosinolate Aglucones and Analogues: Insecticidal Properties and a QSAR," Pestic. Sci. 54:35-42 (1998).
Lee et al., "Insecticidal Activity of Monoterpenoids to Western Corn Rootworm (Coleoptera: Chrysomelidae), Twospotted Spider Mite (Acari: Tetranychidae), and House Fly (Diptera: Muscidae)," J. Econ. Entomol. 90(4):883-892 (1997).
Tsao et al., "Insecticidal Toxicities of Glucosinolate-Containing Extracts from Crambe Seeds," J. Agric. Entomol. 13(2):109-120 (1996).
Coats, J.R. "Risks from Natural Versus Synthetic Insecticides," Annu. Rev. Entomol. 39:489-515 (1994).
Rice et al., "Insecticidal Properties of Several Monoterpenoids to the House Fly (Diptera: Muscidae), Red Flour Beetle (Coleoptera: Tenebrionidae), and Southern Corn Rootworm (Coleoptera: Chrysomelidae)," J. Econ. Entomol. 87(5):1172-1179 (1994).
Karr et al., "Effects of Four Monoterpenoids on Growth and Reproduction in the German Cockroach (Blattodea: Blattellidae)," J. Econ. Entomol. 85(2):424-429 (1992).
Featherstone et al., "Noninvasive Detection of Electrical Events During the Startle Response in Larval Medaka," J. Exp. Biol. 158:583-589 (1991).
Coats J.R., "Mechanisms of Toxic Action and Structure-Activity Relationships for Organochlorine and Synthetic Pyrethroid Insecticides," Environ. Health Perspect. 87:255-262 (1990).
Karr et al., "Toxic Effects of d-Limonene in the Earthworm Eisenia Fetida (Savigny)," Pesticide Biochemistry and Physiology 36:175-186 (1990).
Karr et al., "Insecticidal Properties of d-Limonene," J. Pesticide Sci. 13:287-290 (1988).
Tong et al., "The Phenolic Monoterpenoid Carvacrol Inhibits the Binding of Nicotine to the Housefly Nicotinic Acetylcholine Receptor," Pest Manag. Sci. 69:775-780 (2013).
Zhu et al., "Mosquito Larvicidal Activity of Botanical-Based Mosquito Repellents," J. Am. Mosq. Contr. Assoc. 24:161-168 (2008).
Peterson et al., "Naturally Occurring Cyanohydrins, Analogues and Derivatives as Potential Insecticides," Pest. Manag. Sci. 56:615-617 (2000).
Klimavicz et al., "Monoterpenoid Derivatives as Biorational Mosquito Repellents," Poster Presentation, ACS AGRO 2016 Fall Meeting (Aug. 23, 2016).
Klimavicz et al., "Monoterpenoid Derivatives as Biorational Mosquito Repellents," Conference Abstract, ACS AGRO 2016 Fall Meeting (Mar. 21, 2016).
Examination Report (dated Aug. 12, 2022)—European Patent Application No. 17 761 713.1.
Sugeno et al., "Asymmetric Organocatalytic Cyclopropanation on Chiral Menthyl Acrylate for the Synthesis of (-)-trans-2-Aminomethylcyclopropanecarboxylic Acid [(-)-TAMP]," SYNLETT 25:0987-0990 (2014).
Baldwin et al., "Quantitative Analysis of Mixtures of 2-Deuterio-1-vinylcyclobutanes," J. Org. Chem. 74:7866-7872 (2009).
Takahashi et al., "FICA, A New Chiral Derivatizing Agent for Determining the Absolute Configuration of Secondary Alcohols by 19F and 1H NMR Spectroscopies," Tetrahedron: Asymmetry 24:1001-1009 (2013).

\* cited by examiner

INSECT REPELLENT COMPOUNDS AND COMPOSITIONS, AND METHODS THEREOF

This application claims the benefit of U.S. Provisional Patent Application Ser. No. 62/378,466, filed Aug. 23, 2016, which is hereby incorporated by reference in its entirety.

This invention was made with government support under USDA/NIFA grant numbers 2014-31100-06019, 2015-31100-06019, and 2016-31100-06019. The government has certain rights in this invention.

FIELD OF THE INVENTION

The present invention relates to insect repellent compounds, compositions containing the compounds, and methods of making and using the insect repellent compounds.

BACKGROUND OF THE INVENTION

Many plant essential oils contain monoterpene or monoterpenoid compounds, some of which are insect repellents. Their efficacy is often strong initially, but the protection time afforded by these monoterpenoids is relatively short, frequently ranging from 30 minutes to 2 hours. The short protection time, compared to the market leading compositions (e.g., DEET, picaridin, and IR3535) results in the lack of recommendation by the Centers for Disease Control and Prevention ("CDC") of the products that contain plant essential oils. The one exception is the CDC-approval of p-menthane-3,8-diol (from the oil of lemon eucalyptus) as a topical mosquito repellent. Since this compound is the only natural or biorational insect repellent approved by the CDC, it serves as a point-of-reference for efficacy of other biorational insect repellents.

For success in the marketplace, repellents based on monoterpenoid chemistry need either a slow-release device or formulation (adding expense), or a derivative of the parent monoterpenoid that will have lower volatility and a longer sustained bioactivity. Such derivative molecules have been designed to mimic the molecular weight and polarity of repellent sesquiterpenoids, which have been demonstrated to possess longer repellent character on a treated surface over time. Unfortunately, the use of these compounds as arthropod repellents is not often economically feasible, as isolating them from natural sources is costly and inefficient.

Therefore, there remains a need for a synthetically accessible and economically feasible monoterpenoid-based insect repellent that has a low volatility and a long sustained bioactivity. The present invention is directed to overcoming deficiencies in the art.

SUMMARY OF THE INVENTION

One aspect of the present invention relates to a compound of formula (A) as follows:

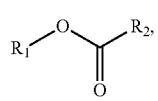

(A)

where $R_1$ is a monoterpenoid or phenylpropanoid moiety;

$R_2$ is substituted or unsubstituted and is selected from the group consisting of H, $C_1$-$C_7$ unbranched or branched alkyl, $C_2$-$C_7$ unbranched or branched alkenyl, $C_3$-$C_7$ unbranched or branched alkynyl, $C_3$-$C_7$ unbranched or branched cycloalkyl, aryl, heteroaryl, —$(CH_2)_n$-heteroaryl, and $C_3$-$C_7$ unbranched or branched cycloalkenyl; and n is an integer from 0-3, with the proviso that when $R_1$ is a monoterpenoid moiety $R_2$ is not a tert-butyl group.

Another aspect of the present invention relates to a compound of formula (B) as follows:

(B)

where $R_5$ is a monoterpenoid or phenylpropanoid moiety and $R_6$ is substituted or unsubstituted and is selected from the group consisting of $C_3$-$C_7$ unbranched or branched alkyl, $C_2$-$C_7$ unbranched or branched alkenyl, $C_3$-$C_7$ unbranched or branched alkynyl, $C_3$-$C_7$ unbranched or branched cycloalkyl, $C_3$-$C_7$ unbranched or branched cycloalkenyl, $C_3$-$C_7$ unbranched or branched heterocycle, $C_2$-$C_7$ saturated or unsaturated hydroxyalkyl, and —$(CR_{11}R_{12})_p$—O—$(CR_{11}R_{12})_q$—OH;

$R_{11}$ and $R_{12}$ are individually selected from H or $C_{1-6}$ alkyl;

p is an integer from 1 to 4; and q is an integer from 1 to 4, with the proviso that the compound is not selected from the group consisting of

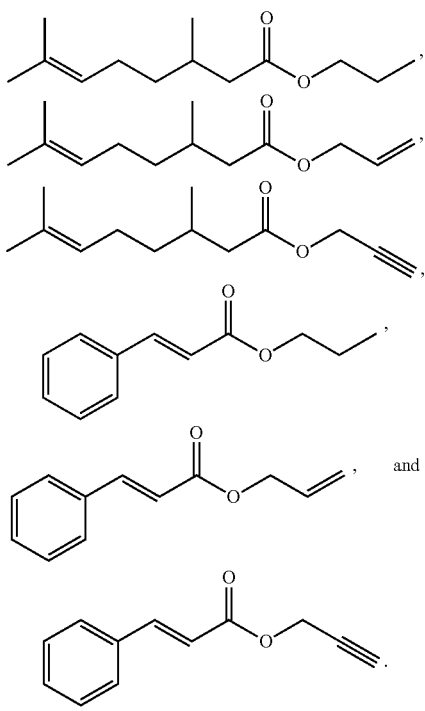

A further aspect of the present invention relates to a method of making a compound of formula (A) or formula (B). The method of making the compound of formula (A) involves reacting (I) R$_1$—OH with R$_2$—COOH;
(II) R$_1$—OH with

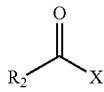

in the presence of a base; or
(III) R$_1$—OH with

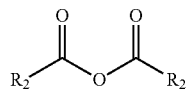

under conditions effective to form an ester having a structure of formula (A)

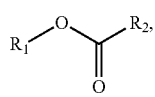
(A)

where
R$_1$ is a monoterpenoid or phenylpropanoid moiety;
R$_2$ is substituted or unsubstituted and is selected from the group consisting of H, C$_1$-C$_7$ unbranched or branched alkyl, C$_2$-C$_7$ unbranched or branched alkenyl, C$_3$-C$_7$ unbranched or branched alkynyl, C$_3$-C$_7$ unbranched or branched cycloalkyl, aryl, heteroaryl, —(CH$_2$)$_n$-heteroaryl, and C$_3$-C$_7$ unbranched or branched cycloalkenyl; and
n is an integer from 0-3; and
X is a halide.
The method of making a compound of formula (B) involves reacting:
(I) R$_5$—COOH with R$_6$—OH;
(II)

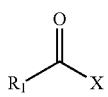

with R$_2$—OH in the presence of a base; or
(III)

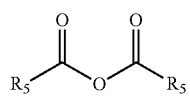

with R$_6$—OH;
under conditions effective to form an ester having a structure of Formula (B)

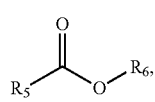
(B)

where
R$_5$ is a monoterpenoid or phenylpropanoid moiety and
R$_6$ is substituted or unsubstituted and is selected from the group consisting of C$_3$-C$_7$ unbranched or branched alkyl, C$_2$-C$_7$ unbranched or branched alkenyl, C$_3$-C$_7$ unbranched or branched alkynyl, C$_3$-C$_7$ unbranched or branched cycloalkyl, C$_3$-C$_7$ unbranched or branched cycloalkenyl, C$_3$-C$_7$ unbranched or branched heterocycle, C$_2$-C$_7$ saturated or unsaturated hydroxyalkyl, and —(CR$_{11}$R$_{12}$)$_p$—O—(CR$_{11}$R$_{12}$)$_q$—OH;
R$_{11}$ and R$_{12}$ are individually selected from H or C$_{1-6}$ alkyl;
p is an integer from 1 to 4;
q is an integer from 1 to 4; and
X is a halide.

A further aspect of the present invention relates to a composition comprising a compound of the present invention and a carrier.

Another aspect of the present invention relates to a method of repelling a pest. This method involves applying to a target area a composition comprising a compound of formula (A) or a compound of formula (B);
wherein, in the compound of formula (A),

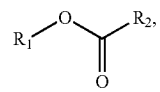
(A)

R$_1$ is a monoterpenoid or phenylpropanoid moiety;
R$_2$ is substituted or unsubstituted and is selected from the group consisting of H, C$_1$-C$_7$ unbranched or branched alkyl, C$_2$-C$_7$ unbranched or branched alkenyl, C$_3$-C$_7$ unbranched or branched alkynyl, C$_3$-C$_7$ unbranched or branched cycloalkyl, aryl, heteroaryl, —(CH$_2$)$_n$-heteroaryl, and C$_3$-C$_7$ unbranched or branched cycloalkenyl; and n is an integer from 0-3, with the proviso that when R$_1$ is a monoterpenoid moiety R$_2$ is not a tert-butyl group;
wherein, in the compound of formula (B),

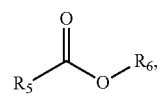
(B)

R$_5$ is a monoterpenoid or phenylpropanoid moiety;
R$_6$ is substituted or unsubstituted and is selected from the group consisting of C$_3$-C$_7$ unbranched or branched alkyl, C$_2$-C$_7$ unbranched or branched alkenyl, C$_3$-C$_7$ unbranched or branched alkynyl, C$_3$-C$_7$ unbranched or branched cycloalkyl, C$_3$-C$_7$ unbranched or branched cycloalkenyl, C$_3$-C$_7$ unbranched or branched heterocycle, C$_2$-C$_7$ saturated or unsaturated hydroxyalkyl, and —(CR$_{11}$R$_{12}$)$_p$—O—(CR$_{11}$R$_{12}$)$_q$—OH;
R$_{11}$ and R$_{12}$ are individually selected from H or C$_{1-6}$ alkyl;
p is an integer from 1 to 4; and
q is an integer from 1 to 4; and
wherein the applying is carried out under conditions effective to repel a pest.

To mimic the physicochemical properties of sesquiterpenoids by means of derivatizing readily available monoterpenoids, compounds were designed with the goal of reducing volatility, thus prolonging their repellent character on a treated surface. Another important property of the biorational synthetic repellents described herein is that they have suitable biological activity; specifically, strong insect repellent activity. Derivatives have been developed using the best-known repellent monoterpenoids, and esterifying them with groups that result in derivatives that mimic the physicochemical properties of active sesquiterpenoid repellents.

Each derivative was tested for its efficacy as a short-term repellent, allowing for the identification of molecules with significant repellent activity. Successful compounds were then tested to assess their potential long-term repellency. The novel compounds disclosed herein have exhibited both spatial repellency (repellency of the vapor phase) and contact irritancy (also called contact repellency).

Several novel monoterpenoid esters have been synthesized that demonstrate the efficacy and protection time of the best sesquiterpenoid insect repellents. The Examples (infra) demonstrate this bioactivity. Compounds of the present invention include single monoterpenoid derivatives or multiple monoterpenoid derivatives that have an increased molecular weight, higher polarity, and/or decreased volatility compared to currently available naturally/synthetically-derived monoterpenoid compounds that have been demonstrated to be potent spatial repellents for brief periods of time.

DETAILED DESCRIPTION OF THE INVENTION

Figure 1:
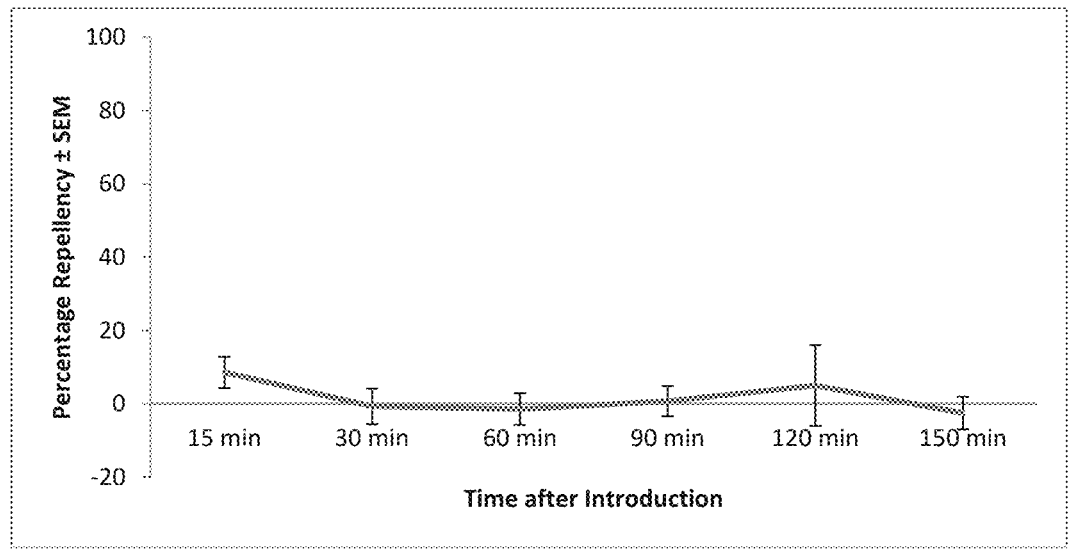
FIG. 1 is a graph showing the short-term percentage repellency of filter papers treated with 1 mL of acetone only at various time points. This figure demonstrates that the control treatment does not cause any significant repellency after the solvent is allowed to dry for 15 minutes before introduction into the chamber.

The present invention relates to compounds, including insect repellent compounds, compositions containing the compounds, and methods of making and using the compounds. In particular, the present invention relates to monoterpenoid and phenylpropanoid compounds derived from biorational sources for use against arthropods. As discussed in more detail infra, the monoterpenoid and phenylpropanoid derivative compounds of the present invention are particularly suited for use as repellents against various mosquito species.

In discussing the compounds (of formula (A) and formula (B), discussed infra) of the present invention, the following terms are provided for clarity.

As used herein, the term "monoterpenoid" refers to a monoterpene-like substance and may be used loosely herein to refer collectively to monoterpenoid derivatives as well as monoterpenoid analogs. By "monoterpene," is meant a compound having a 10-carbon skeleton with non-linear branches. A monoterpene technically refers to a compound with two isoprene units connected in a head-to-end manner. Monoterpenoids can therefore include monoterpenes, alcohols, ketones, aldehydes, esters, ethers, acids, hydrocarbons without an oxygen functional group, and so forth. It is common practice to refer to certain phenolic compounds, such as eugenol, thymol, and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein.

The term "phenylpropanoid" refers to a diverse group of organic compounds that are synthesized by plants from the amino acid phenylalanine. Their name is derived from the six-carbon, aromatic phenyl group and the three-carbon propene tail of cinnamic acid, which is synthesized from phenylalanine in the first step of phenylpropanoid biosynthesis. Phenylpropanoids are found throughout the plant kingdom, where they serve as essential components of a number of structural polymers, provide protection from ultraviolet light, defend against herbivores and pathogens, and mediate plant-pollinator interactions as floral pigments and scent compounds.

According to one embodiment, the monoterpenoid or phenylpropanoid of the compounds of the present invention is derived from a biorational source, such as a plant volatile or as a constituent of plant essential oils obtained from the leaf tissue, stem tissue, root tissue, or mixture thereof. In another embodiment, the monoterpenoid or phenylpropanoid used for synthesis to obtain a higher molecular weight, higher polarity, or decreased volatility is obtained from a synthetic source. The term "volatility" as used herein is defined as the property of a substance having a low boiling point and a high vapor pressure at ordinary temperatures and pressures. Similarly, the term "volatile" is considered to refer to a compound that is readily vaporizable at a relatively low temperature. A "slightly volatile" compound may be considered to have a vapor pressure of between about 0.05 Pascal (Pa) and two (2) Pa. Slightly volatile repellents can be considered to include DEET (vapor pressure of 0.22 Pa), as well as many of the repellent compounds of the present invention. "Slightly volatile" is a desirable property for a repellent because it provides an additional route of exposure against a target pest, i.e., fumigation, as discussed infra. Furthermore, the same amount of such a repellent is effective over a larger target area as compared with a non-volatile repellent, which is limited to only a contact route of exposure. "High volatility" is generally considered an undesirable property for a repellent, because such repellents typically dissipate too rapidly to be effective. Citronella is a repellent with high volatility. The essential oil of a plant is considered to include only "volatile" components. Similarly, the term "plant volatile" as used herein refers to a volatilizing compound from any part of a plant, including, but not limited to, a leaf, root, flower or flower bud, fruit, vegetable, stem, and so forth.

As used herein, the term "alkyl" means an aliphatic hydrocarbon group which may be straight or branched. When not otherwise restricted, the term refers to an alkyl of from 2 to 7 carbons. Exemplary alkyl groups include ethyl, n-propyl, i-propyl, n-butyl, t-butyl, n-pentyl, 3-pentyl, and the like.

The term "alkenyl" means an aliphatic hydrocarbon group containing a carbon-carbon double bond and which may be straight or branched having from 2 to about 7 carbon atoms in the chain. Exemplary alkenyl groups include ethenyl, propenyl, n-butenyl, isoprene, and i-butenyl. The term "alkenyl" may also refer to a hydrocarbon chain having 2 to 7 carbons containing at least one double bond and at least one triple bond.

The term "alkynyl" means an aliphatic hydrocarbon group containing a carbon-carbon triple bond and which may be straight or branched having about 3 to about 7 carbon atoms in the chain. Exemplary alkynyl groups include propynyl, n-butynyl, 2-butynyl, 3-methylbutynyl, propargyl, and n-pentynyl.

The term "cycloalkyl" means a non-aromatic, saturated or unsaturated, mono- or multi-cyclic ring system of about 3 to about 7 carbon atoms. Exemplary cycloalkyl groups include, without limitation, cyclopropyl, cyclobutyl, cyclopentyl, cyclohexyl, and cycloheptyl.

The term "aryl" means an aromatic monocyclic or multi-cyclic (polycyclic) ring system of 6 to about 19 carbon atoms, preferably of 6 to about 10 carbon atoms, and includes arylalkyl groups. The ring system of the aryl group may be optionally substituted. Representative aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "cycloalkenyl" means a non-aromatic, unsaturated, mono- or multi-cyclic ring system of about 3 to about 7 carbon atoms. Exemplary cycloalkenyl groups include, without limitation, cyclopropenyl, cyclobutenyl, cyclopentenyl, cyclohexenyl, and cycloheptenyl.

The term "hydroxyalkyl" refers to an alkyl group from 3 to 7 carbons in which one or more of the hydrogen atoms are replaced by a hydroxy group. Exemplary hydroxyalkyl groups include, without limitation, 2-hydroxyethyl, 3-hydroxypropyl, 2-hydroxypropyl, and 2,2-dihydroxyethyl. A hydroxyalkyl may be substituted or unsubstituted.

The term "heteroaryl" means an aromatic monocyclic or multi-cyclic ring system of about 5 to about 19 ring atoms, or about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl." Particular heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "halogen" as used herein is intended to include fluorine, bromine, chlorine, and iodine while the term "halide" is intended to include fluoride, bromide, chloride, and iodide anion.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halogen groups, perfluoroalkyl groups, perfluoroalkoxy groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, amino groups, alkyl- and dialkylamino groups, carbamoyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$C_6$ alkylthio groups, arylthio groups, nitro groups, boronate or boronyl groups, phosphate or phosphonyl groups, sulfamyl groups, sulfonyl groups, sulfinyl groups, and combinations thereof. In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art. In one embodiment, the compounds of the present invention are not substituted with

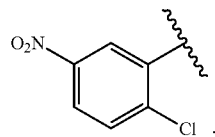 [SMILES: *c1cc([N+](=O)[O-])ccc1Cl]

According to one embodiment, the compounds of the present invention are unsubstituted. "Unsubstituted" atoms bear all of the hydrogen atoms dictated by their valency.

According to another embodiment, the compounds of the present invention are substituted. By "substituted" it is meant that a group may have a substituent at each substitutable atom of the group (including more than one substituent on a single atom), provided that the designated atom's normal valency is not exceeded and the identity of each substituent is independent of the others. For example, up to three H atoms in each residue are replaced with substituents such as halogen, haloalkyl, hydroxy, loweralkoxy, carboxy, carboalkoxy (also referred to as alkoxycarbonyl), carboxamido (also referred to as alkylaminocarbonyl), cyano, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. When a substituent is keto (i.e., =O), then two hydrogens on the atom are replaced. Combinations of substituents and/or variables are permissible only if such combinations result in stable compounds; by "stable compound" it is meant a compound that is sufficiently robust to survive isolation to a useful degree of purity from a reaction mixture, and formulation into an agent intended for a suitable use. In a particular embodiment of the compounds of the present invention, the compound is substituted (e.g., at $R_2$ (compounds of formula (A)) or $R_6$ (compounds of formula (B)) with one or more substituents selected from F, —Cl, —Br, —$NO_2$, —CN, —$N(CH_3)_2$, —$OCH_3$, —$OC_2H_5$, —$SCH_3$, —$SC_2H_5$, and other related chemistries.

The term "compound," and equivalent expressions, are meant to embrace compounds of formulae (A) and (B) as described herein. Also contemplated are salts, oxides, solvates, e.g., hydrates, and inclusion complexes of the compounds, where the context so permits, as well as any stereoisomeric form, or a mixture of any such forms of that compound in any ratio. Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

A first aspect of the present invention relates to a compound of formula (A) as follows:

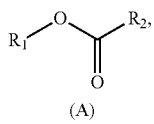

(A)

where
R₁ is a monoterpenoid or phenylpropanoid moiety;
R₂ is substituted or unsubstituted and is selected from the group consisting of H, $C_1$-$C_7$ unbranched or branched alkyl, $C_2$-$C_7$ unbranched or branched alkenyl, $C_3$-$C_7$ unbranched or branched alkynyl, $C_3$-$C_7$ unbranched or branched cycloalkyl, aryl, heteroaryl, —(CH₂)$_n$-heteroaryl, and $C_3$-$C_7$ unbranched or branched cycloalkenyl; and
n is an integer from 0-3, with the proviso that when R₁ is a monoterpenoid moiety R₂ is not a tert-butyl group.

In one embodiment, R₁ is a monoterpenoid moiety. Suitable monoterpenoid moieties include, without limitation,

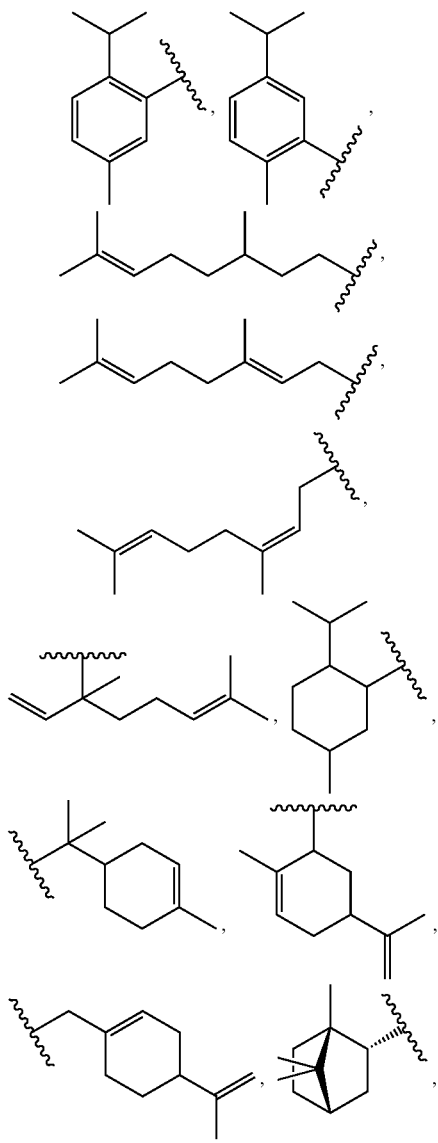

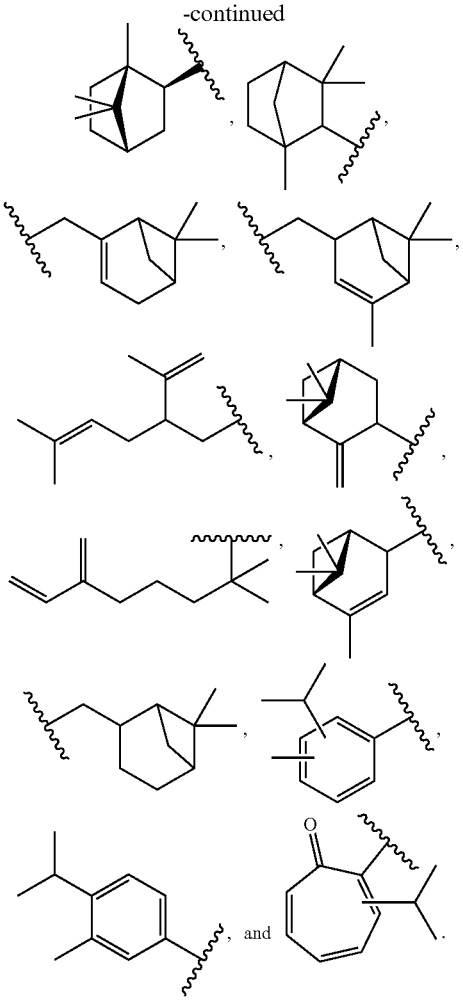

In another embodiment, R₁ is a phenylpropanoid moiety. Suitable phenylpropanoid moieties include, without limitation,

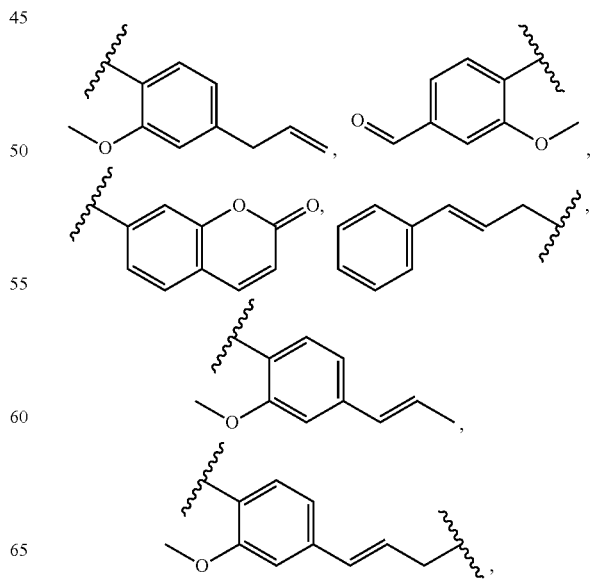

-continued

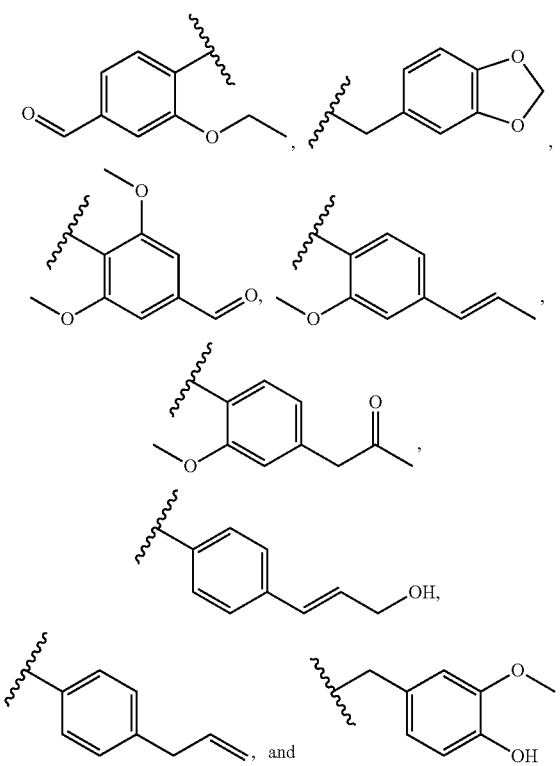

In one embodiment of the compound of formula (A), R$_2$ is H.

In another embodiment, R$_2$ is C$_3$-C$_7$ branched alkyl. Suitable C$_3$-C$_7$ branched alkyl groups include, without limitation,

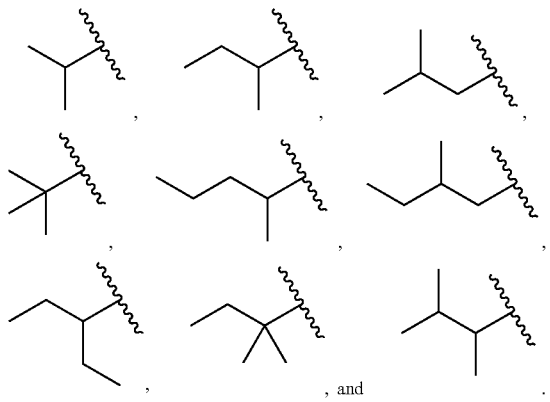

In another embodiment, R$_2$ is C$_2$-C$_7$ unbranched or branched alkenyl. Suitable C$_2$-C$_7$ unbranched or branched alkenyl groups include, without limitation,

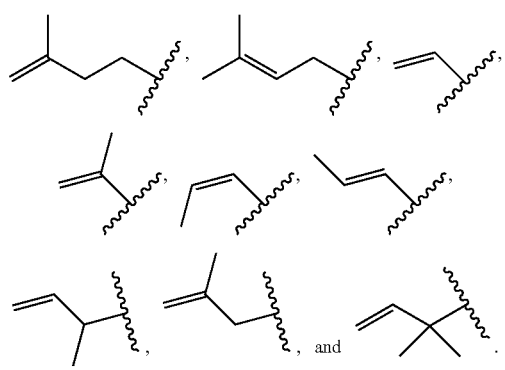

In another embodiment, R$_2$ is C$_3$-C$_7$ unbranched or branched alkynyl. Suitable C$_3$-C$_7$ unbranched or branched alkynyl groups include, without limitation,

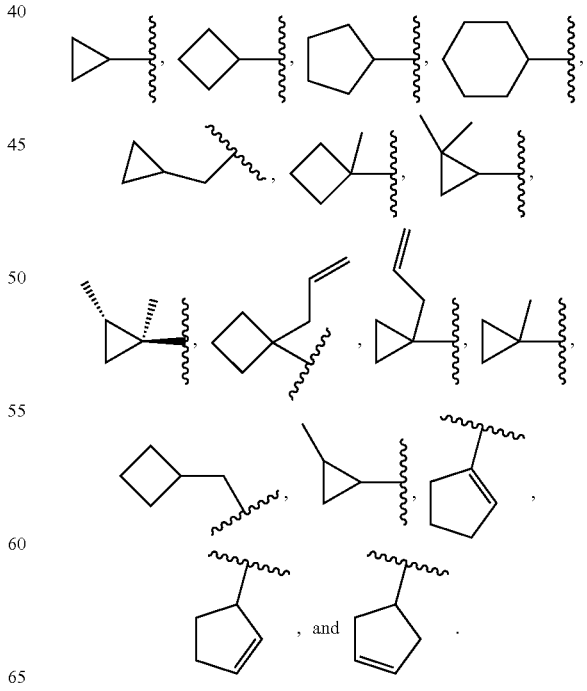

In another embodiment, R$_2$ is C$_3$-C$_7$ unbranched or branched cycloalkyl. Suitable C$_3$-C$_7$ unbranched or branched cycloalkyl include, without limitation, In another embodiment, $R_2$ is:

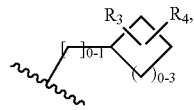

where $R_3$ and $R_4$ are independently selected from the group consisting of H, methyl, ethyl, propyl, isopropyl, vinyl, allyl, and propargyl. In specific embodiments, $R_3$ and $R_4$ are both H, $R_3$ and $R_4$ are both $CH_3$, $R_3$ is $CH_3$ and $R_4$ is H, or $R_3$ is allyl and $R_4$ is H.

In another embodiment, $R_2$ is:

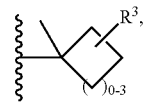

where, $R_3$ is selected from the group consisting of H, methyl, ethyl, propyl, isopropyl, vinyl, allyl, and propargyl.

Compounds of formula (A) of the present invention include, without limitation, the specific compounds set forth in the following Table 1.

TABLE 1

| Exemplary Compounds of Formula (A) | |
|---|---|
| Compound Name | Compound Structure |
| 1033B Menthyl cyclopropanecarboxylate | |
| 1034B Citronellyl isovalerate | |
| 1035A Citronellyl cyclopropanecarboxylate | |
| 1036A Citronellyl pivalate | |
| 1055A Thymyl cyclopropanecarboxylate | |
| 1055B Thymyl isovalerate | |

TABLE 1-continued

Exemplary Compounds of Formula (A)

| Compound Name | Compound Structure |
| --- | --- |
| 1066B 4-Nitrothymyl cyclopropanecarboxylate | 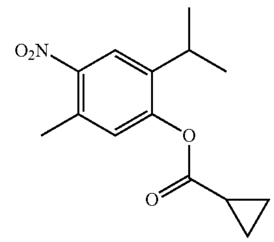 [SMILES: Cc1cc(OC(=O)C2CC2)c(C(C)C)cc1[N+](=O)[O-]] |
| 1075B 4-Bromothymyl cyclopropanecarboxylate | 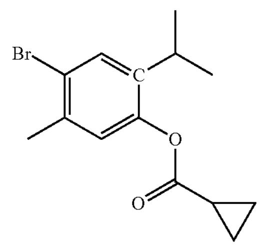 [SMILES: Cc1cc(OC(=O)C2CC2)c(C(C)C)cc1Br] |
| 1076A Eugenyl isovalerate | 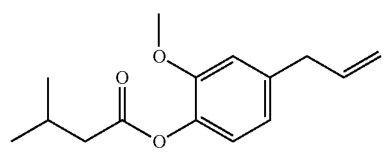 [SMILES: C=CCc1ccc(OC(=O)CC(C)C)c(OC)c1] |
| 1077B Thymyl 4-fluorobenzoate | 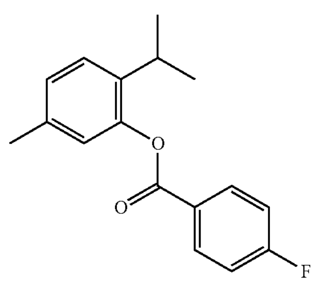 [SMILES: Cc1ccc(C(C)C)c(OC(=O)c2ccc(F)cc2)c1] |
| 1079A Carvacryl cyclopropanecarboxylate | 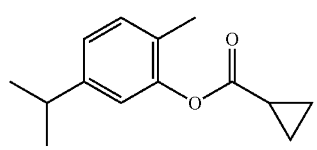 [SMILES: Cc1ccc(C(C)C)cc1OC(=O)C1CC1] |
| 1079C Carvacryl isovalerate | 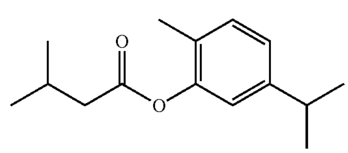 [SMILES: Cc1ccc(C(C)C)cc1OC(=O)CC(C)C] |
| 1089 Citronellyl formate | 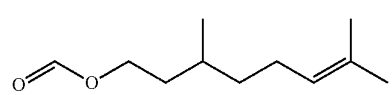 |
| 1107A Thymyl formate | 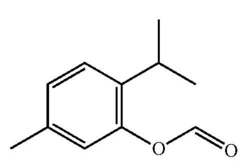 |

TABLE 1-continued
Exemplary Compounds of Formula (A)
| Compound Name | Compound Structure |
|---|---|
| 1107B Carvacryl formate | 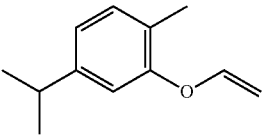 |
| 1121A Thymyl 2-fluoroisobutyrate | 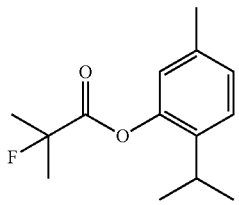 |
| 1121B Carvacryl 2-fluoroisobutyrate | 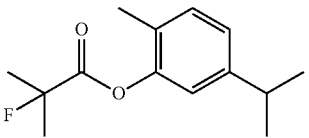 [SMILES: Cc1ccc(C(C)C)cc1OC(=O)C(C)(C)F] |
| 1142 Thymyl cyclobutanecarboxylate | 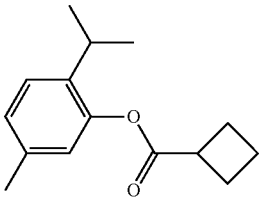 [SMILES: Cc1ccc(C(C)C)c(OC(=O)C2CCC2)c1] |
| 1143 Thymyl isobutyrate | 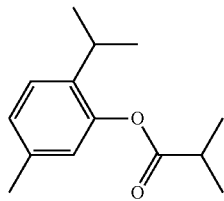 [SMILES: Cc1ccc(C(C)C)c(OC(=O)C(C)C)c1] |
| 1144B Chlorothymyl isobutyrate | 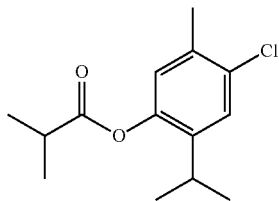 [SMILES: Cc1cc(OC(=O)C(C)C)c(C(C)C)cc1Cl] |
| 1146 Eugenyl formate | 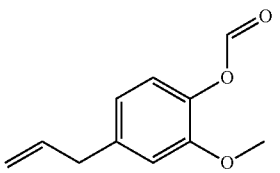 |
| 1147 Eugenyl cyclopropanecarboxylate | 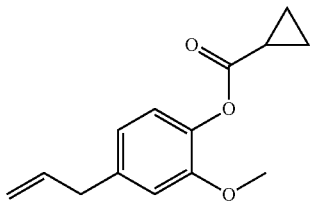 [SMILES: C=CCc1ccc(OC(=O)C2CC2)c(OC)c1] |

TABLE 1-continued

Exemplary Compounds of Formula (A)

| Compound Name | Compound Structure |
|---|---|
| 1148 Eugenyl isobutyrate | 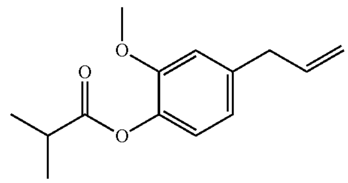 [SMILES: C=CCc1ccc(OC(=O)C(C)C)c(OC)c1] |
| 1149 Eugenyl cyclobutanecarboxylate | 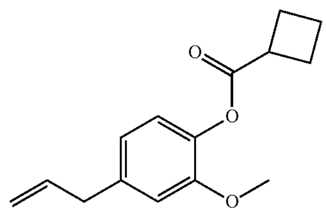 [SMILES: C=CCc1ccc(OC(=O)C2CCC2)c(OC)c1] |
| 1150 Eugenyl isovalerate | 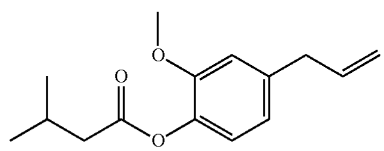 [SMILES: C=CCc1ccc(OC(=O)CC(C)C)c(OC)c1] |
| 2001 Vanillin Formate | 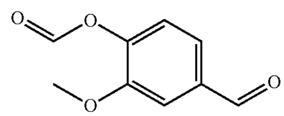 |
| 2002 Vanillin cyclopropanecarboxylate | 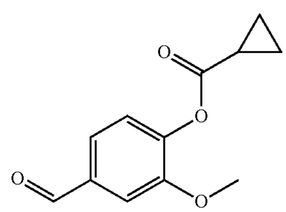 [SMILES: COc1cc(C=O)ccc1OC(=O)C1CC1] |
| 2003 Vanillin isobutyrate | 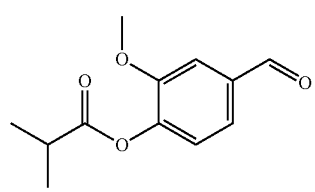 [SMILES: COc1cc(C=O)ccc1OC(=O)C(C)C] |
| 2004 Vanillin cyclobutanecarboxylate | 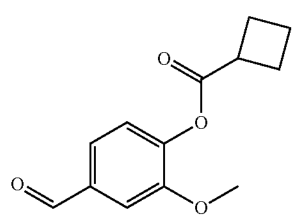 [SMILES: COc1cc(C=O)ccc1OC(=O)C1CCC1] |
| 2005 Vanillin isovalerate | 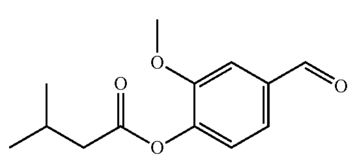 [SMILES: COc1cc(C=O)ccc1OC(=O)CC(C)C] |

TABLE 1-continued

Exemplary Compounds of Formula (A)

| Compound Name | Compound Structure |
| --- | --- |
| 2018 Myrtenyl cyclopropanecarboxylate | 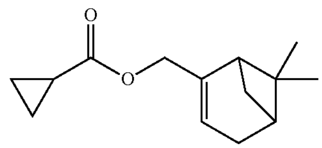 [SMILES: CC1(C)C2CC=C(COC(=O)C3CC3)C1C2] |
| 2023A Geranyl cyclopropanecarboxylate | 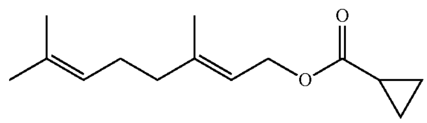 [SMILES: CC(C)=CCC/C(C)=C/COC(=O)C1CC1] |
| 2023B Neryl cyclopropanecarboxylate | 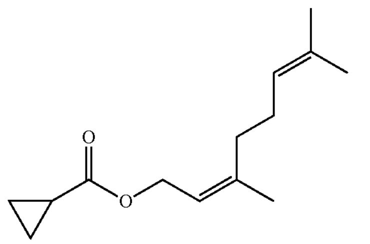 [SMILES: CC(C)=CCC/C(C)=C\COC(=O)C1CC1] |
| 2024A Geranyl cyclobutanecarboxylate | 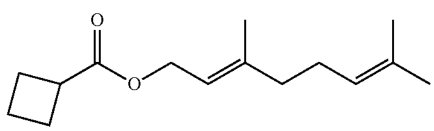 [SMILES: CC(C)=CCC/C(C)=C/COC(=O)C1CCC1] |
| 2024B Neryl cyclobutanecarboxylate | 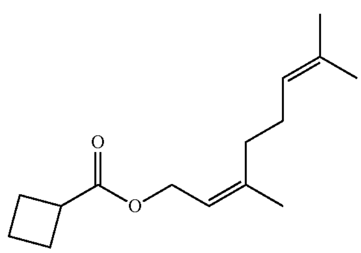 [SMILES: CC(C)=CCC/C(C)=C\COC(=O)C1CCC1] |
| 2025 Citronellyl cyclobutanecarboxylate | 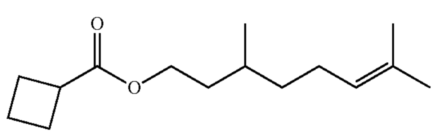 [SMILES: CC(C)=CCCC(C)CCOC(=O)C1CCC1] |
| 2030 Linalyl isobutyrate | 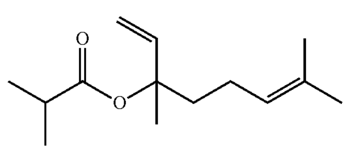 [SMILES: C=CC(C)(CCC=C(C)C)OC(=O)C(C)C] |
| 2032 Perillyl cyclopropanecarboxylate | 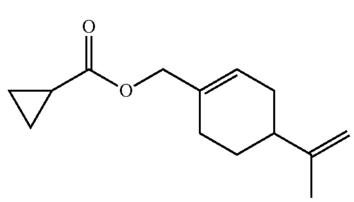 [SMILES: C=C(C)C1CC=C(COC(=O)C2CC2)CC1] |

TABLE 1-continued

Exemplary Compounds of Formula (A)

| Compound Name | Compound Structure |
| --- | --- |
| 2033 Perillyl cyclobutanecarboxylate | 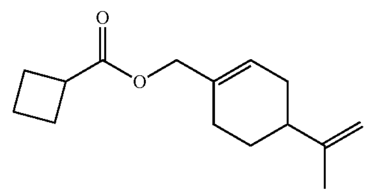 [SMILES: C=C(C)C1CC=C(COC(=O)C2CCC2)CC1] |
| 2034 Perillyl isobutyrate | 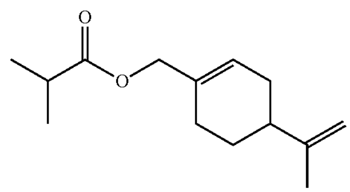 [SMILES: C=C(C)C1CC=C(COC(=O)C(C)C)CC1] |
| 2035 Perillyl isovalerate | 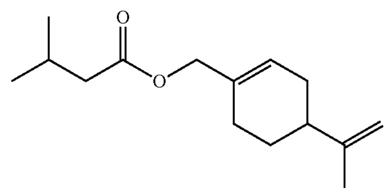 [SMILES: C=C(C)C1CC=C(COC(=O)CC(C)C)CC1] |
| 2038 Cinnamyl cyclopropanecarboxylate | 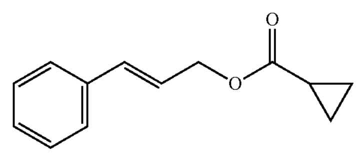 [SMILES: O=C(OC/C=C/c1ccccc1)C1CC1] |
| 2039 Cinnamyl cyclobutanecarboxylate | 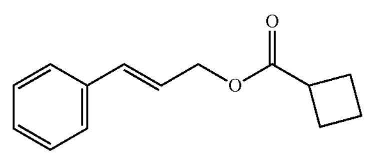 [SMILES: O=C(OC/C=C/c1ccccc1)C1CCC1] |
| 2041 Linalyl cyclopropanecarboxylate | 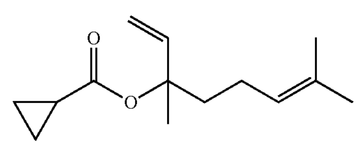 [SMILES: C=CC(C)(CCC=C(C)C)OC(=O)C1CC1] |
| 2054 α-Terpinyl cyclopropanecarboxylate | 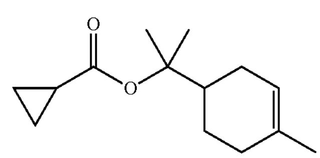 [SMILES: CC1=CCC(C(C)(C)OC(=O)C2CC2)CC1] |
| 2085 Thymyl cyclohexanecarboxylate | 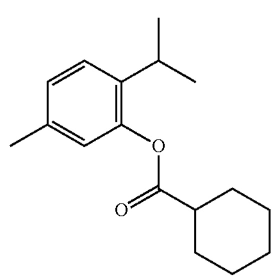 [SMILES: Cc1ccc(C(C)C)c(OC(=O)C2CCCCC2)c1] |

TABLE 1-continued

Exemplary Compounds of Formula (A)

| Compound Name | Compound Structure |
|---|---|
| 2094 Thymyl cyclopentanecarboxylate | 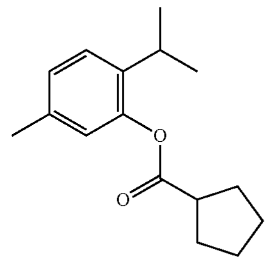 [SMILES: Cc1ccc(C(C)C)c(OC(=O)C2CCCC2)c1] |
| 2099 α-Terpinyl cyclobutanecarboxylate | 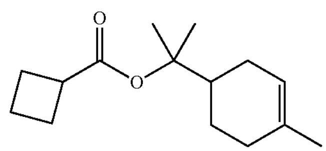 [SMILES: CC1=CCC(C(C)(C)OC(=O)C2CCC2)CC1] |
| 2103 Thymyl 3,3-dimethylacrylate | 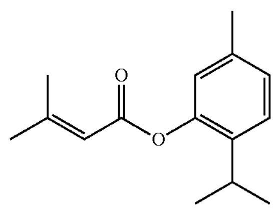 [SMILES: CC(C)=CC(=O)Oc1cc(C)ccc1C(C)C] |
| 2104 Thymyl 1-methyl-1-cyclobutanecarboxylate | 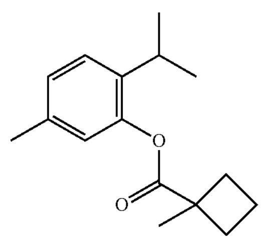 [SMILES: Cc1ccc(C(C)C)c(OC(=O)C2(C)CCC2)c1] |
| 2105 Citronellyl 3,3-dimethylacrylate | 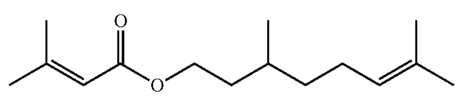 [SMILES: CC(C)=CCCC(C)CCOC(=O)C=C(C)C] |
| 2106 Citronellyl 1-methyl-1-cyclobutanecarboxylate | 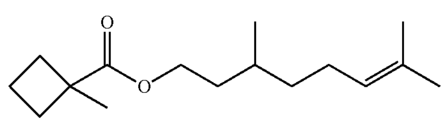 [SMILES: CC(C)=CCCC(C)CCOC(=O)C1(C)CCC1] |
| 2107 Neryl 3,3-dimethylacrylate | 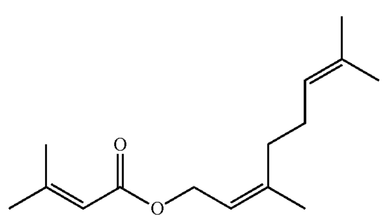 [SMILES: CC(C)=CCC/C(C)=C\COC(=O)C=C(C)C] |
| 2108 Neryl 1-methyl-1-cyclobutanecarboxylate | 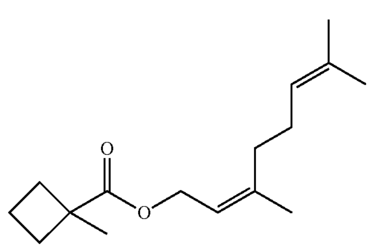 [SMILES: CC(C)=CCC/C(C)=C\COC(=O)C1(C)CCC1] |

TABLE 1-continued

Exemplary Compounds of Formula (A)

| Compound Name | Compound Structure |
| --- | --- |
| 2113 Menthyl cyclobutanecarboxylate | 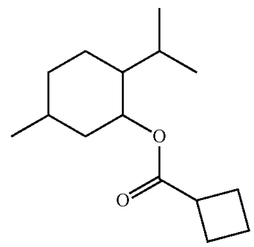 [SMILES: CC1CCC(C(C)C)C(OC(=O)C2CCC2)C1] |
| 2114 Perillyl cyclohexanecarboxylate | 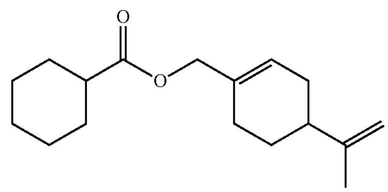 [SMILES: C=C(C)C1CC=C(COC(=O)C2CCCCC2)CC1] |
| 2115 Perillyl cyclopentanecarboxylate | 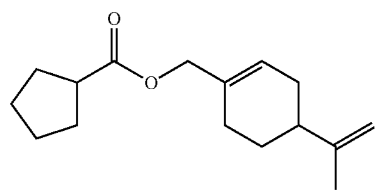 [SMILES: C=C(C)C1CC=C(COC(=O)C2CCCC2)CC1] |
| 2116 Menthyl cyclopentanecarboxylate | 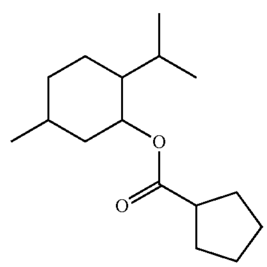 [SMILES: CC1CCC(C(C)C)C(OC(=O)C2CCCC2)C1] |
| 2117 Menthyl cyclohexanecarboxylate | 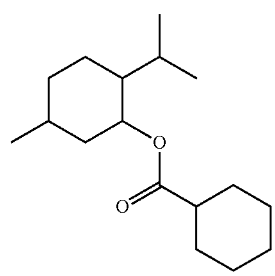 [SMILES: CC1CCC(C(C)C)C(OC(=O)C2CCCCC2)C1] |
| 2118 Menthyl 3,3-dimethylacrylate | 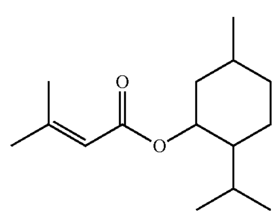 [SMILES: CC(C)=CC(=O)OC1CC(C)CCC1C(C)C] |
| 2119 Citronellyl cyclopentanecarboxylate | 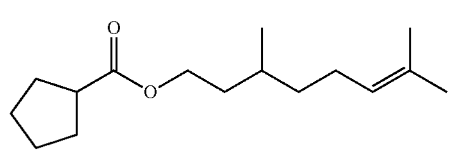 [SMILES: CC(C)=CCCC(C)CCOC(=O)C1CCCC1] |

TABLE 1-continued

Exemplary Compounds of Formula (A)

| Compound Name | Compound Structure |
|---|---|
| 2120 Fenchyl cyclopropanecarboxylate | 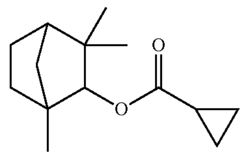 [SMILES: CC12CCC(C1)C(C)(C)C2OC(=O)C1CC1] |
| 2121 Fenchyl cyclobutanecarboxylate | 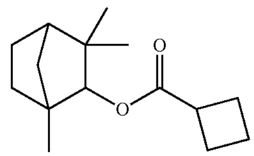 [SMILES: CC12CCC(C1)C(C)(C)C2OC(=O)C1CCC1] |
| 2122 Fenchyl isovalerate | 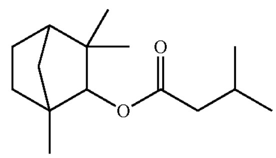 [SMILES: CC(C)CC(=O)OC1C2(C)CCC(C2)C1(C)C] |
| 2123 Fenchyl formate | 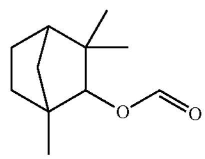 |
| 2124 Bornyl cyclopropanecarboxylate | 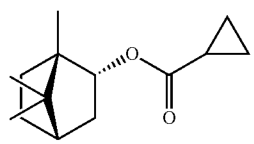 [SMILES: CC1(C)[C@H]2CC[C@]1(C)[C@H](OC(=O)C1CC1)C2] |
| 2125 Bornyl cyclobutanecarboxylate | 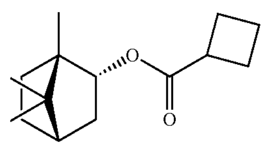 [SMILES: CC1(C)[C@H]2CC[C@]1(C)[C@H](OC(=O)C1CCC1)C2] |
| 2126 Bornyl isovalerate | 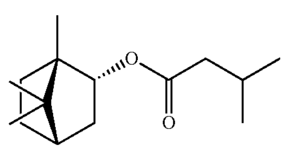 [SMILES: CC(C)CC(=O)O[C@@H]1C[C@@H]2CC[C@@]1(C)C2(C)C] |
| 2127 Bornyl formate | 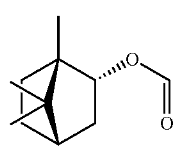 |
| 2128 Isobornyl cyclopropanecarboxylate | 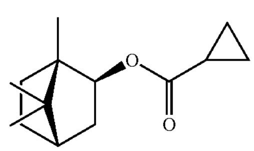 [SMILES: CC1(C)[C@H]2CC[C@]1(C)[C@@H](OC(=O)C1CC1)C2] |

TABLE 1-continued

Exemplary Compounds of Formula (A)

| Compound Name | Compound Structure |
|---|---|
| 2129 Isobornyl cyclobutanecarboxylate | 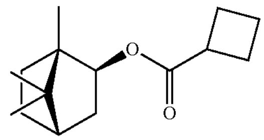 [SMILES: CC1(C)[C@H]2CC[C@]1(C)[C@@H](OC(=O)C1CCC1)C2] |
| 2130 Isobornyl isovalerate | 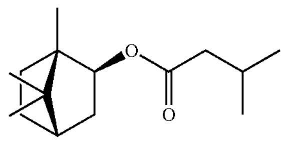 [SMILES: CC(C)CC(=O)O[C@H]1C[C@@H]2CC[C@@]1(C)C2(C)C] |
| 2131 Isobornyl formate | 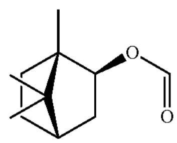 |
| 2151 Linalyl cyclobutanecarboxylate | 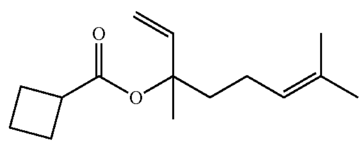 [SMILES: C=CC(C)(CCC=C(C)C)OC(=O)C1CCC1] |
| 2152 Linalyl isovalerate | 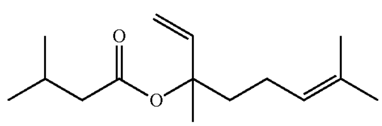 [SMILES: C=CC(C)(CCC=C(C)C)OC(=O)CC(C)C] |
| 2153 Linalyl formate | 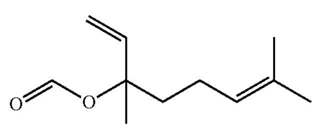 |
| 2177 Citronellyl tiglate | 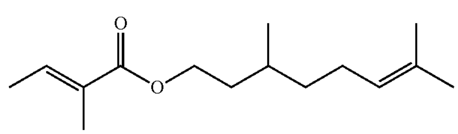 [SMILES: C/C=C(\C)C(=O)OCCC(C)CCC=C(C)C] |
| 2178 Menthyl tiglate | 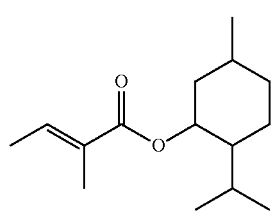 [SMILES: C/C=C(\C)C(=O)OC1CC(C)CCC1C(C)C] |
| 2179 Thymyl tiglate | 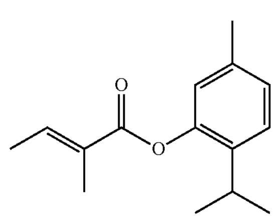 [SMILES: C/C=C(\C)C(=O)Oc1cc(C)ccc1C(C)C] |

TABLE 1-continued
Exemplary Compounds of Formula (A)
| Compound Name | Compound Structure |
|---|---|
| 2180 Citronellyl thiophene-2-carboxylate | 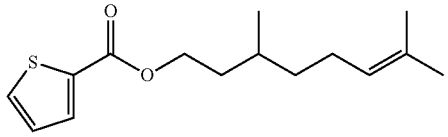 [SMILES: CC(C)=CCCC(C)CCOC(=O)c1cccs1] |
| 2181 Menthyl thiophene-2-carboxylate | 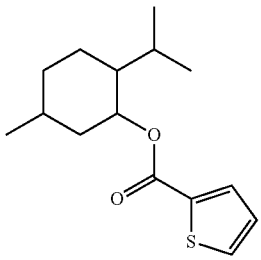 [SMILES: CC1CCC(C(C)C)C(OC(=O)c2cccs2)C1] |
| 2182 Thymyl thiophene-2-carboxylate | 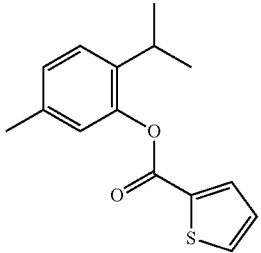 |
| 2183 Citronellyl levulinate | 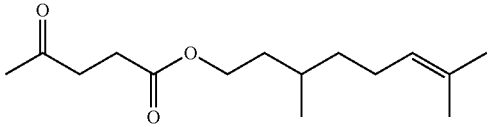 [SMILES: CC(=O)CCC(=O)OCCC(C)CCC=C(C)C] |
| 2184 Menthyl levulinate | 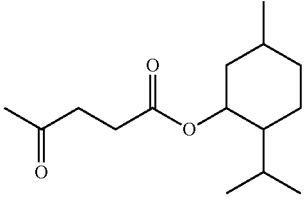 [SMILES: CC(=O)CCC(=O)OC1CC(C)CCC1C(C)C] |
| 2185 Thymyl levulinate | 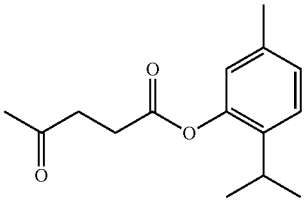 [SMILES: CC(=O)CCC(=O)Oc1cc(C)ccc1C(C)C] |
| 2186 Citronellyl 2-furoate | 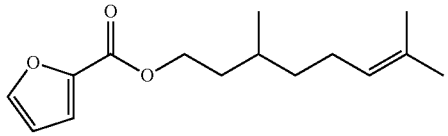 |

TABLE 1-continued

Exemplary Compounds of Formula (A)

| Compound Name | Compound Structure |
| --- | --- |
| 2187 Menthyl 2-furoate | 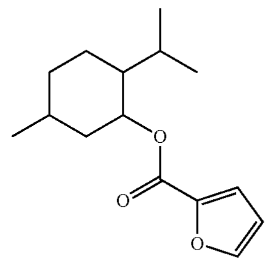 [SMILES: CC1CCC(C(C)C)C(OC(=O)c2ccco2)C1] |
| 2188 Thymyl 2-furoate | 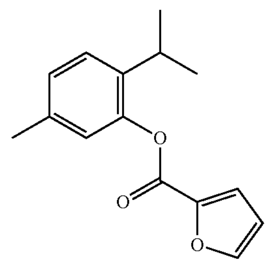 [SMILES: Cc1ccc(C(C)C)c(OC(=O)c2ccco2)c1] |
| 2189 Citronellyl benzoate | 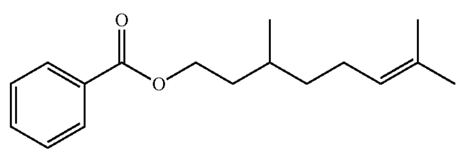 [SMILES: CC(C)=CCCC(C)CCOC(=O)c1ccccc1] |
| 2190 Menthyl benzoate | 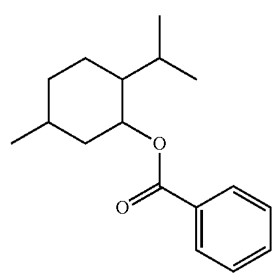 [SMILES: CC1CCC(C(C)C)C(OC(=O)c2ccccc2)C1] |
| 2191 Thymyl benzoate | 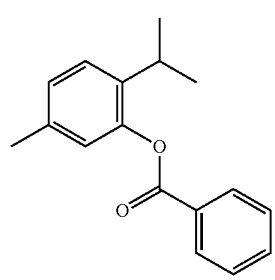 [SMILES: Cc1ccc(C(C)C)c(OC(=O)c2ccccc2)c1] |
| 2194 Thymyl difluoroacetate | 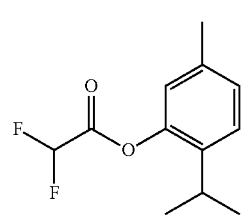 [SMILES: Cc1ccc(C(C)C)c(OC(=O)C(F)F)c1] |

TABLE 1-continued

Exemplary Compounds of Formula (A)

| Compound Name | Compound Structure |
| --- | --- |
| 2201 Myrtenyl cyclobutanecarboxylate | 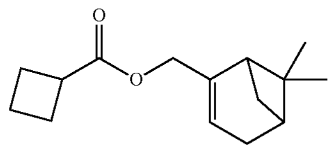 [SMILES: CC1(C)C2CC=C(COC(=O)C3CCC3)C1C2] |
| 2202B Carvacryl cyclobutanecarboxylate | 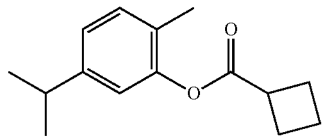 [SMILES: Cc1ccc(C(C)C)cc1OC(=O)C1CCC1] |
| 2203 Citronellyl hexanecarboxylate | 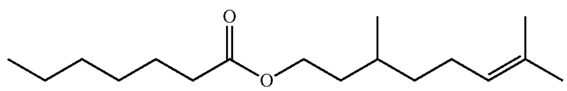 [SMILES: CCCCCCC(=O)OCCC(C)CCC=C(C)C] |
| 2204 Citronellyl isobutyrate | 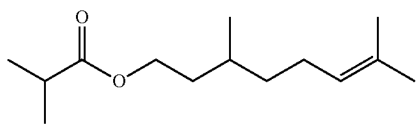 [SMILES: CC(C)=CCCC(C)CCOC(=O)C(C)C] |
| 2205 Carvacryl isobutyrate | 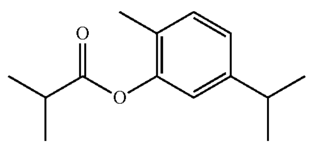 [SMILES: Cc1ccc(C(C)C)cc1OC(=O)C(C)C] |
| 2206A Geranyl cyclopentanecarboxylate | 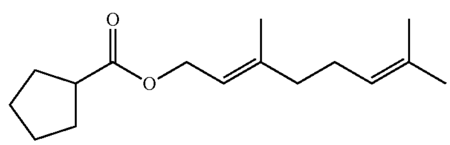 [SMILES: CC(C)=CCC/C(C)=C/COC(=O)C1CCCC1] |
| 2206B Neryl cyclopentanecarboxylate | 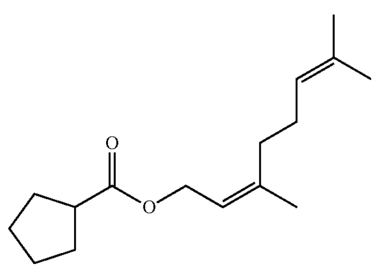 [SMILES: CC(C)=CCC/C(C)=C\COC(=O)C1CCCC1] |
| 2207A Geranyl cyclohexanecarboxylate | 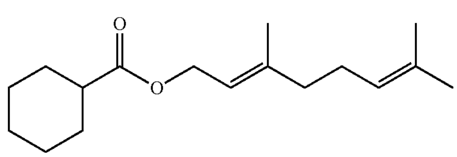 [SMILES: CC(C)=CCC/C(C)=C/COC(=O)C1CCCCC1] |
| 2207B Neryl cyclohexanecarboxylate | 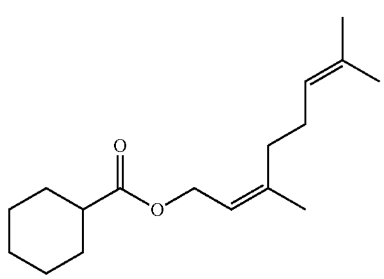 [SMILES: CC(C)=CCC/C(C)=C\COC(=O)C1CCCCC1] |

TABLE 1-continued

Exemplary Compounds of Formula (A)

| Compound Name | Compound Structure |
|---|---|
| 2208 Citronellyl 2-fluoroisobutyrate | 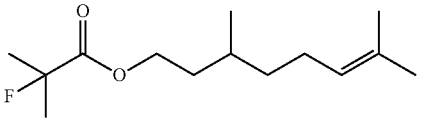 [SMILES: CC(C)=CCCC(C)CCOC(=O)C(C)(C)F] |
| 2192 Citronellyl difluoroacetate | 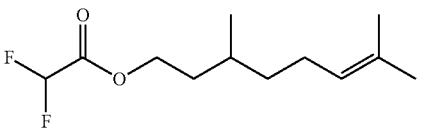 [SMILES: CC(C)=CCCC(C)CCOC(=O)C(F)F] |
| 2198 Citronellyl cyanoacetate | 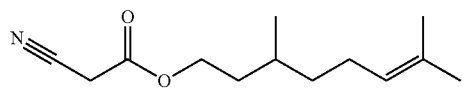 [SMILES: CC(C)=CCCC(C)CCOC(=O)CC#N] |
| 2210 Menthyl 1-methyl-1-cyclobutanecarboxylate | 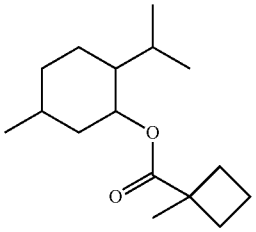 [SMILES: CC1CCC(C(C)C)C(OC(=O)C2(C)CCC2)C1] |
| 2214 7-(2-Methylpropanoyloxy)coumarin | 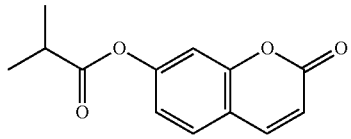 [SMILES: CC(C)C(=O)Oc1ccc2ccc(=O)oc2c1] |
| 2215 7-(3-Methylbutanoyloxy)coumarin | 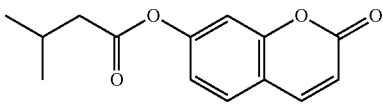 [SMILES: CC(C)CC(=O)Oc1ccc2ccc(=O)oc2c1] |
| 2216 7-(Cyclopropanecarboxoyloxy)coumarin | 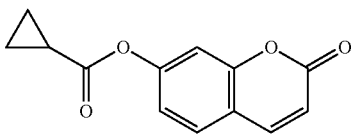 [SMILES: O=C(Oc1ccc2ccc(=O)oc2c1)C1CC1] |
| 2217 7-(Cyclobutanecarboxoyloxy)coumarin | 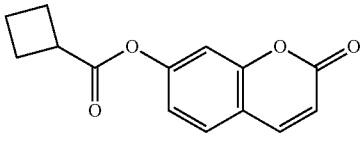 [SMILES: O=C(Oc1ccc2ccc(=O)oc2c1)C1CCC1] |
| 2218 7-(Cyclopentanecarboxoyloxy)coumarin | 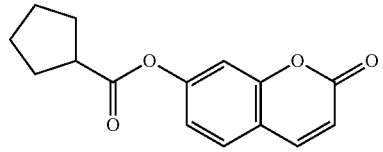 [SMILES: O=C(Oc1ccc2ccc(=O)oc2c1)C1CCCC1] |
| 2219 Carvyl formate | 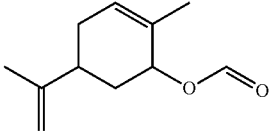 |

TABLE 1-continued

Exemplary Compounds of Formula (A)

| Compound Name | Compound Structure |
|---|---|
| 2220 Carvyl isobutyrate | 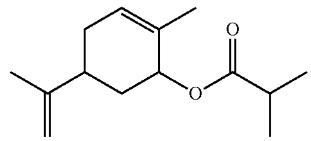 [SMILES: C=C(C)C1CC=C(C)C(OC(=O)C(C)C)C1] |
| 2221 Carvyl isovalerate | 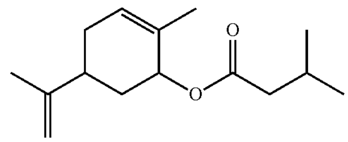 [SMILES: C=C(C)C1CC=C(C)C(OC(=O)CC(C)C)C1] |
| 2222 Carvyl cyclopropanecarboxylate | 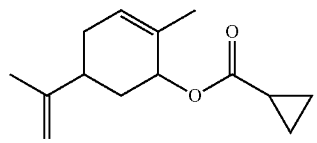 [SMILES: C=C(C)C1CC=C(C)C(OC(=O)C2CC2)C1] |
| 2223 Carvyl cyclobutanecarboxylate | 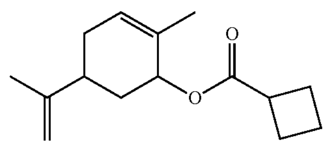 [SMILES: C=C(C)C1CC=C(C)C(OC(=O)C2CCC2)C1] |
| 2224 Carvyl cyclopentanecarboxylate | 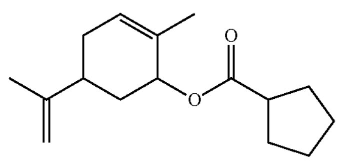 [SMILES: C=C(C)C1CC=C(C)C(OC(=O)C2CCCC2)C1] |
| 2225 cis-Verbenyl cyclopropanecarboxylate | 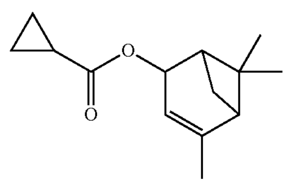 [SMILES: CC1=CC(OC(=O)C2CC2)C2CC1C2(C)C] |
| 2226 cis-Verbenyl cyclobutanecarboxylate | 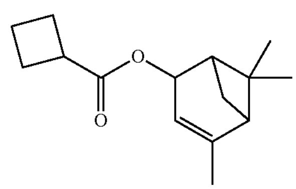 [SMILES: CC1=CC(OC(=O)C2CCC2)C2CC1C2(C)C] |
| 2227 cis-Verbenyl cyclopentanecarboxylate | 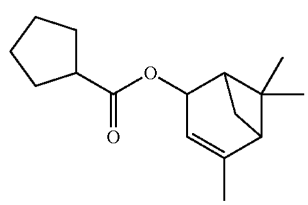 [SMILES: CC1=CC(OC(=O)C2CCCC2)C2CC1C2(C)C] |
| 2228 Thymyl cyclopropylacetate | 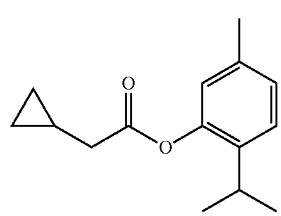 [SMILES: Cc1ccc(C(C)C)c(OC(=O)CC2CC2)c1] |

TABLE 1-continued

Exemplary Compounds of Formula (A)

| Compound Name | Compound Structure |
| --- | --- |
| 2229 Citronellyl cyclopropylacetate | 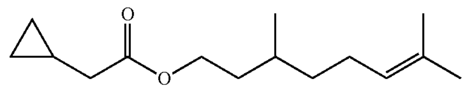 [SMILES: CC(C)=CCCC(C)CCOC(=O)CC1CC1] |
| 2230 Menthyl cyclopropylacetate | 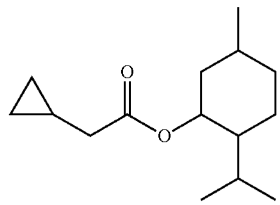 [SMILES: CC1CCC(C(C)C)C(OC(=O)CC2CC2)C1] |
| 2232 Citronellyl 2,2-difluoropropanoate | 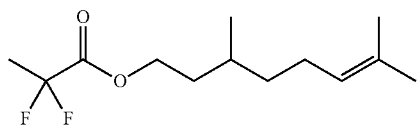 [SMILES: CC(C)=CCCC(C)CCOC(=O)C(C)(F)F] |
| 2235 Citronellyl 3,3,3-trifluoropropanoate | 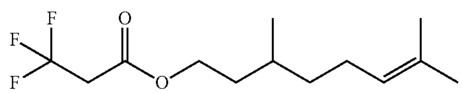 [SMILES: CC(C)=CCCC(C)CCOC(=O)CC(F)(F)F] |
| 2243 Thymyl thiophen-2-ylacetate | 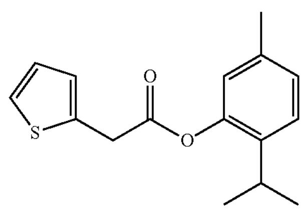 [SMILES: Cc1ccc(C(C)C)c(OC(=O)Cc2cccs2)c1] |
| 2244 Citronellyl thiophen-2-ylacetate | 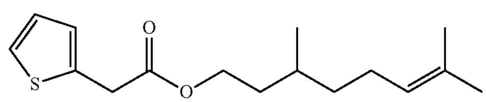 [SMILES: CC(C)=CCCC(C)CCOC(=O)Cc1cccs1] |
| 2245 Menthyl thiophen-2-ylacetate | 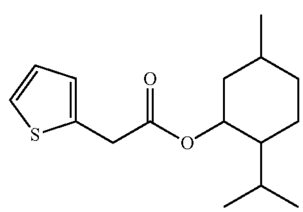 [SMILES: CC1CCC(C(C)C)C(OC(=O)Cc2cccs2)C1] |
| 2254 Cinnamyl isovalerate | 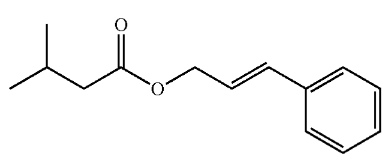 [SMILES: CC(C)CC(=O)OC/C=C/c1ccccc1] |
| 2255A Geranyl isovalerate | 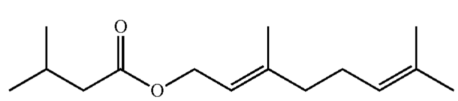 [SMILES: CC(C)=CCC/C(C)=C/COC(=O)CC(C)C] |

TABLE 1-continued
Exemplary Compounds of Formula (A)
| Compound Name | Compound Structure |
|---|---|
| 2255B Neryl isovalerate | 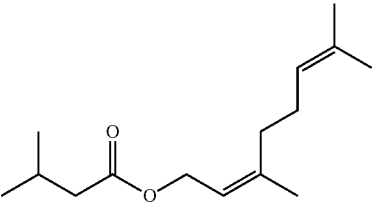 [SMILES: CC(C)=CCC/C(C)=C\COC(=O)CC(C)C] |
| 2256 Menthyl isovalerate | 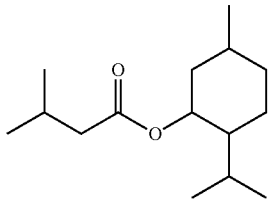 |
| 2257 α-Terpinyl isovalerate | 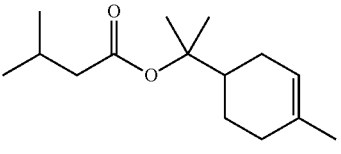 [SMILES: CC1=CCC(C(C)(C)OC(=O)CC(C)C)CC1] |
| 2258 Myrtenyl isovalerate | 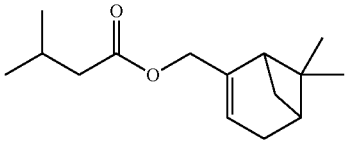 [SMILES: CC(C)CC(=O)OCC1=CCC2CC1C2(C)C] |
| 2260 Cinnamyl isobutyrate | 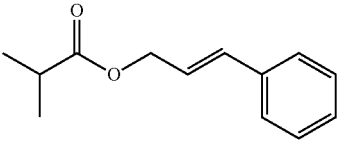 |
| 2261A Geranyl isobutyrate | 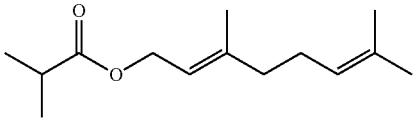 [SMILES: CC(C)=CCC/C(C)=C/COC(=O)C(C)C] |
| 2261B Neryl isobutyrate | 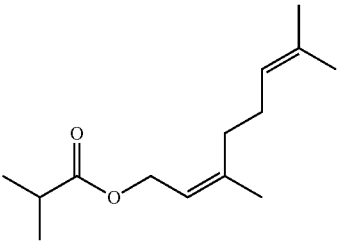 [SMILES: CC(C)=CCC/C(C)=C\COC(=O)C(C)C] |
| 2262 Menthyl isobutyrate | 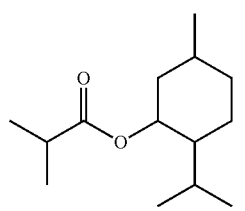 [SMILES: CC1CCC(C(C)C)C(OC(=O)C(C)C)C1] |

TABLE 1-continued

Exemplary Compounds of Formula (A)

| Compound Name | Compound Structure |
|---|---|
| 2263 α-Terpinyl isobutyrate | 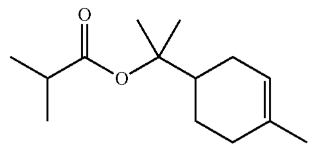 [SMILES: CC1=CCC(C(C)(C)OC(=O)C(C)C)CC1] |
| 2264A Bornyl isobutyrate | 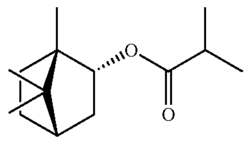 [SMILES: CC(C)C(=O)O[C@@H]1C[C@@H]2CC[C@@]1(C)C2(C)C] |
| 2264B Isobornyl isobutyrate | 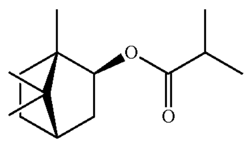 [SMILES: CC(C)C(=O)O[C@H]1C[C@@H]2CC[C@@]1(C)C2(C)C] |
| 2265 Fenchyl isobutyrate | 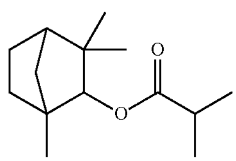 [SMILES: CC(C)C(=O)OC1C2(C)CCC(C2)C1(C)C] |
| 2266 Myrtenyl isobutyrate | 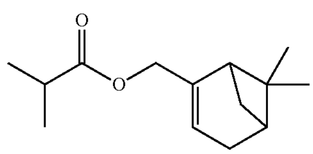 [SMILES: CC(C)C(=O)OCC1=CCC2CC1C2(C)C] |
| 2267 cis-Verbenyl isobutyrate | 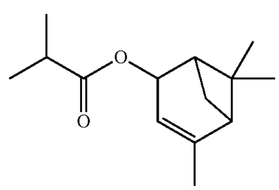 [SMILES: CC1=CC(OC(=O)C(C)C)C2CC1C2(C)C] |
| 2269 Menthyl formate | 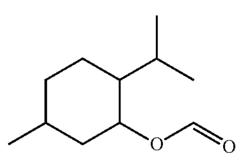 |
| 2282 Carvacryl cyclopentanecarboxylate | 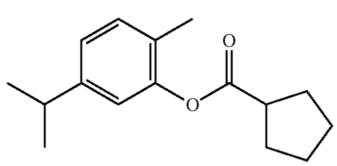 [SMILES: Cc1ccc(C(C)C)cc1OC(=O)C1CCCC1] |
| 2283 Carvacryl cyclohexanecarboxylate | 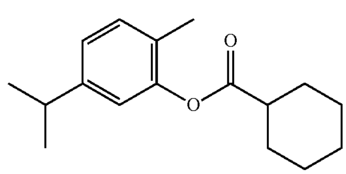 [SMILES: Cc1ccc(C(C)C)cc1OC(=O)C1CCCCC1] |

TABLE 1-continued

Exemplary Compounds of Formula (A)

| Compound Name | Compound Structure |
|---|---|
| 3014 cis-Verbenyl isovalerate | 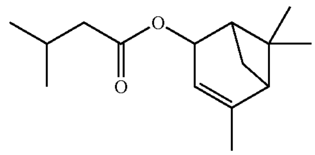 [SMILES: CC1=CC(OC(=O)CC(C)C)C2CC1C2(C)C] |
| 3015 Thymyl pivalate | 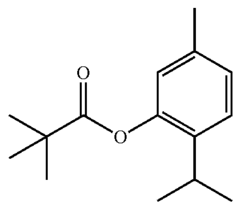 [SMILES: Cc1ccc(C(C)C)c(OC(=O)C(C)(C)C)c1] |
| 3016 Menthyl pivalate | 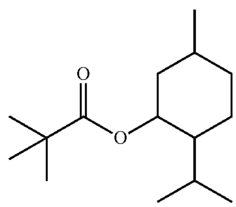 [SMILES: CC1CCC(C(C)C)C(OC(=O)C(C)(C)C)C1] |
| 3020 Thymyl 2,2-dimethylcyclopropanecarboxylate | 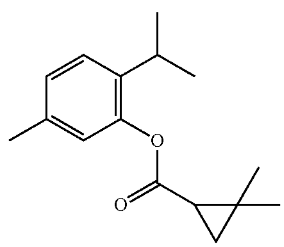 |
| 3021 Citronellyl 2,2-dimethylcyclopropanecarboxylate | 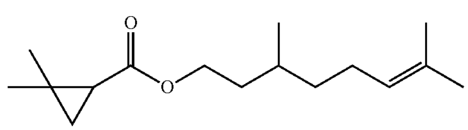 [SMILES: CC(C)=CCCC(C)CCOC(=O)C1CC1(C)C] |
| 3022 Menthyl 2,2-dimethylcyclopropanecarboxylate | 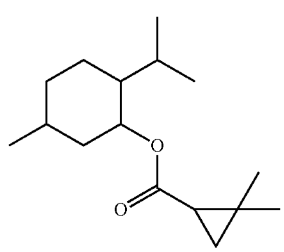 |
| 3023 Thymyl trans-1,2-dimethylcyclopropanecarboxylate | 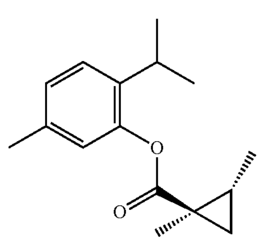 |

TABLE 1-continued

Exemplary Compounds of Formula (A)

| Compound Name | Compound Structure |
|---|---|
| 3024 Citronellyl trans-1,2-dimethylcyclopropanecarboxylate | 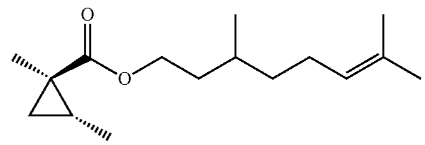 [SMILES: CC(C)=CCCC(C)CCOC(=O)[C@]1(C)C[C@H]1C] |
| 3025 Menthyl trans-1,2-dimethylcyclopropanecarboxylate | 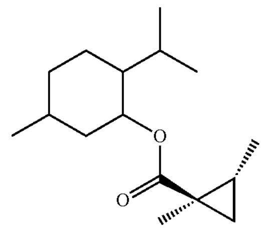 |
| 3029 Thymyl 1-allylcyclobutanecarboxylate | 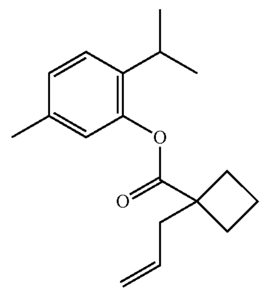 [SMILES: C=CCC1(C(=O)Oc2cc(C)ccc2C(C)C)CCC1] |
| 3030 Citronellyl 1-allylcyclobutanecarboxylate | 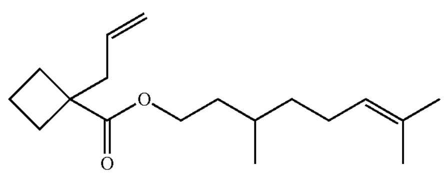 [SMILES: C=CCC1(C(=O)OCCC(C)CCC=C(C)C)CCC1] |
| 3031 Menthyl 1-allylcyclobutanecarboxylate | 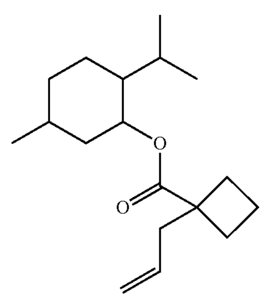 [SMILES: C=CCC1(C(=O)OC2CC(C)CCC2C(C)C)CCC1] |
| 3032 Thymyl 1-allylcyclopropanecarboxylate | 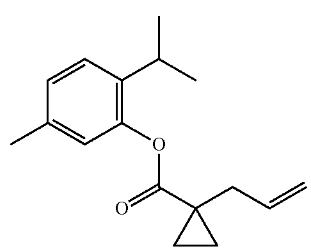 [SMILES: C=CCC1(C(=O)Oc2cc(C)ccc2C(C)C)CC1] |
| 3033 Citronellyl 1-allylcyclopropanecarboxylate | 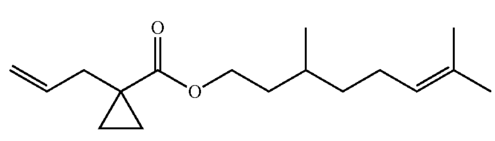 [SMILES: C=CCC1(C(=O)OCCC(C)CCC=C(C)C)CC1] |

TABLE 1-continued

Exemplary Compounds of Formula (A)

| Compound Name | Compound Structure |
|---|---|
| 3034 Menthyl 1-allylcyclopropanecarboxylate | 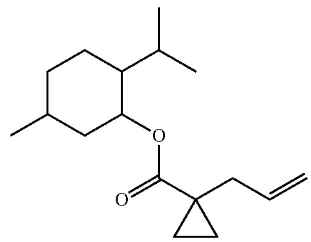 [SMILES: C=CCC1(C(=O)OC2CC(C)CCC2C(C)C)CC1] |
| 3035 Thymyl 1-methylcyclopropanecarboxylate | 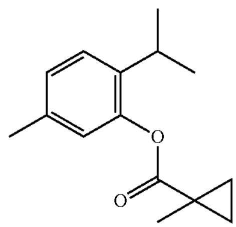 [SMILES: Cc1ccc(C(C)C)c(OC(=O)C2(C)CC2)c1] |
| 3036 Citronellyl 1-methylcyclopropanecarboxylate | 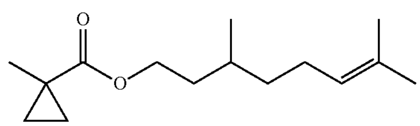 [SMILES: CC(C)=CCCC(C)CCOC(=O)C1(C)CC1] |
| 3037 Menthyl 1-methylcyclopropanecarboxylate | 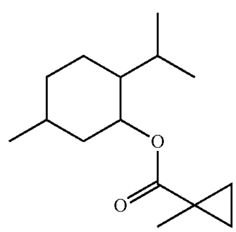 [SMILES: CC1CCC(C(C)C)C(OC(=O)C2(C)CC2)C1] |
| 3067 Citronellyl 3-oxocyclobutanecarboxylate | 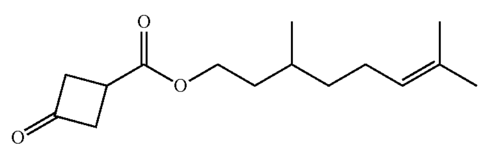 [SMILES: CC(C)=CCCC(C)CCOC(=O)C1CC(=O)C1] |
| 3068 Citronellyl 3-methylcyclobutanecarboxylate | 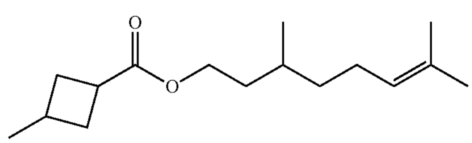 [SMILES: CC(C)=CCCC(C)CCOC(=O)C1CC(C)C1] |
| 3069 Citronellyl 3,3-difluorocyclobutanecarboxylate | 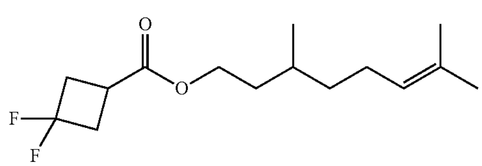 [SMILES: CC(C)=CCCC(C)CCOC(=O)C1CC(F)(F)C1] |
| Citronellyl chloroacetate | 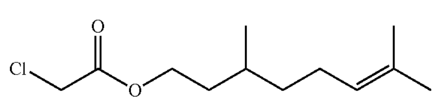 |

Another aspect of the present invention relates to a compound of formula (B) as follows:

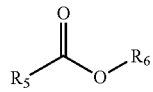
(B)

where

R$_5$ is a monoterpenoid or phenylpropanoid moiety and

R$_6$ is substituted or unsubstituted and is selected from the group consisting of C$_3$-C$_7$ unbranched or branched alkyl, C$_2$-C$_7$ unbranched or branched alkenyl, C$_3$-C$_7$ unbranched or branched alkynyl, C$_3$-C$_7$ unbranched or branched cycloalkyl, C$_3$-C$_7$ unbranched or branched cycloalkenyl, C$_3$-C$_7$ unbranched or branched heterocycle, C$_2$-C$_7$ saturated or unsaturated hydroxyalkyl, and —(CR$_{11}$R$_{12}$)$_p$—O—(CR$_{11}$R$_{12}$)$_q$—OH;

R$_{11}$ and R$_{12}$ are individually selected from H or C$_{1-6}$ alkyl;

p is an integer from 1 to 4; and q is an integer from 1 to 4, with the proviso that the compound is not selected from the group consisting of

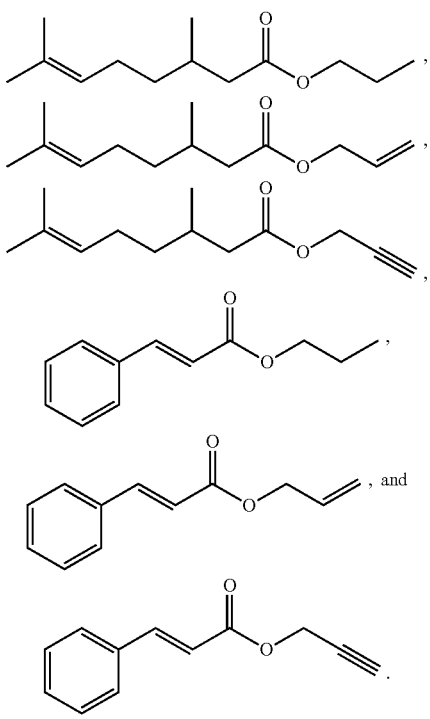

According to one embodiment, R$_6$ is:

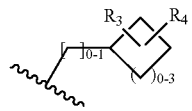

where, R$_3$ and R$_4$ are independently selected from the group consisting of H, methyl, ethyl, propyl, isopropyl, vinyl, allyl, and propargyl. In specific embodiments, R$_3$ and R$_4$ are both H, R$_3$ and R$_4$ are both CH$_3$, R$_3$ is CH$_3$ and R$_4$ is H, or R$_2$ is allyl and R$_4$ is H.

In another embodiment, R$_6$ is:

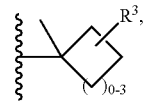

where R$_3$ is selected from the group consisting of H, methyl, ethyl, propyl, isopropyl, vinyl, allyl, and propargyl.

In another embodiment, R$_6$ is:

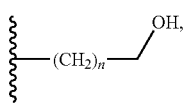

where n is an integer from 1-4. In one particular embodiment, n is 2.

In one embodiment, R$_6$ is C$_3$-C$_7$ unbranched or branched alkyl. Suitable C$_3$-C$_7$ unbranched or branched alkyl groups include, without limitation, methyl, ethyl, propyl, isopropyl, 1-methylpropyl, 2-methylpropyl, 1,1-dimethylethyl, 1-methylbutyl, 2-methylbutyl, 1-ethylpropyl, 1,1-dimethylpropyl, and 1,2-dimethylpropyl.

In another embodiment, R$_6$ is C$_2$-C$_7$ unbranched or branched alkenyl. Suitable C$_2$-C$_7$ unbranched or branched alkenyl groups include, without limitation, allyl, propargyl, prenyl, and isoprenyl.

In another embodiment, R$_6$ is C$_3$-C$_7$ unbranched or branched cycloalkyl. Suitable C$_3$-C$_7$ unbranched or branched cycloalkyl groups include, without limitation, cyclobut-1-en-1-yl, cyclobut-2-en-1-yl, cyclopent-1-en-1-yl, cyclopent-2-en-1-yl, cyclopent-3-en-1-yl, and 1-methylcyclopent-3-en-1-yl.

In another embodiment, R$_6$ is C$_3$-C$_7$ unbranched or branched cycloalkenyl. Suitable C$_3$-C$_7$ unbranched or branched cycloalkenyl groups include, without limitation, cyclobut-1-en-1-yl, cyclobut-2-en-1-yl, cyclopent-1-en-1-yl, cyclopent-2-en-1-yl, cyclopent-3-en-1-yl, and 1-methylcyclopent-3-en-1-yl.

According to one embodiment, R$_5$ is selected from the group consisting of

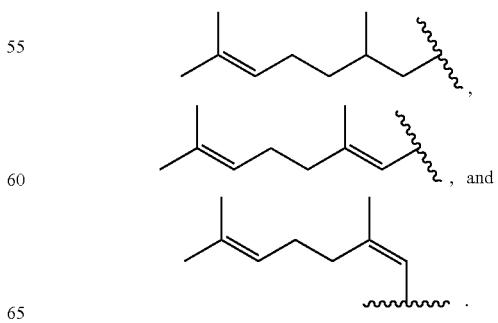

In another embodiment, $R_5$ is selected from the group consisting of

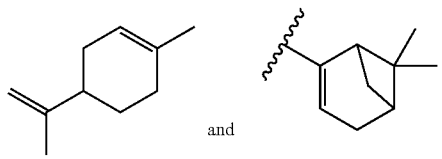

and

In another embodiment, $R_5$ is a substituted cinnamic acid. For example, $R_5$ is:

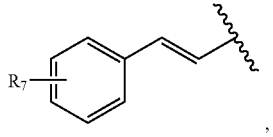

where $R_7$ is selected from the group consisting of H, OH, OMe, and OEt.

In another embodiment, $R_5$ has a structure

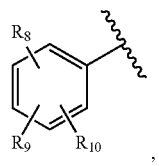

where $R_8$ is selected from the group consisting of OH, OMe, and OEt;

$R_9$ is selected from the group consisting of H, OH, and OMe; and $R_{10}$ is selected from the group consisting of H, OH, and OMe.

In another embodiment, $R_5$ is selected from the group consisting of

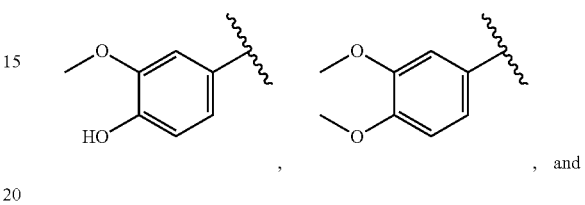

, and

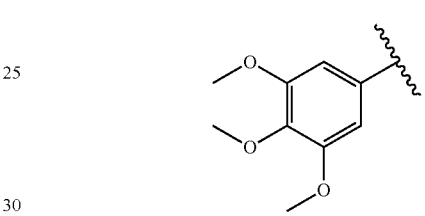

Compounds of formula (B) of the present invention include, without limitation, the specific compounds set forth in the following Table 2.

TABLE 2

Exemplary Compounds of Formula (B)

| Compound Name | Compound Structure |
|---|---|
| 2155 2-Hydroxyethyl citronellate | 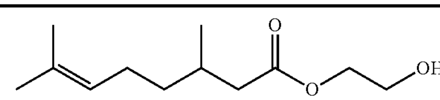 |
| 1092A 2-Hydroxyethyl cinnamate | 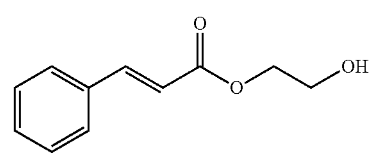 [SMILES: O=C(/C=C/c1ccccc1)OCCO] |
| 2020 Cyclopropylmethyl geranate | 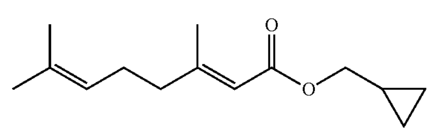 [SMILES: CC(C)=CCC/C(C)=C/C(=O)OCC1CC1] |
| 2026 Cyclobutylmethyl citronellate | 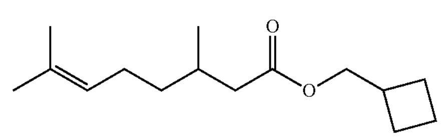 [SMILES: CC(C)=CCCC(C)CC(=O)OCC1CCC1] |
| 2027 Cyclopropylmethyl citronellate | 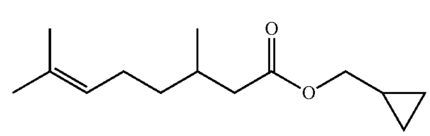 [SMILES: CC(C)=CCCC(C)CC(=O)OCC1CC1] |

TABLE 2-continued

Exemplary Compounds of Formula (B)

| Compound Name | Compound Structure |
| --- | --- |
| 2036 Cyclopropylmethyl cinnamate | 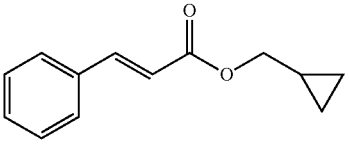 [SMILES: O=C(/C=C/c1ccccc1)OCC1CC1] |
| 2037 Cyclobutylmethyl cinnamate | 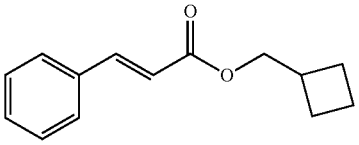 [SMILES: O=C(/C=C/c1ccccc1)OCC1CCC1] |
| 2140 2-Hydroxypropyl cinnamate | 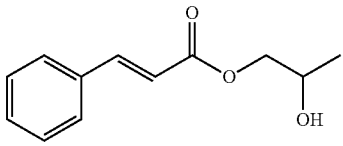 |
| 2141 3-Hydroxypropyl cinnamate | 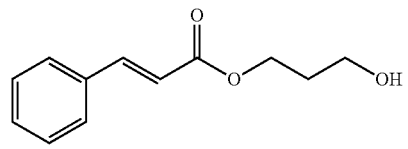 [SMILES: O=C(/C=C/c1ccccc1)OCCCO] |
| 2142 2-Hydroxypropyl geranate | 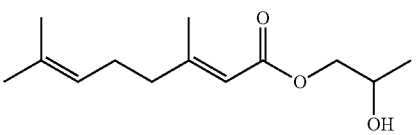 [SMILES: CC(C)=CCC/C(C)=C/C(=O)OCC(C)O] |
| 2143 3-Hydroxypropyl geranate | 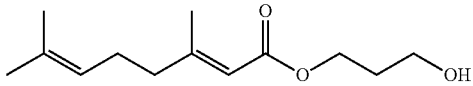 [SMILES: CC(C)=CCC/C(C)=C/C(=O)OCCCO] |
| 2144 2-Hydroxypropyl citronellate | 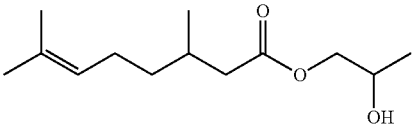 [SMILES: CC(C)=CCCC(C)CC(=O)OCC(C)O] |
| 2145 3-Hydroxypropyl citronellate | 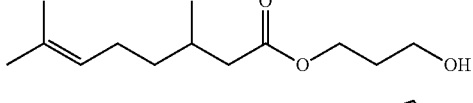 |
| 2166 Cyclopentyl citronellate | 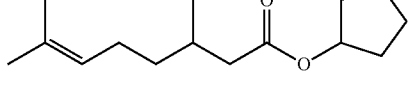 |
| 2167 tert-Butyl citronellate | 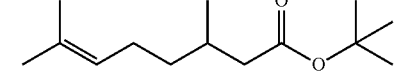 |
| 2168 Isoprenyl citronellate | 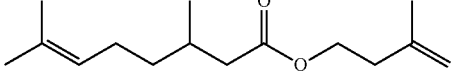 |
| 2169 Prenyl citronellate | 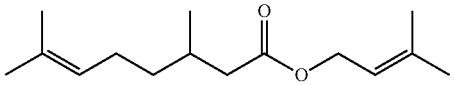 [SMILES: CC(C)=CCCC(C)CC(=O)OCC=C(C)C] |

TABLE 2-continued

Exemplary Compounds of Formula (B)

| Compound Name | Compound Structure |
|---|---|
| 2170 tert-Prenyl citronellate | 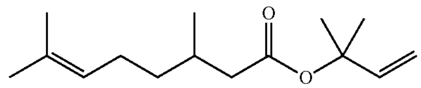 [SMILES: C=CC(C)(C)OC(=O)CC(C)CCC=C(C)C] |
| 2171 1,1-Dimethylpropargyl citronellate | 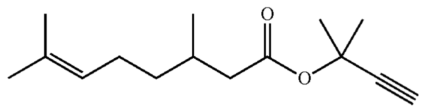 [SMILES: C#CC(C)(C)OC(=O)CC(C)CCC=C(C)C] |
| 2102 2-Hydroxyethyl geranate | 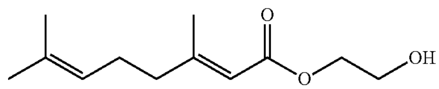 |
| 3070 (3-Methyloxetan-3-yl)methyl citronellate | 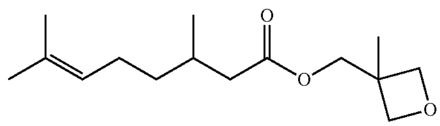 [SMILES: CC(C)=CCCC(C)CC(=O)OCC1(C)COC1] |
| 3071 3-Oxetanyl citronellate | 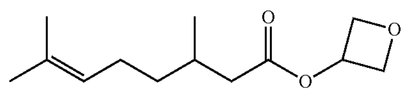 [SMILES: CC(C)=CCCC(C)CC(=O)OC1COC1] |
| 2-hydroxybut-1-yl citronellate | 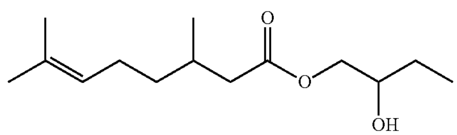 [SMILES: CCC(O)COC(=O)CC(C)CCC=C(C)C] |
| 2-hydroxybut-1-yl geranate | 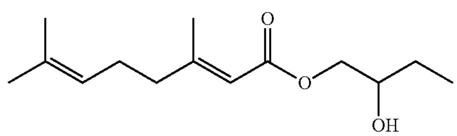 [SMILES: CCC(O)COC(=O)/C=C(\C)CCC=C(C)C] |
| 2-hydroxybut-1-yl cinnamate | 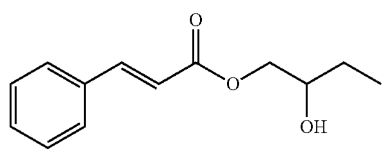 [SMILES: CCC(O)COC(=O)/C=C/c1ccccc1] |
| 3-hydroxybut-2-yl citronellate | 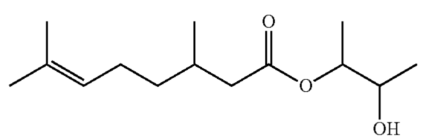 [SMILES: CC(C)=CCCC(C)CC(=O)OC(C)C(C)O] |
| 3-hydroxybut-2-yl geranate | 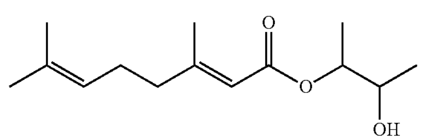 [SMILES: CC(C)=CCC/C(C)=C/C(=O)OC(C)C(C)O] |
| 3-hydroxybut-2-yl cinnamate | 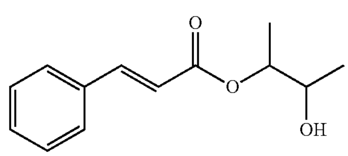 [SMILES: CC(O)C(C)OC(=O)/C=C/c1ccccc1] |
| 4-hydroxybut-1-yl citronellate | 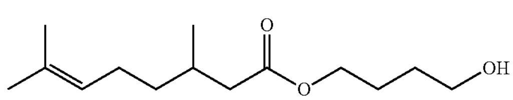 [SMILES: CC(C)=CCCC(C)CC(=O)OCCCCO] |

TABLE 2-continued

Exemplary Compounds of Formula (B)

| Compound Name | Compound Structure |
| --- | --- |
| 4-hydroxybut-1-yl geranate | 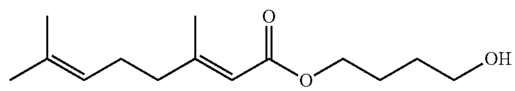 [SMILES: CC(C)=CCC/C(C)=C/C(=O)OCCCCO] |
| 4-hydroxybut-1-yl cinnamate | 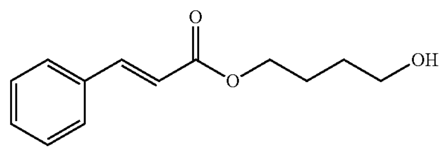 [SMILES: O=C(/C=C/c1ccccc1)OCCCCO] |
| (1-(hydroxymethyl)cyclopropyl)methyl citronellate | 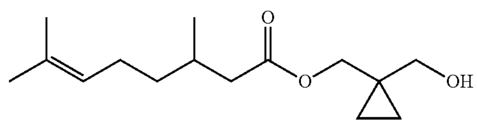 [SMILES: CC(C)=CCCC(C)CC(=O)OCC1(CO)CC1] |
| (1-(hydroxymethyl)cyclopropyl)methyl geranate | 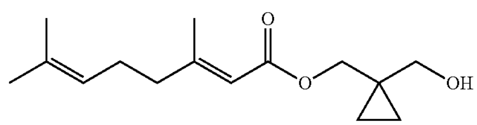 [SMILES: CC(C)=CCC/C(C)=C/C(=O)OCC1(CO)CC1] |
| (1-(hydroxymethyl)cyclopropyl)methyl cinnamate | 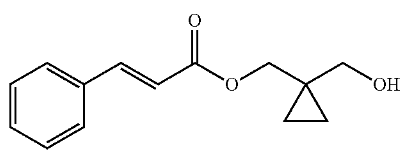 [SMILES: O=C(/C=C/c1ccccc1)OCC1(CO)CC1] |
| 3-hydroxy-2,2-dimethylpropyl citronellate | 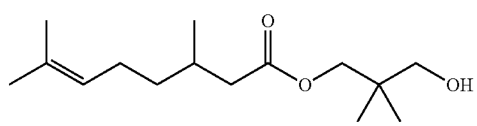 [SMILES: CC(C)=CCCC(C)CC(=O)OCC(C)(C)CO] |
| 3-hydroxy-2,2-dimethylpropyl geranate | 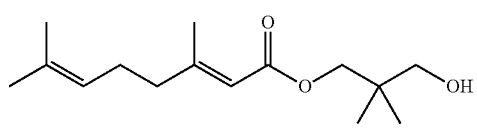 [SMILES: CC(C)=CCC/C(C)=C/C(=O)OCC(C)(C)CO] |
| 3-hydroxy-2,2-dimethylpropyl cinnamate | 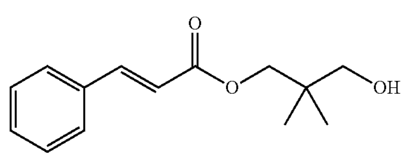 [SMILES: CC(C)(CO)COC(=O)/C=C/c1ccccc1] |
| 4-hydroxycyclohexyl citronellate | 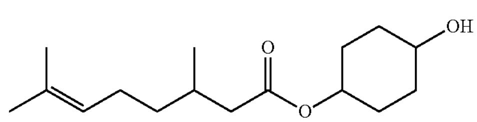 [SMILES: CC(C)=CCCC(C)CC(=O)OC1CCC(O)CC1] |
| 4-hydroxycyclohexyl geranate | 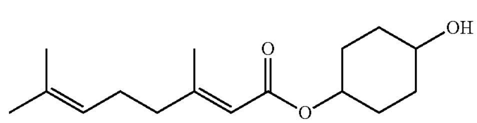 [SMILES: CC(C)=CCC/C(C)=C/C(=O)OC1CCC(O)CC1] |
| 4-hydroxycyclohexyl cinnamate | 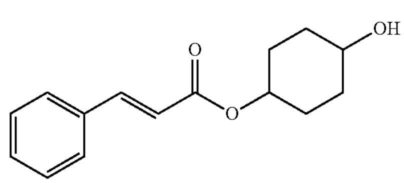 [SMILES: O=C(/C=C/c1ccccc1)OC1CCC(O)CC1] |

Another aspect of the present invention relates to a method of making a compound of formula (A). This method involves reacting (I) $R_1$—OH with $R_2$—COOH;
(II) $R_1$—OH with

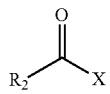

in the presence of a base; or
(III) $R_1$—OH with

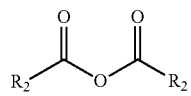

under conditions effective to form an ester having a structure of formula (A)

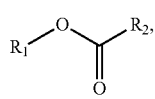

(A)

where
$R_1$ is a monoterpenoid or phenylpropanoid moiety;
$R_2$ is substituted or unsubstituted and is selected from the group consisting of H, $C_1$-$C_7$ unbranched or branched alkyl, $C_2$-$C_7$ unbranched or branched alkenyl, $C_3$-$C_7$ unbranched or branched alkynyl, $C_3$-$C_7$ unbranched or branched cycloalkyl, aryl, heteroaryl, —$(CH_2)_n$-heteroaryl, and $C_3$-$C_7$ unbranched or branched cycloalkenyl; and
n is an integer from 0-3; and
X is a halide.

Suitable bases for carrying out this aspect of the present invention (i.e., when reacting involves (II), or reacting $R_1$—OH with

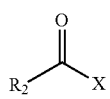

in the presence of a base) include, without limitation, triethylamine, pyridine, diisopropylethylamine, and 4-dimethylaminopyridine.

In one embodiment, said reacting is carried out in the presence of a catalyst or an acid catalyst. Suitable catalysts include, without limitation, 4-dimethylaminopyridine, sulfuric acid, phosphoric acid, p-toluenesulfonic acid, and polyphosphoric acid. In another embodiment, said reacting is carried out in the presence of an acid catalyst selected from the group consisting of sulfuric acid, phosphoric acid, p-toluenesulfonic acid, and polyphosphoric acid.

In yet another embodiment, said reacting is carried out in the presence of a coupling reagent and a catalyst. Suitable coupling reagents include, without limitation, N,N'-dicyclohexylcarbodiimide; N,N'-diisopropylcarbodiimide; and 1-ethyl-3-(3-dimethylaminopropyl)carbodiimide. According to one embodiment, the catalyst used with the coupling reagent is 4-dimethylaminopyridine.

Another aspect of the present invention relates to a method of making a compound of formula (B). This method involves reacting (I) $R_5$—COOH with $R_6$—OH;
(II)

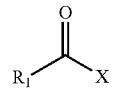

with $R_2$—OH in the presence of a base; or
(III)

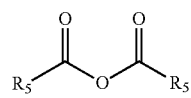

with $R_6$—OH;
under conditions effective to form an ester having a structure of Formula (B)

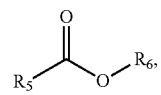

(B)

where
$R_5$ is a monoterpenoid or phenylpropanoid moiety and
$R_6$ is substituted or unsubstituted and is selected from the group consisting of $C_3$-$C_7$ unbranched or branched alkyl, $C_2$-$C_7$ unbranched or branched alkenyl, $C_3$-$C_7$ unbranched or branched alkynyl, $C_3$-$C_7$ unbranched or branched cycloalkyl, $C_3$-$C_7$ unbranched or branched cycloalkenyl, $C_3$-$C_7$ unbranched or branched heterocycle, $C_2$-$C_7$ saturated or unsaturated hydroxyalkyl, and —$(CR_{11}R_{12})_p$—O—$(CR_{11}R_{12})_q$—OH;
$R_{11}$ and $R_{12}$ are individually selected from H or $C_{1-6}$ alkyl;
p is an integer from 1 to 4;
q is an integer from 1 to 4; and
X is a halide.

Suitable bases for carrying out this aspect of the present invention (i.e., when reacting involves (II), or reacting

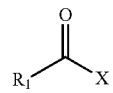

with $R_2$—OH
in the presence of a base) include, without limitation, triethylamine, pyridine, diisopropylethylamine, and 4-dimethylaminopyridine.

In one embodiment, said reacting is carried out in the presence of a catalyst or an acid catalyst. Suitable catalysts include, without limitation, 4-dimethylaminopyridine, sulfuric acid, phosphoric acid, p-toluenesulfonic acid, and polyphosphoric acid.

In another embodiment, said reacting is carried out in the presence of an acid catalyst. Suitable acid catalysts include, without limitation, sulfuric acid, phosphoric acid, p-toluenesulfonic acid, and polyphosphoric acid.

In yet another embodiment, said reacting is carried out in the presence of a coupling reagent and a catalyst. Suitable coupling reagents include, without limitation, N,N'-dicyclohexylcarbodiimide; N,N'-diisopropylcarbodiimide; and 1-ethyl-3-(3-dimethylaminopropyl)carbodiimide. According to one embodiment, the catalyst used with the coupling reagent is 4-dimethylaminopyridine.

As noted supra, the compounds of the present invention are derivatives of monoterpenoids or phenylpropanoids. By way of a non-limiting example, a compound of the present disclosure may be a derivative of an alcohol-containing monoterpenoid or phenylpropanoid, such as, e.g., thymol

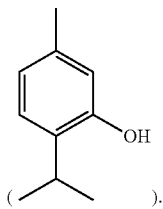

In the context of the present invention, a thymol-derivative has the structure

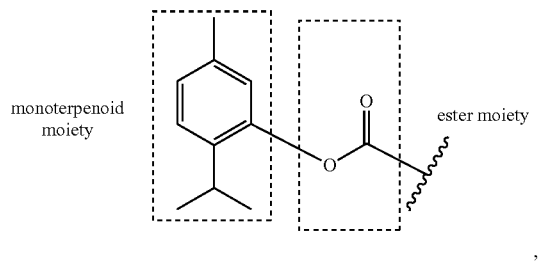 [SMILES: *C(=O)Oc1cc(C)ccc1C(C)C]

where the 10-carbon skeleton of thymol makes up the monoterpenoid or monoterpenoid moiety (e.g., $R_1$ of formula (A)), the alcohol of thymol makes up part of the ester moiety of the compound of the present invention, and the wavy line, $\prescript{}{}{}$, represents the linkage to the rest of the molecule (e.g., $R_2$ of formula (A)).

By way of another non-limiting example, a compound of the present invention may be a derivative of a carboxylic acid-containing monoterpenoid or phenylpropanoid, such as, e.g., citronellic acid

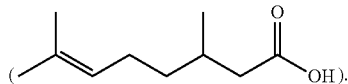

In the context of the present invention, a citronellic acid derivative has the structure

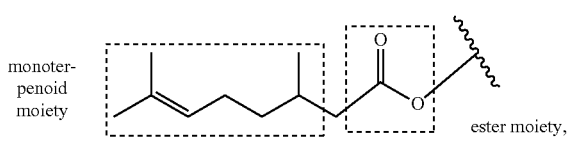 [SMILES: *OC(=O)CC(C)CCC=C(C)C]

where the 9-carbon skeleton of citronellic acid makes up the monoterpenoid or monoterpenoid moiety (e.g., $R_5$ of Formula (B)), the carboxylic acid of citronellic acid makes up the ester moiety of the compound, and the wavy line, $\prescript{}{}{}$, represents the linkage to the rest of the molecule (e.g., $R_6$ of Formula (B)). Thus, the ester direction (i.e., whether the carbonyl-carbon of the ester is bonded to the monoterpenoid moiety or the oxygen of the ester is bonded to the monoterpenoid moiety) is dictated by the monoterpenoid or phenylpropanoid precursor (e.g., thymol or citronellic acid) used herein.

Thus, the compounds of the present invention may be derived from monoterpenoid alcohols (i.e., monoterpenoids containing a hydroxyl group) or from monoterpenoid carboxylic acids (i.e., monoterpenoids containing a carboxylic acid). Alternatively, the compounds of the present invention may be derived from phenylpropanoid alcohols (i.e., phenylpropanoids containing a hydroxyl group) or from phenylpropanoid carboxylic acids (i.e., phenylpropanoids containing a carboxylic acid).

In one embodiment, the compounds of the present invention are derived from monoterpenoid alcohols (i.e., monoterpenoids containing a hydroxyl group). For example, the compound may be derived from an acyclic, unsaturated monoterpenoid alcohol selected from, e.g. and without limitation, citronellol, linalool, genaniol, nerol, and lavandulol. In another non-limiting example, the compound is derived from a cyclic or bicyclic unsaturated monoterpenoid alcohol selected from, e.g., carveol, pinocarveol, myrcenol, myrtenol, α-terpinol, 4-terpinol, verbenol, and perrilyl alcohol. In another non-limiting example, the compound is derived from a cyclic or polycyclic saturated monoterpenoid alcohol selected from, e.g., menthol, fenchol, borneol, isoborneol, and myrtenol. In yet another non-limiting example, the compound is derived from an isopropyl cresol selected from, e.g., thymol, carvacrol, and 4-isopropyl-3-methylphenol. In still another non-limiting example, the compound is derived from a cycloheptatrieneolone, such as any of the isomeric thujaplicins.

In another embodiment, the compounds of the present invention are derived from phenylpropanoid alcohols (i.e., phenylpropanoids containing a hydroxyl group). In one non-limiting example, the compound is derived from eugenol, isoeugenol, cinnamyl alcohol, coniferyl alcohol, zingerone, umbelliferone, coumaryl alcohol, and chavicol. In another non-limiting example, the compound is derived from an alcohol or phenol produced by the natural plant metabolism of a phenylpropanoid, including vanillin, ethylvanillin, piperonyl alcohol, and syringaldehyde.

In yet another embodiment, the compounds of the present invention are derived from phenylpropanoid carboxylic acids (i.e., phenylpropanoids containing a hydroxyl group). In one non-limiting example, the compound is derived from a substituted cinnamic acid. In another non-limiting example, the compound is derived from a carboxylic acid produced by the oxidation of a naturally occurring benzyl alcohol or benzaldehyde, where the benzaldehyde or benzyl alcohol is produced by metabolism of phenylpropanoids. In another non-limiting example, the compound is derived from 4-hydroxy-3-methoxybenzoic acid; 3,4-dimethoxybenzoic acid; or 3,4,5-trimethoxybenzoic acid. In another non-limiting example, the compound is derived from a non-alcoholic terpenoid by means of oxidation of said non-alcoholic terpenoid, including camphenic acid.

In still another embodiment, the compounds of the present invention are derived from monoterpenoid carboxylic acids (i.e., monoterpenoids containing a carboxylic acid), or the carboxylic acids derived by oxidation of monoterpenoid primary alcohol to the respective carboxylic acid. In one non-limiting example, the compound is derived from an acyclic monoterpenoid carboxylic acid, including citronellic acid, geranic acid, and nerolic acid. In another non-limiting example, the compound is derived from a mono- or bicyclic monoterpenoid carboxylic acid, including perillic acid, cinnamic acid and myrtenic acid.

The compounds of the present invention can be prepared from any known ester-forming chemistry. A person of ordinary skill in the art will appreciate that formate esters are also included in the context of the present invention. For example compounds of the present invention can be prepared from diols, including, without limitation, 2-hydroxybut-1-yl citronellate, 2-hydroxybut-1-yl geranate, 2-hydroxybut-1-yl cinnamate, 3-hydroxybut-2-yl citronellate, 3-hydroxybut-2-yl geranate, 3-hydroxybut-2-yl cinnamate, 4-hydroxybut-1-yl citronellate, 4-hydroxybut-1-yl geranate, 4-hydroxybut-1-yl cinnamate, (1-(hydroxymethyl)cyclopropyl)methyl citronellate, (1-(hydroxymethyl)cyclopropyl) methyl geranate, (1-(hydroxymethyl)cyclopropyl)methyl cinnamate, 3-hydroxy-2,2-dimethylpropyl citronellate, 3-hydroxy-2,2-dimethylpropyl geranate, 3-hydroxy-2,2-dimethylpropyl cinnamate, 4-hydroxycyclohexyl citronellate, 4-hydroxycyclohexyl geranate, and 4-hydroxycyclohexyl cinnamate.

In one embodiment, the compounds of the present invention are in a substantially pure form.

In another embodiment, the compounds of the present invention may be a single enantiomer or diastereomer or a racemic or diastereomeric mixture.

The compounds of the present invention can be used in undiluted or diluted form and can be converted into formulations or compositions customary for repellents. They can be used in all the presentation forms customary in cosmetics, including, without limitation, in the form of solutions, emulsions, gels, ointments, pastes, creams, powders, sticks, sprays, aerosols, and fumigants.

Thus, another aspect of the present invention relates to a composition (or formulation) comprising a compound of the present invention (as described supra) and a carrier.

For use in the non-cosmetic sector, the compounds can be incorporated, for example, into granules, oily spraying agents, or slow release formulations. Such formulations are prepared in a known manner by mixing or diluting the compounds of the present invention with solvents (e.g., xylene, chlorobenzenes, paraffins, methanol, ethanol, isopropanol, or water), carriers (e.g., kaolins, aluminas, talc, chalk, highly disperse silicic acid and silicates, nanoclays), emulsifying agents (e.g., polyoxyethylene fatty acid esters, polyoxyethylene fatty alcohol ethers, alkylsulphonates and arylsulphonates), and dispersing agents (e.g., lignin, sulphite waste liquors and methylcellulose), any of which are considered "carriers" for purposes of the compositions of the present invention.

The compounds of the present invention can be mixed with one another in the formulations to form the compositions or can also be used as mixtures with other known active compounds (e.g., sunscreen agents). The compositions in general contain between about 0.1 and about 95% (e.g., 0.1-95%) by weight of active compound, or between about 0.5 and about 90% (e.g., 0.5-90%).

In one embodiment, the composition is in the form of a lotion, spray, or cream. In another embodiment, the composition further includes a fragrance, perfume, or cologne.

In one embodiment, the composition of the present invention is formulated to be administered by topical application to the skin (i.e., keratinous tissue). Accordingly, the composition preferably has good aesthetic properties and will not cause any safety or toxicity concerns.

The carrier used in this and other compositions of the present invention can be in a wide variety of forms, including emulsion carriers, such as oil-in-water, water-in-oil, and oil-in-water-in-silicone emulsions, creams, ointments, ophthalmic ointments, aqueous solution, lotions, gels, or aerosols. As will be understood by the skilled artisan, a given component will distribute primarily into either the water or oil/silicone phase, depending upon the water solubility/dispersibility of the component in question. A safe and effective amount of carrier is from about 50% to about 99.99%, from about 80% to about 99.99%, from about 90% to about 98%, or from about 90% to about 95% of the composition.

Emulsions generally contain an effective amount of a compound of the present invention and a lipid or oil. Lipids and oils may be derived from animals, plants, or petroleum, and can be natural or synthetic. Emulsions may also contain a humectant such as glycerin. Emulsions may further contain from about 1% to about 10% or from about 2% to about 5%, of an emulsifier, based on the weight of the carriers. Emulsifiers may be ionic, anionic, or cationic. The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending upon the product form. Exemplary low viscosity emulsions have a viscosity of about 50 centistokes or less, about 10 centistokes or less, or about 5 centistokes or less. The emulsion may also contain anti-foaming agents to minimize foaming upon application to the skin.

Other carriers include oil-in-water emulsions having a continuous aqueous phase and a hydrophobic, water-insoluble phase dispersed therein. Preferred oil-in-water emulsions comprise from about 25% to about 98%, from about 65% to about 95%, or from about 70% to about 90% water by weight of the carrier.

The hydrophobic phase is dispersed in the continuous aqueous phase. The hydrophobic phase may contain water insoluble or partially soluble materials such as are known in the art including, but not limited to, silicones. The compositions of the present invention include, but are not limited to, lotions and creams, and may comprise a dermatologically acceptable emollient. As used herein, "emollient" refers to a material useful for preventing or relieving dryness, as well as for protecting the skin. A wide variety of suitable emollients is known and any may be used with the compositions of the present invention. Numerous examples of materials suitable for use as an emollient are provided in Sagarin, *Cosmetics, Science, and Technology* 2nd Edition Vol. 1, pp 3243 (1972), which is hereby incorporated by reference in its entirety. One specific emollient is glycerin. Glycerin may be used in an amount of from about 0.001% to about 20%, from about 0.01% to about 10%, or from about 0.1% to about 5% w/w of the total composition.

Lotions and creams generally comprise a solution carrier system and one or more emollients. Lotions typically comprise from about 1% to about 20% or from about 5% to about 20% of emollient; from about 50% to about 90% or from about 60% to about 80% water; and an effective amount of a compound of the present invention.

Ointments may comprise a simple carrier base of animal or vegetable oil or semi-solid water soluble carriers. Ointments may further comprise a thickening agent and/or an emollient. For example, an ointment may comprise from about 2% to about 20% of an emollient, about 0.1 to about 2% of a thickening agent, and an effective amount of a compound of the present invention.

Compositions according to the present invention may also include optional components, which should be suitable for application to keratinous tissue, i.e., when incorporated into the composition they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the present invention. The CTFA Cosmetic Ingredient Handbook, Second Edition (1992) (which is hereby incorporated by reference in its entirety), describes a wide variety of non-limiting cosmetic and pharmaceutical ingredients commonly used in the skin care industry, which are suitable for use in the compositions of the present invention. Examples of these ingredient classes include abrasives, absorbents, aesthetic components such as fragrances, pigments, colorings, essential oils, skin sensates, astringents (e.g., clove oil, menthol, camphor, eucalyptus oil, eugenol, menthyl lactate, hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents cosmetic biocides, denaturants, drug astringents, external analgesics, film formers or materials such as polymers for aiding the film-forming properties and substantivity of the composition (e.g., copolymer of eicosene and vinyl pyrrolidone), opacifying agents, pH adjusters, propellants, reducing agents, sequestrants and/or healing agents (e.g., panthenol and derivatives such as ethyl panthenol), aloe vera, pantothenic acid and its derivatives, allantoin, and bisabolol), skin treating agents, thickeners, and vitamins and derivatives thereof.

The compounds of the present invention repel insects.

With respect to the compositions containing the compounds of the present invention, the appropriate dose regimen, the amount of each dose administered, and specific intervals between doses of the active compound may depend upon the particular active compound employed, the age and condition of the subject to which the compositions is administered (if, in fact, it is intended to be administered, e.g., as a topical application to a subject), and the desired repellent effect.

As one skilled in the art will readily appreciate, the compounds of the present invention can be used alone or in combination with one another, as well as in combination with the other insect repellents (e.g., those currently commercially available, some of which are described herein).

The compositions of the present invention may be useful for cosmetic purposes. Cosmetic applications include the topical application of compositions containing one or more compounds of the present invention.

An effective dosage and treatment protocol can be determined by conventional means, starting with a low dose in laboratory animals, and then increasing the dosage while monitoring the effects, and systematically varying the dosage regimen as well.

Compositions of the present invention may be administered by topical application. For topical administration, the compounds of the present invention can be formulated as a foam or mousse, solution, gel, lotion, ointment, cream, suspension, paste, liniment, powder, tincture, aerosol, transdermal drug delivery system, or the like, in a pharmaceutically or cosmetically acceptable form by methods well known in the art. The composition can be in any variety of forms common in the pharmaceutical or domestic arts for topical application to animals or humans, including solutions lotions, sprays, creams, ointments, salves, gels, aerosols, etc., as set forth above. Preferred agents are those that are viscous enough to remain on the treated area, those that do not readily evaporate, and/or those that are easily removed by rinsing with water topically with the aid of soaps, cleansers, and/or shampoos. Actual methods for preparing topical formulations are known or apparent to those skilled in the art.

The compounds of the present invention are less volatile than naturally occurring monoterpenoids, and more closely match the volatility and MW of sesquiterpenoids, meaning a compound having a 15-carbon scaffold with non-linear branches. The term is often used loosely to refer collectively to sesquiterpenoid derivatives as well as sesquiterpenoid analogs. Sesquiterpenoids can include sesquiterpenes, alcohols, ketones, aldehydes, ethers, acids, hydrocarbons without an oxygen functional group, and so forth.

For protection from arthropods such as blood-sucking insects or mites, the compounds and/or compositions of the present invention are generally either applied to human or animal skin, or items of clothing and other objects are treated with the compounds. The compounds may be dispensed into the environment (e.g., outdoors or indoors) in vapor form (e.g., an aerosol).

The compounds of the present invention, when combined with a suitable carrier or vehicle, are useful as insect repellents. Target areas for such use include, without limitation, people, pets, livestock, cupboards, containers, houses, yards, gardens, and so forth. Thus, target areas can include inanimate objects in the vicinity of a target area, including but not limited to, plants, articles of clothing, premises, tents, pillows, bed nets, blankets, automobiles, etc.

The repellents can be used against a variety of target pests including, without limitation, blood-sucking insects, biting insects, cockroaches, mosquitoes, blackfly, fleas, house flies, barn fly, face fly, bush fly, deer fly, horse fly, gnats, beetle, beer bug, louse, bed bug, earwig, ant, aphid, spruce bud worm, corn borer, sand flea, tsetse fly, assassin bug, biting flies, sand fly, stored grain pests (e.g., maize weevil, red flour beetle, saw-toothed grain beetle, Indian meal moth), clothes moths, ticks, mites, spiders, phytophagous pests, hematophagous pests, and other arthropod pests.

Different formulations or routes of exposure can provide for even further uses. For example, in addition to exposing the target pest to the repellent by contact, and possibly aquatic exposure, any of these novel repellents can also be used as fumigants. Useful amounts to evoke repellency ("repellent" amounts) will depend on the particular application technique used and on the specific conditions in the area at the time of application. Such amounts can readily be determined by those skilled in the art.

Accordingly, another aspect of the present invention relates to a method of repelling a pest. This method involves applying a composition comprising a compound of formula (A) as follows:

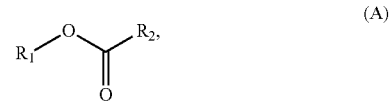

(A)

wherein
R₁ is a monoterpenoid or phenylpropanoid moiety;
R₂ is substituted or unsubstituted and is selected from the group consisting of H, $C_1$-$C_7$ unbranched or branched alkyl, $C_2$-$C_7$ unbranched or branched alkenyl, $C_3$-$C_7$ unbranched or branched alkynyl, $C_3$-$C_7$ unbranched or branched cycloalkyl, aryl, heteroaryl, —$(CH_2)_n$-heteroaryl, and $C_3$-$C_7$ unbranched or branched cycloalkenyl; and
n is an integer from 0-3, with the proviso that when R₁ is a monoterpenoid moiety R₂ is not a tert-butyl group or
a compound of formula (B) as follows:

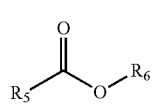

(B)

wherein
R₅ is a monoterpenoid or phenylpropanoid moiety and
R₆ is substituted or unsubstituted and is selected from the group consisting of $C_3$-$C_7$ unbranched or branched alkyl, $C_2$-$C_7$ unbranched or branched alkenyl, $C_3$-$C_7$ unbranched or branched alkynyl, $C_3$-$C_7$ unbranched or branched cycloalkyl, $C_3$-$C_7$ unbranched or branched cycloalkenyl, $C_3$-$C_7$ unbranched or branched heterocycle, $C_2$-$C_7$ saturated or unsaturated hydroxyalkyl, and —$(CR_{11}R_{12})_p$—O—$(CR_{11}R_{12})_q$—OH;
$R_{11}$ and $R_{12}$ are individually selected from H or $C_{1-6}$ alkyl;
p is an integer from 1 to 4; and
q is an integer from 1 to 4 to a target area under conditions effective to repel a pest.

In one embodiment, the composition is applied by a vapor delivery system. This refers to vapor delivery systems that are based on passive flow control nozzles that utilize permeable polymeric membranes. There are two primary preferred systems or approaches: (i) fixed supply, stand-alone units and (ii) replenished, distributed systems (such as replenished by gravity or by pumps). The vapor delivery system with a fixed supply is used to deliver volatile compounds in either open local environments or open field environments. On the other hand, the pumped delivery system with a piped supply distribution header is uniquely suited for applications in open field environments. These systems are classified as passive systems since the vapor that results from volatilization at the membrane surface is dispensed by stagnant diffusion and/or random air circulation over the flow control nozzles. The pump is used to move the volatile compound from a storage reservoir to the passive flow control nozzles.

It has been determined that chemoreceptors responsible for repellent response are present on the antennae and other chemosensory organs of mosquitoes and various other arthropod pest species. Moreover, it has been demonstrated that monoterpenoids are capable of activating various chemosensory sensilla on the antennae of various pest species. By decreasing the volatility of the repellent compounds of the present invention by means of increasing the molecular weight or polarity of these relatively volatile compounds by synthetic chemistry processes, there is a higher potential for the repellent chemical to remain on surfaces for longer and function as an insect repellent for longer. The novel compounds of the present invention can effectively repel pests from a specific target area for longer periods of time than the highly volatile, repellent monoterpenoid compounds they are synthetically derived from.

In carrying out this method of the present invention, the term "applying" as used herein includes any suitable method of emitting an effective repellent amount of a plant volatile compound in a target area. The term "target area" as used herein includes any place where the presence of target pests is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth. Target area can also include the outer covering of a living being, such as skin, fur, hair, or clothing.

"Applying" includes broadcast or restricted localized spraying of a volatile in or around an area, with or without first micro-encapsulating the volatile, emitting the volatile from one or more controlled-release point-source dispensers in or around an area, and integrating the release of the volatile with an irrigation technique (chemigation). "Applying" can also refer to emitting liquid or solid repellents through use of creams, liquid-based products, powders, and so forth.

A controlled-release point-source dispenser is one type of delivery means for a composition comprising the repellent compound of the present invention and a carrier. Such a dispenser includes any suitable device and method for controlling the emission rate of the volatile compound from a concentrated source reservoir of the compounds. For example, and without limitation, suitable dispensers include pads, beads, rods, spirals, or balls comprised of rubber, leather, cotton, wood or wood products, polyethylene, polypropylene or polyvinyl chloride that are impregnated with the volatile compound; micro-capillary tubes open at one end; sealed polyethylene or polypropylene tubes sealed at both ends; laminates comprised of layers of the volatile compound alternated with plastic and cut in various sized flakes or preserved as large ribbons or sheets; permeable or semi-permeable membranes covering a non-permeable container serving as a reservoir for the volatile compounds; large porous beads or sponges; micro-capsules; sealed envelopes or bags made of polyethylene, polypropylene, paper, cardboard, or other permeable substances, metered aerosol systems utilizing pump or pressure technologies to emit aerosolized droplets of the volatiles into the atmosphere, onto plants surfaces or soil, or onto any of the above controlled-release point-source dispensers; and non-aerosol micro-pump technologies that cause metered quantities of the compounds to be dispensed and volatilized by any of the above methods.

A fumigant may also be used in carrying out this aspect of the present invention. A "fumigant" as used herein refers to the use of a gas repellent, or a volatile solid or liquid repellent to control pests in storage bins, buildings, ships, rail cars, stored products, organic materials such as soil, foods, animal feed, compost, and so forth, living organisms such as plants, or in any closed areas, i.e., target areas, which are prone to having pests, i.e., pest infestation.

As used herein, the term "repel" means that less time is spent by the pest in a given area, i.e., a target area containing a repellent, than in an available non-target or untreated area (i.e., an area with no repellent). "Repel" can also mean that no time is spent by the pest in the target area. As such, "repelling" a pest includes deterring a pest from remaining in a target area, as well as keeping a pest away from a target area. In some instances, "repel" may include killing a target pest. In some instances, a pest may be "slowed" in behavior and responsiveness after coming in contact with a repellent, such that the presence of the target pest is less of a nuisance to a human or animal in the target area. Slowing a target pest may also allow it to be killed by other means. The total number of pests in an area may be considered to be suppressed or even eliminated due to the repellent compound of the present invention. By "suppressed" it is meant to reduce or limit the incidence or severity of a pest infestation or pest activity, even if for a limited period of time.

EXAMPLES

The following examples are provided to illustrate embodiments of the present invention but they are by no means intended to limit its scope.

Example 1—General Synthesis

Small Scale

Limiting reagent was chosen based on ease of removal of reagent used in excess, and the expense of the starting materials. Between 5 and 20 mmol of the limiting reagent was dissolved in dichloromethane or methylene chloride to a molarity of between 0.1 and 5 M. Between 1.05 and 10 eq. of the excess reagent was dissolved into the solution, and then 0.05 to 0.25 eq. 4-dimethylaminopyridine (DMAP) was added. The reaction was cooled, typically to 0° C., and then dicyclohexylcarbodiimide (DCC) (1.05 to 4 eq) was added, typically as a solution in dichloromethane or chloroform, but sometimes as the neat solid or melted liquid, and the reaction was stirred at 0° C. for at least 5 minutes and sometimes up to three hours. The reaction was then warmed to room temperature and stirred for 1 to 24 hours. The reaction was diluted with hexanes, and filtered to remove dicyclohexylurea (DCU). The crude material was concentrated under vacuum, and purified by column chromatography, distillation, or recrystallization.

Geranyl Cyclopropanecarboxylate

In a 125 mL Erlenmyer flask, geraniol (0.771 g, 5 mmol), 4-dimethylaminopyridine (DMAP) (61 mg, 0.5 mmol), and dicyclohexylcarbodiimide (DCC) (1.08 g, 1.05 eq.) were dissolved in chloroform (20 mL) and the solution was cooled to 0° C. open to air. Cyclopropanecarboxylic acid (0.516 g, 6 mmol) was then added by syringe over 5 minutes, and the reaction was then allowed to warm to room temperature, at which point a white precipitate of dicyclohexylurea (DCU) formed, and stirring was continued for 4 hours. Hexane (50 mL) was then added, and the reaction was cooled to 0° C., and the DCU was removed by filtration. The organic solution was then washed once with 1M HCl, twice with saturated aqueous $NaHCO_3$, and once with brine, and was dried over anhydrous sodium sulfate. Solvent was removed under reduced pressure, and the crude product was purified by column chromatography. Colorless oil (0.716 g, 65%). $^1$HNMR (400 MHz, $CDCl_3$) δ 5.34 (t, 1H), 5.08 (t, 1H), 4.59 (d, 2H), 2.14-2.03 (mult, 4H), 1.70 (s, 3H), 1.68 (s, 3H), 1.63-1.58 (mult, 1H), 1.59 (t, 3H), 1.00-0.97 (mult, 2H), 0.87-0.82 (mult, 2H). $^{13}$CNMR (101 MHz, $CDCl_3$) δ 175.1, 142.2, 132.0, 123.9, 118.5, 61.6, 39.7, 26.4, 25.8, 17.8, 16.6, 13.1, 8.5.

Perrilyl Isovalerate

Same procedure as above, using perrilyl alcohol and isovaleric acid. Colorless oil (1.15 g, 97%). $^1$HNMR (400 MHz, $CDCl_3$) δ 5.77-5.73 (mult, 1H), 4.74-4.71 (mult, 1H), 4.71-4.69 (mult, 1H), 4.50-4.42 (mult, 2H), 2.20 (d, 2H), 2.19-2.04 (mult, 5H), 2.02-1.92 (mult, 1H), 1.88-1.81 (mult, 1H), 1.73 (s, 3H), 1.48 (ddt, 1H), 0.96 (d, 6H). $^{13}$CNMR (101 MHz, $CDCl_3$) δ 173.05, 149.57, 132.70, 125.69, 108.74, 77.32, 77.00, 76.68, 68.17, 43.47, 40.81, 30.44, 27.29, 26.40, 25.72, 22.41, 20.73.

Linalyl Isobutyrate

Same procedure as above, using linalool and isobutyric acid. Colorless oil. (0.381 g, 34%). 62% of starting linalool was also recovered during column chromatography (38% conversion; 89% yield of converted material). $^1$HNMR (400 MHz, $CDCl_3$) δ 5.95 (dd, 1H), 5.15 (dd, 1H), 5.05 (dd, 1H), 5.04 (dt, 1H), 2.49 (hept, 1H), 1.97 (q, 2H), 1.87 (ddd, 1H), 1.74 (ddd, 1H), 1.67 (s, 3H), 1.59 (s, 3H), 1.45 (d, 6H). $^{13}$CNMR (101 MHz, $CDCl_3$) δ 173.05, 149.57, 132.70, 125.69, 108.74, 77.32, 77.00, 76.68, 68.17, 43.47, 40.81, 30.44, 27.29, 26.40, 25.72, 22.41, 20.73.

Cyclobutylmethyl Cinnamate

Same procedure as above, using cyclobutanemethanol and cinnamic acid. Colorless oil (1.00 g, 93%). $^1$HNMR (400 MHz, 1:1 $CDCl_3$:DMSO-$d_6$) δ 6.85 (d, J=16.0 Hz, 1H), 6.81 (dd, 2H), 6.64-6.60 (mult, 3H), 5.72 (d, J=16.0 Hz, 1H), 3.35 (d, J=7 Hz, 2H), 1.89 (hept, 1H), 1.39-1.24 (m, 2H), 1.14 (dtd, 2H), 1.09-0.97 (m, 2H). $^{13}$CNMR (101 MHz, 1:1 $CDCl_3$:DMSO-$d_6$) δ 164.68, 142.61, 142.58, 132.44, 128.56, 127.16, 126.39, 116.45, 66.11, 32.22, 22.85, 16.51.

Carvacryl Formate

The above method with carvacrol and formic acid, performed on a 20 mmol scale, using 40 mmol 98% formic acid and 30 mmol DCC, and scaling solvents up by a factor of three. Chromatography (80/20 hexanes/ethyl acetate) yielded 3.26 g (91%) of a colorless oil. $^1$HNMR (400 MHz, $CDCl_3$) δ 8.32 (s, 1H), 7.18 (dd, J=7.8, 1.0 Hz, 1H), 7.06 (dd, J=7.8, 1.8 Hz, 1H), 6.91 (d, J=1.8 Hz, 1H), 2.89 (hept, J=6.9 Hz, 1H), 2.19 (s, 3H), 1.24 (d, J=6.9 Hz, 6H). $^{13}$CNMR (101 MHz, $CDCl_3$) δ 159.32, 148.42, 148.36, 131.14, 126.94, 124.61, 119.34, 77.02, 33.56, 23.88, 15.84.

2-Hydroxyethyl Citronellate

In 50 mL of toluene, dissolve ethylene glycol (2.98 g, 40 mmol), citronellic acid (1.70 g, 10 mmol), and p-toluenesulfonic acid (0.172 g, 1 mmol). The reaction was heated to reflux to allow water to be removed azeotropically and monitor reaction progress by TLC. Upon consumption of starting material, the reaction was cooled, 50 mL water was added, and layers were separated. The aqueous layer was extracted with ethyl acetate, and then organic layers were combined, washed with water twice, then with 1M sodium hydroxide. Dried over magnesium sulfate, solvent removed under pressure, and then purified by column chromatography. Colorless oil (1.57 g, 73%). $^1$HNMR (600 MHz, $CDCl_3$) δ 5.08 (ddq, J=8.7, 5.7, 1.5 Hz, 1H), 4.21 (ddd, J=5.8, 3.5, 1.0 Hz, 2H), 3.82 (ddd, J=4.5, 3.5, 1.0 Hz 2H), 2.36 (dd, J=14.8, 5.9 Hz, 1H), 2.16 (dd, J=14.8, 8.3 Hz, 1H), 2.06-1.91 (m, 4H), 1.67 (d, J=1.6 Hz, 3H), 1.59 (d, J=1.4 Hz, 3H), 1.35 (ddt, J=13.3, 9.4, 6.0 Hz, 1H), 1.23 (dddd, J=13.6, 9.4, 7.8, 6.0 Hz, 1H), 0.95 (d, J=6.7 Hz, 3H). $^{13}$CNMR (151 MHz, $CDCl_3$) δ 173.59, 131.62, 124.15, 65.83, 61.34, 41.62, 36.73, 29.99, 25.67, 25.36, 19.56, 17.62.

Primary and Secondary Alcohol and Phenol Esterification, Large Scale

Limiting reagent was chosen based on ease of removal of reagent used in excess, and the expense of the starting materials. Between 50 and 1000 mmol of the limiting reagent was mixed with between 1.05 and 10 equivalents of the reagent used in excess, and a solvent, typically benzene or toluene, was added to form a 0.1 to 5 M solution with respect to the limiting reagent. A catalyst, typically 0.005 to 0.05 equivalents of sulfuric acid or p-toluenesulfonic acid, was added, and the reaction is heated, often to reflux, to remove water. The reaction was monitored to determine completion of reaction, which often occurred after 0.5 to 12 hours. The reaction was cooled, and the reaction mixture was washed with water, and then 1M sodium hydroxide. The organic layer was dried, typically using magnesium sulfate or sodium sulfate, and then the solvent was removed under vacuum. The resulting compound was typically of sufficient purity for most applications, though it may also have been distilled under vacuum.

Tables 3.1-3.5 below provide compounds matrices of esters derived from monoterpenoid and phenylpropanoid alcohols.

TABLE 3.1

|  | Formate HCOOH | Isobutyrate iPrCOOH | Isovalerate iBuCOOH | Cyclopropane-carboxylate cPrCOOH | Cyclobutane-carboxylate cBuCOOH |
|---|---|---|---|---|---|
| Thymyl | 1107A | 1143 | 1055B | 1055A | 1142 |
| Carvacryl | 1107B | 2205 | 1079C | 1079A | 2202B |
| Eugenyl | 1146 | 1148 | 1076A | 1147 | 1149 |
| Vanillyl | 2001 | 2003 | 2005 | 2002 | 2004 |
| Umbelliferonyl |  | 2214 | 2215 | 2216 | 2217 |
| Cinnamyl |  | 2260 | 2254 | 2038 | 2039 |
| Citronellyl | 1089 | 2204 | 1034B | 1035A | 2025 |
| Geranyl |  | 2261A | 2255A | 2023A | 2024A |
| Neryl |  | 2261B | 2255B | 2023B | 2024B |
| Linalyl | 2153 | 2030 | 2152 | 2041 | 2151 |
| Menthyl | 2269 | 2262 | 2256 | 1033B | 2113 |
| α-Terpinyl |  | 2263 | 2257 | 2054 | 2099 |
| Carvyl | 2219 | 2220 | 2221 | 2222 | 2223 |
| Perillyl |  | 2034 | 2035 | 2032 | 2033 |
| Bornyl | 2127 | 2264A | 2126 | 2124 | 2125 |
| Isobornyl | 2131 | 2264B | 2130 | 2128 | 2129 |
| Fenchyl | 2123 | 2265 | 2122 | 2120 | 2121 |
| Myrtenyl |  | 2266 | 2258 | 2018 | 2201 |
| cis-Verbenyl |  | 2267 | 3014 | 2225 | 2226 |

TABLE 3.2

|  | Cyclo-pentane-carboxylate cPnCOOH | Cyclo-hexane-carboxylate cHexCOOH | Pivalate Me3CCOOH | Cyclo-propyl-acetate cPrCH2COOH | 1-Methyl-cyclobutane-carboxylate cBu(Me)COOH |
|---|---|---|---|---|---|
| Thymyl | 2094 | 2085 | 3015 | 2228 | 2104 |
| Carvacryl | 2282 | 2283 |  |  |  |
| Eugenyl |  |  |  |  |  |
| Vanillyl |  |  |  |  |  |
| Umbelliferonyl | 2218 |  |  |  |  |
| Cinnamyl |  |  |  |  |  |
| Citronellyl | 2119 | 2203 | 1036A | 2229 | 2106 |
| Geranyl | 2206A | 2207A |  |  |  |
| Neryl | 2206B | 2207B |  |  | 2108 |
| Linalyl |  |  |  |  |  |
| Menthyl | 2116 | 2117 | 3016 | 2230 | 2210 |
| α-Terpinyl |  |  |  |  |  |
| Carvyl | 2224 |  |  |  |  |
| Perillyl | 2115 | 2114 |  |  |  |
| Bornyl |  |  |  |  |  |
| Isobornyl |  |  |  |  |  |
| Fenchyl |  |  |  |  |  |
| Myrtenyl |  |  |  |  |  |
| cis-Verbenyl | 2227 |  |  |  |  |

TABLE 3.3

|  | 2,2-Di-methyl-cyclo-propane-carboxylate | trans-1,2-Dimethyl-cyclopropane-carboxylate | 1-Allyl-cyclo-butane-carboxylate cBu(CH2CH=CH2)COOH | 1-Allyl-cyclopropane-carboxylate cPr(CH2CH=CH2)COOH | 1-Methyl-cyclopropane-carboxylate cPr(Me)COOH |
|---|---|---|---|---|---|
| Thymyl | 3020 | 3023 | 3029 | 3032 | 3035 |
| Carvacryl |  |  |  |  |  |
| Eugenyl |  |  |  |  |  |
| Vanillyl |  |  |  |  |  |
| Umbelliferonyl |  |  |  |  |  |
| Cinnamyl |  |  |  |  |  |
| Citronellyl | 3021 | 3024 | 3030 | 3033 | 3036 |
| Geranyl |  |  |  |  |  |
| Neryl |  |  |  |  |  |
| Linalyl |  |  |  |  |  |

TABLE 3.3-continued

|  | 2,2-Di-methyl-cyclo-propane-carboxylate | trans-1,2-Dimethyl-cyclopropane-carboxylate | 1-Allyl-cyclo-butane-carboxylate cBu(CH$_2$CH=CH$_2$)COOH | 1-Allyl-cyclopropane-carboxylate cPr(CH$_2$CH=CH$_2$)COOH | 1-Methyl-cyclopropane-carboxylate cPr(Me)COOH |
|---|---|---|---|---|---|
| Menthyl | 3022 | 3025 | 3031 | 3034 | 3037 |
| α-Terpinyl |  |  |  |  |  |
| Carvyl |  |  |  |  |  |
| Perillyl |  |  |  |  |  |
| Bornyl |  |  |  |  |  |
| Isobornyl |  |  |  |  |  |
| Fenchyl |  |  |  |  |  |
| Myrtenyl |  |  |  |  |  |
| cis-Verbenyl |  |  |  |  |  |

TABLE 3.4

|  | 2-Furoate (C4H3O)COOH | 2-Thiophene-carboxylate (C4H3S)COOH | Thiophen-2-ylacetate (C4H3S)CH2COOH | Benzoate PhCOOH |
|---|---|---|---|---|
| Thymyl | 2188 | 2182 | 2243 | 2191 |
| Carvacryl |  |  |  |  |
| Eugenyl |  |  |  |  |
| Vanillyl |  |  |  |  |
| Umbelliferonyl |  |  |  |  |
| Cinnamyl |  |  |  |  |
| Citronellyl | 2186 | 2180 | 2244 | 2189 |
| Geranyl |  |  |  |  |
| Neryl |  |  |  |  |
| Linalyl |  |  |  |  |
| Menthyl | 2187 | 2181 | 2245 | 2190 |
| α-Terpinyl |  |  |  |  |
| Carvyl |  |  |  |  |
| Perillyl |  |  |  |  |
| Bornyl |  |  |  |  |
| Isobornyl |  |  |  |  |
| Fenchyl |  |  |  |  |
| Myrtenyl |  |  |  |  |
| cis-Verbenyl |  |  |  |  |

TABLE 3.5

|  | 3,3-Dimethyl-acrylate Me2C=CHCOOH | Tiglate MeCH=CMeCOOH | Levulinate MeCOCH2CH2COOH |
|---|---|---|---|
| Thymyl | 2103 | 2179 | 2185 |
| Carvacryl |  |  |  |
| Eugenyl |  |  |  |
| Vanillyl |  |  |  |
| Umbelliferonyl |  |  |  |
| Cinnamyl |  |  |  |
| Citronellyl | 2105 | 2177 | 2183 |
| Geranyl |  |  |  |
| Neryl | 2107 |  |  |
| Linalyl |  |  |  |
| Menthyl | 2118 | 2178 | 2184 |
| α-Terpinyl |  |  |  |
| Carvyl |  |  |  |
| Perillyl |  |  |  |
| Bornyl |  |  |  |
| Isobornyl |  |  |  |
| Fenchyl |  |  |  |
| Myrtenyl |  |  |  |
| cis-Verbenyl |  |  |  |

Tables 4.1-4.3 below provide compound matrices of esters derived from monoterpenoid and phenylpropanoid carboxylic acids.

TABLE 4.1

|  | Cyclopropyl-methyl | Cyclobutyl-methyl | Cyclopentyl |
|---|---|---|---|
| Citronellate | 2027 | 2026 | 2166 |
| Geranate | 2020 |  |  |
| Cinnamate | 2036 | 2037 |  |

TABLE 4.2

|  | tert-Butyl | 2-hydroxy-ethyl | 2-Hydroxy-propyl |
|---|---|---|---|
| Citronellate | 2167 | 2155 | 2144 |
| Geranate |  | 2102 | 2142 |
| Cinnamate |  | 1092A | 2140 |

TABLE 4.3

|  | 3-Hydroxy-propyl | Isoprenyl | Prenyl | tert-Prenyl | 1,1-Dimethyl-propargyl |
|---|---|---|---|---|---|
| Citronellate | 2145 | 2168 | 2169 | 2170 | 2171 |
| Geranate | 2143 |  |  |  |  |
| Cinnamate | 2141 |  |  |  |  |

Example 2—Short-Term Spatial Repellency

Materials and Methods

Mosquitoes

Northern house mosquitoes (*Culex pipiens*), a primary carrier of West Nile virus in eastern North America, were obtained from an established colony in the Medical Entomology Laboratory in the Department of Entomology at Iowa State University of Science and Technology, Ames Iowa. Mosquito rearing was performed by established protocols that are maintained by the Medical Entomology Laboratory. Repellency bioassays were performed with adult female mosquitoes that emerged 5-7 days previously. After emergence and prior to testing, adult mosquitoes were supplied with a piece of cotton that was soaked in a 10% sucrose solution ad libitum; the mosquitoes tested did not receive a blood meal and were starved for several hours before testing. Mosquitoes, prior to testing, were held at 27° C., 80% relative humidity, and on a 16:8 hr light:dark photoperiod.

Procedure

Repellency bioassays were performed using a static air repellency chamber, which has been described in various publications by the Pesticide Toxicology Laboratory at Iowa State University of Science and Technology, Ames, Iowa Briefly, a 9-cm×60-cm glass tube was used to monitor the distribution of mosquitoes at 15 min, 30 min, 60 min, 90 min, 120 min, and 150 min after introducing mosquitoes into the static air repellency chamber. Filter papers were treated with 1 mL of 0.5% solution in acetone of the terpenoid analogs created in the lab and let air dry for 15 minutes before they were introduced into the spatial chamber for testing. One end of the spatial chamber contained a treated filter paper, whereas the other (untreated) end of the spatial chamber was not treated with compound. Controls contained filter papers treated with acetone, the solvent used to make the 0.5% solutions. Each end of the repellency chamber was secured with a 100-mm Petri dish using celluloid tape. After securing the petri dishes with corresponding treated or untreated filter papers to the spatial chamber, mosquitoes were anesthetized with carbon dioxide, and approximately 20 female mosquitoes were placed into each repellency chamber for one replicate. The opening of the spatial repellency chamber was secured with celluloid tape to prevent their escape. Chambers were oriented in opposite directions from the previous replicate to account for any directional effect. Four replicates were performed for data analysis for both the control and treatment groups.

Repellency Data Analysis

Data for spatial repellency, the percentage repellency, is reported at each of the respective time points in the figures and tables mentioned below. The percentage spatial repellency is the examination of the distribution of mosquitoes and is calculated using the following equation:

$$\text{Percentage Repellency} = \frac{(\text{\# of mosquitoes in untreated half}) - (\text{\# of mosquitoes in treated half})}{(\text{total \# of mosquitoes})} \times 100$$

Results

Short-Term Repellency Assay

The mean percentage repellency for each time point caused by the introduction of a filter paper treated with 1 mL of acetone alone (control) is illustrated in FIG. 1. The percentage repellency caused by this treatment is approximately 8.6% at 15 minutes after the introduction of mosquitoes into the chamber. This is the maximum percentage repellency achieved by this treatment. However, it is not statistically significant from 0 (no repellent effect). The absence of statistically significant repellency values for all time points is representative for the solvent control treatment in this experimental system.

Figure 2:
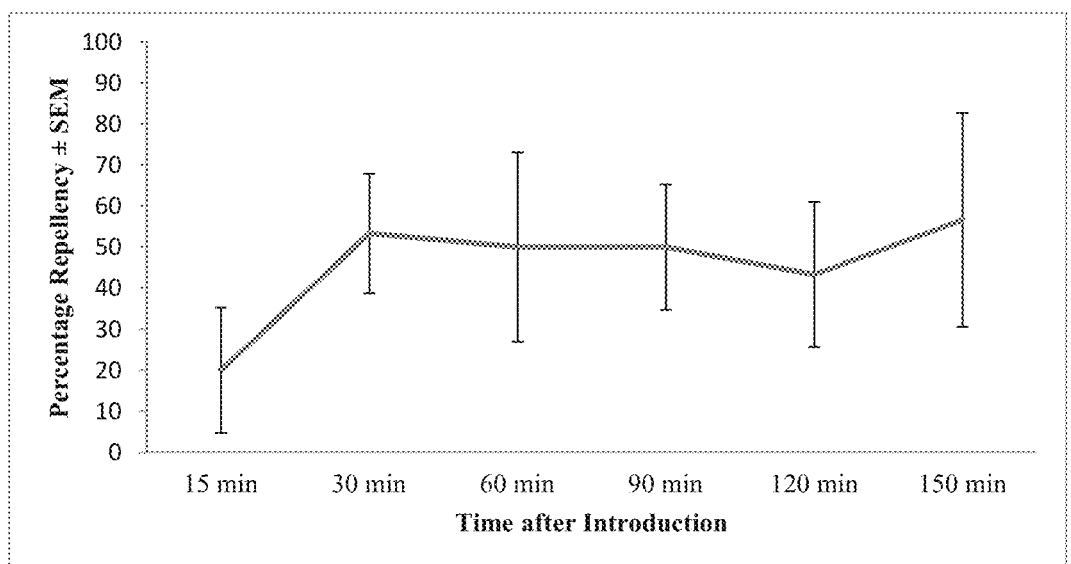
FIG. 2 is a graph showing the short-term percentage repellency of filter papers treated with 1 mL of 0.5% solution in acetone of n-diethyl-meta-toluamide ("DEET") at various time points. This figure demonstrates that DEET, a compound used as a commercial standard for achieving the repellency of various arthropod species, causes percentage repellency in this system.

The mean percentage repellency for each time point caused by the introduction of a filter paper treated with 1 mL of a 0.5% solution of N,N-diethyl-meta-toluaminde (DEET) is illustrated in FIG. 2. The percentage repellency of DEET in this assay at 15 minutes after the introduction of mosquitoes was 20%±15.3. This treatment caused a percentage repellency of 53.3% at 30 minutes after introduction of mosquitoes into the chamber. After this time point, repellency values plateaued with a maximum percentage repellency of approximately 56.7%.

Figure 3:
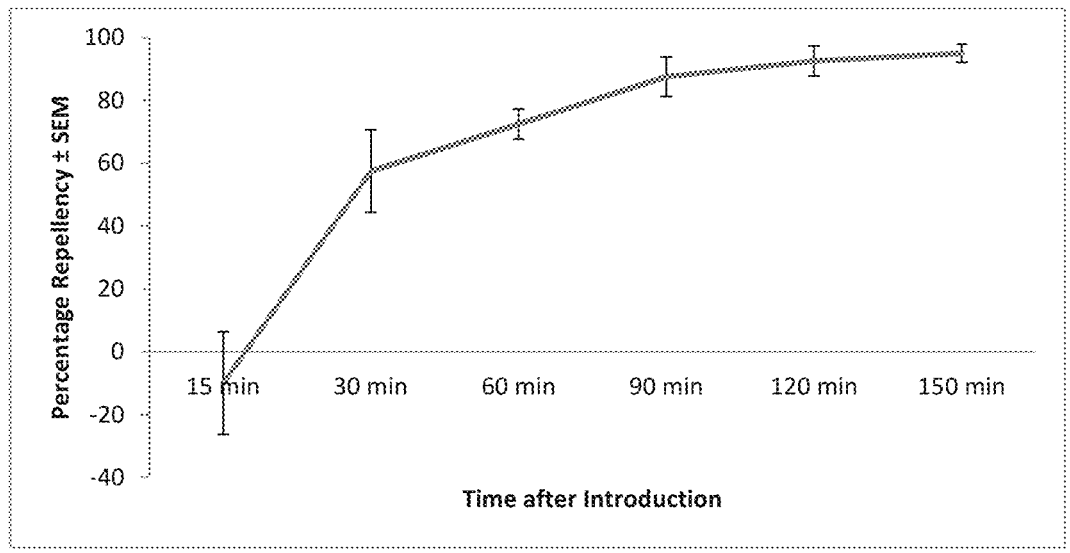
FIG. 3 is a graph showing the short-term percentage repellency of filter papers treated with 1 mL of 0.5% solution in acetone of thymyl cyclopropanecarboxylate at various time points. This figure demonstrates that thymyl cyclopropanecarboxylate is a very effective spatial repellent in this system.
Figure 4:
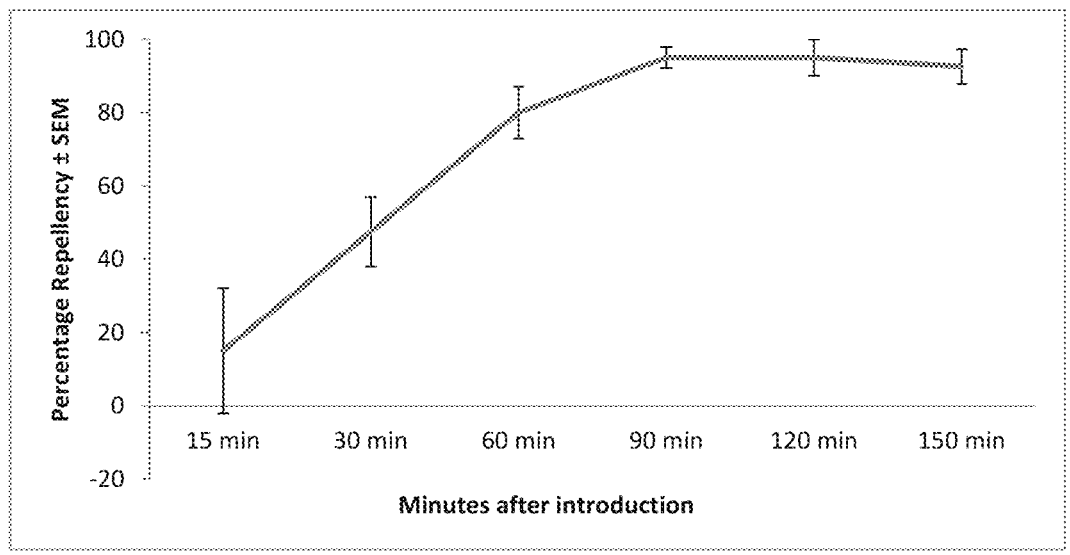
FIG. 4 is a graph showing the short-term percentage repellency of filter papers treated with 1 mL of 0.5% solution in acetone of menthyl cyclopropanecarboxylate at various time points. This figure demonstrates that the menthyl cyclopropanecarboxylate is a very effective spatial repellent in this system.

For the monoterpenoid derivatives of the present invention synthesized and tested, a few representative figures were chosen to demonstrate the behavior of mosquitoes to these compounds in this system. FIG. 3 demonstrates the results for thymyl cyclopropanecarboxylate. Percentage repellency rapidly increased with a percentage repellency of 58% at the 30-minute time point, a value higher than the maximum percentage repellency caused by DEET (56.7%). This percentage repellency continued to increase to 95% at the 150-minute time point. Menthyl cyclopropanecarboxylate was another extremely successful monoterpenoid derivative capable of repelling *Culex* mosquitoes to a high degree. FIG. 4 demonstrates the response of mosquitoes introduced into chambers that contained filter papers treated with this compound. Again, percentage repellency rapidly increased throughout the experimental interval achieving 47.5% and 95% repellency at 30 minutes and 120 minutes after the introduction of mosquitoes, respectively.

Figure 5:
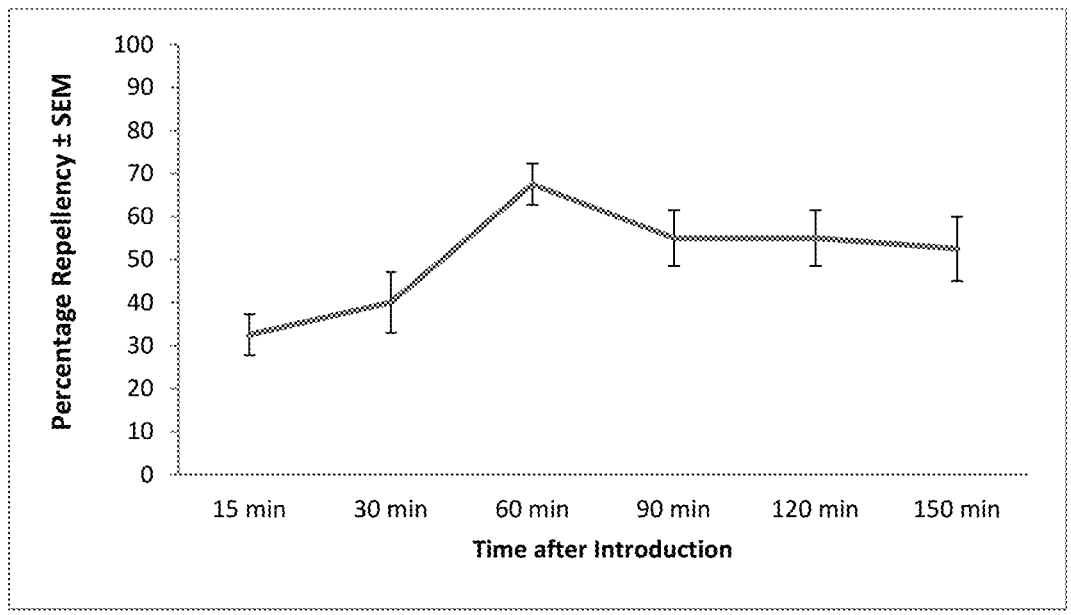
FIG. 5 is a graph showing the short-term percentage repellency of filter papers treated with 1 mL of 0.5% solution in acetone of vanillyl isobutyrate at various time points. This figure demonstrates that the vanillyl isobutyrate causes a different response to both the thymyl cyclopropanecarboxylate and the menthyl cyclopropanecarboxylate.

A range of repellent character was observed for the compounds synthesized. FIG. 5 represents the percentage repellency of vanillyl isobutyrate. Moreover, this range of activity is represented in Table 5, which includes repellency values for many of the compounds tested in the short-term repellency assay at respective time points chosen to highlight the repellent character immediately after introducing the treated filter paper (15-minute time point), in the middle of the testing interval (90-minute time point), and at the end of the testing interval (150-minute time point). Some compounds were capable of causing knockdown (KD), the inability to fly or orient in the upright direction, in this experimental setup. This character of a number of repellent compounds could suggest higher repellency character than is what is detectable in this experimental system at these concentrations and time points. It is possible that these compounds are highly repellent (i.e., more efficacious at lower doses than the other compounds tested) or potentially insecticidal.

TABLE 5

Short-Term Percentage Repellency

| Compound Number | Compound Name | 15 min | 90 min | 150 min |
| --- | --- | --- | --- | --- |
| — | N,N-diethyl-meta-toluamide (DEET) | 20 | 50 | 56.7 |
| — | p-menthane-3,8-diol | 12.5 | 12.5 | 20 |
| 1033B | menthyl cyclopropanecarboxylate | 15 | 95 | 92.5 |
| 2256 | menthyl isovalerate | 37.5 | 42.5 | 27.5 |
| — | citronellol | 32.5 | 80 | 87.5 |
| 1034B | citronellyl isovalerate | 17.5 | 77.5 | 82.5 |
| 1035A | citronellyl cyclopropanecarboxylate | 22.5 | 92.5 | 90 |
| 1036A | citronellyl pivalate | 25 | 90 | 92.5 |
| 1052 | 2-hydroxyethyl citronellate | 77.5 | 92.5 | 82.5 |
| 1089 | citronellyl formate | 77.5 | 92.5 | 90 |
| 1060D | propargyl citronellate | 60 | 72.5 | 70 |
| 1052S3 | 2-hydroxyethyl citronellate | 77.5 | 92.5 | 82.5 |
| 2026 | cyclobutylmethyl citronellate | 25 | 37.5 | 25 |
| 2105 | citronellyl 3,3-dimethylacrylate | 45 | 75 | 65 |
| 2106 | citronellyl 1-methylcyclobutanecarboxylate | 30 | 60 | 67.5 |
| 2119 | citronellyl cyclopentanecarboxylate | -1.25 | 33.75 | 52.5 |
| 2168 | isoprenyl citronellate | 27.5 | 62.5 | 72.5 |
| 2170 | tert-prenyl citronellate | 80 | 92.5 | 82.5 |
| 2171 | 1,1-dimethylpropargyl citronellate | 37.5 | 67.5 | 62.5 |
| 2180 | Citronellyl thiophene-2-carboxylate | 0 | 37.5 | 45 |
| 2183 | citronellyl levulinate | 35 | 45 | 55 |
| 2186 | citronellyl 2-furoate | KD | KD | KD |
| 2189 | citronellyl benzoate | 6.5 | 17.5 | 27.5 |
| 2192 | citronellyl difluoroacetate | 42.5 | 95 | 95 |
| 2198 | citronellyl cyanoacetate | 37.5 | 32.5 | 40 |
| 2203 | citronellyl hexanecarboxylate | 0 | 10 | 20 |
| 2204 | citronellyl isobutyrate | 25 | 80 | 90 |
| 2208 | citronellyl 2-fluoroisobutyrate | 37.5 | 75 | 77.5 |
| 2210 | menthyl 1-methylcyclobutanecarboxylate | -5 | 62.5 | KD |
| 2229 | citronellyl cyclopropylacetate | KD | KD | KD |
| 2232 | citronellyl 2,2-difluoropropanoate | 50 | 82.5 | 82.5 |
| 2235 | citronellyl 3,3,3-trifluoropropanoate | 12.5 | 62.5 | 77.5 |
| 2244 | citronellyl thiophen-2-ylacetate | 32.5 | 45 | 55 |
| 2245 | menthyl thiophen-2-ylacetate | -35 | 35 | 57.5 |
| 3067 | citronellyl 3-oxocyclobutanecarboxylate | 47.5 | 60 | 62.5 |
| 3068 | citronellyl 3-methylcyclobutanecarboxylate | 22.5 | 32.5 | 42.5 |
| 3069 | citronellyl 3,3-difluorocyclobutanecarboxylate | 2.5 | 20 | 27.5 |
| 3070 | (3-methyloxetan-3-yl) methyl citronellate | 15 | 42.5 | 32.5 |
| 3071 | 3-oxetanyl citronellate | 2.5 | 37.5 | 40 |
| 1055B | thymyl isovalerate | 12.5 | 65 | 77.5 |

TABLE 5-continued

Short-Term Percentage Repellency

| Compound Number | Compound Name | 15 min | 90 min | 150 min |
| --- | --- | --- | --- | --- |
| 1055A | thymol cyclopropanecarboxylate | -10 | 87.5 | 95 |
| 1107A | thymyl formate | 35 | 80 | 75 |
| 1077B | thymyl 4-fluorobenzoate | KD | KD | KD |
| 1066B | 4-nitrothymyl cyclopropanecarboxylate | 37.5 | 57.5 | 70 |
| 1075B | 4-bromothymyl cyclopropanecarboxylate | 47.5 | 32.5 | 30 |
| 1121A | thymyl 2-fluoroisobutyrate | 77.5 | 97.5 | 97.5 |
| 1142 | thymyl cyclobutanecarboxylate | KD | KD | KD |
| 1144B | chlorothymyl isobutyrate | 40 | 77.5 | 87.5 |
| 2085 | thymyl cyclohexanecarboxylate | 17.5 | 35 | 50 |
| 2194 | thymyl difluoroacetate | 20 | KD | KD |
| 1076A | eugenyl isovalerate | 17.5 | KD | KD |
| 1149 | eugenyl cyclobutanecarboxylate | KD | KD | KD |
| 1079C | carvacryl isovalerate | -10 | 87.5 | 95 |
| 1107B | carvacryl formate | KD | KD | KD |
| 1121B | carvacryl 2-fluoroisobutyrate | KD | KD | KD |
| 1105 | 2-acetoxyethyl cinnamate | 30 | 15 | 10 |
| 2038 | cinnamyl cyclopropanecarboxylate | 40 | 57.5 | 60 |
| 2039 | cinnamyl cyclobutanecarboxylate | 30 | KD | KD |
| 2003 | vanillyl isobutyrate | 32.5 | 55 | 52.5 |
| 2005 | vanillyl isovalerate | 37.5 | 47.5 | 45 |
| 2023A | geranyl cyclopropanecarboxylate | 45 | 42.5 | 45 |
| 2255A | geranyl isovalerate | 35 | 60 | 52.5 |
| 2020 | cyclopropylmethyl geranate | KD | KD | KD |
| 2023B | neryl cyclopropanecarboxylate | 10 | 52.5 | 60 |
| 2024B | neryl cyclobutanecarboxylate | KD | KD | KD |
| 2108 | neryl 1-methylcyclobutanecarboxylate | 60 | 90 | 85 |
| 2255B | neryl isovalerate | 7.5 | 75 | 80 |
| 2041 | linalyl cyclopropanecarboxylate | KD | KD | KD |
| 2152 | linalyl isovalerate | 15 | 82.5 | 92.5 |
| 2258 | myrteryl isovalerate | 35 | 85 | 87.5 |
| 2257 | alpha-terpinyl isovalerate | 10 | 55 | 65 |
| 2215 | 7-(3-Methylbutanoyloxy)coumarin | KD | KD | KD |

The short-term percentage repellency at 15 minutes, 90 minutes, and 150 minutes after the introduction of filter papers treated with 1 mL of a 0.5% solution in acetone of various monoterpenoid derivatives. A wide range of activity was observed among all the monoterpenoid derivatives tested. A majority of the compounds caused a higher percentage repellency than both DEET and p-menthane-3,8-diol, the active compounds used to achieve repellency in a wide array of commercially available repellent products. Knockdown (KD) was used to indicate the potential of these compounds to cause immobility in mosquitoes tested in this experimental system. This effect could be an indication that these compounds are highly repellent and potentially insecticidal at the concentrations used in this experimental assay.

Figure 6:
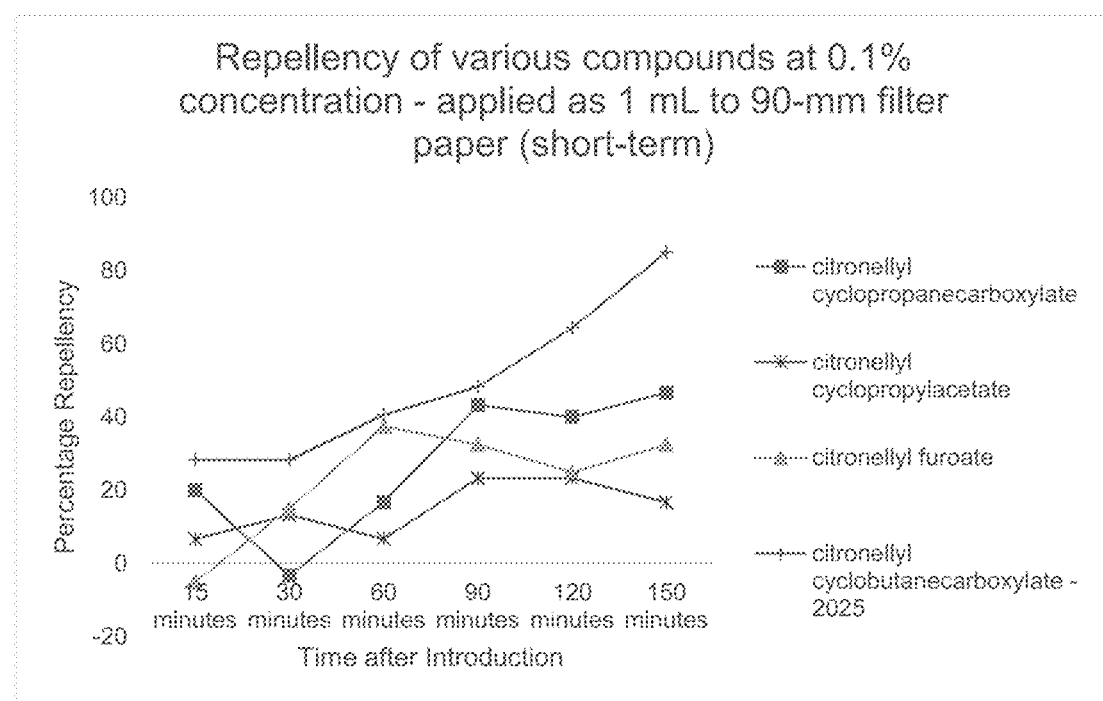
FIG. 6 is a graph showing the short-term percentage repellency of filter paper treated with 0.1% of citronellyl cyclopropanecarboxylate, citronellyl cyclopropylacetate, citronellyl furoate, and citronellyl cyclobutanecarboxylate at various time points. This figure demonstrates that significant levels of repellency were caused by these compounds at low concentrations.

Compounds that were capable of producing knockdown at in the short-term repellency were assumed to be significantly repellent. To further test this hypothesis these select compounds were screened at ⅕ the concentration as applied in the previous exploration. In this experiment, it was observed that significant levels of repellency were caused by these compounds at lower concentrations illustrated in FIG. 6. Citronellyl cyclobutanecarboxylate was capable of producing approximately 90% repellency at 150 minutes. This indicates that this molecule is highly repellent, even at considerably lower levels than explored in previous experiments. Moreover, this data suggests that knockdown corresponds to high levels of repellency rather than simply insecticidal/fumigative character when compounds are applied at the higher 0.5% level.

Example 3—Long-Term Spatial Repellency

Materials and Methods

Mosquitoes

Northern house mosquitoes (*Culex pipiens*), a primary carrier of West Nile virus in eastern North America, were obtained from an established colony in the Medical Entomology Laboratory in the Department of Entomology at Iowa State University of Science and Technology, Ames Iowa. Mosquito rearing was performed by established protocols that are maintained by the Medical Entomology Laboratory. Repellency bioassays were performed with adult female mosquitoes that were 5-7 days post-emergent. After emergence and prior to testing, adult mosquitoes were supplied with a piece of cotton that was soaked in a 10% sucrose solution ad libitum; the mosquitoes tested did not receive a blood meal and were starved for at least 12 hours before testing. Mosquitoes, prior to testing, were held at 27° C., 80% relative humidity, and on a 16:8 hr light:dark photoperiod.

Procedure

Repellency bioassays were performed using a static air repellency chamber, which has been described in various publications by the Pesticide Toxicology Laboratory at Iowa State University of Science and Technology, Ames, Iowa Briefly, a 9-cm×60-cm glass tube was used to monitor the distribution of mosquitoes at 15 min, 30 min, 60 min, 90 min, 120 min, and 150 min after introducing mosquitoes into the static air repellency chamber. Treated filter papers were treated with 1 mL of 0.5% solution in acetone of the terpenoid analogs created in the lab and were exposed to ambient air for 5 hours before they were introduced into the spatial chamber for testing. This is a slight modification of the method described in Example 2, so as to evaluate the residual repellent character of these compounds on a treated surface after 5 hours. One end of the spatial chamber contained a treated filter paper, whereas the other (untreated) end of the spatial chamber was not treated with compound. Controls contained filter papers treated with acetone, the solvent used to make the 0.5% solutions. Each end of the repellency chamber was secured with a 100-mm Petri dish using celluloid tape. After securing the petri dishes with corresponding treated or untreated filter papers to the spatial chamber, mosquitoes were anesthetized with carbon dioxide, and approximately 20 female mosquitoes were placed into each repellency chamber for one replicate. The opening of the spatial repellency chamber was secured with celluloid tape to prevent their escape. Chambers were oriented in opposite directions from the previous replicate to account for any directional effect. Four replicates were performed for data analysis for both the control and treatment groups.

Repellency Data Analysis

Data for spatial repellency, the percentage repellency, is reported at each of the respective time points in the figures and tables mentioned below in this disclosure. The percentage spatial repellency is the examination of the distribution of mosquitoes and is calculated using the following equation:

$$\text{Percentage Repellency} = \frac{(\text{\# of mosquitoes in untreated half}) - (\text{\# of mosquitoes in treated half})}{(\text{total \# of mosquitoes})} \times 100$$

Results

Long-Term Repellency Assay

Figure 7:
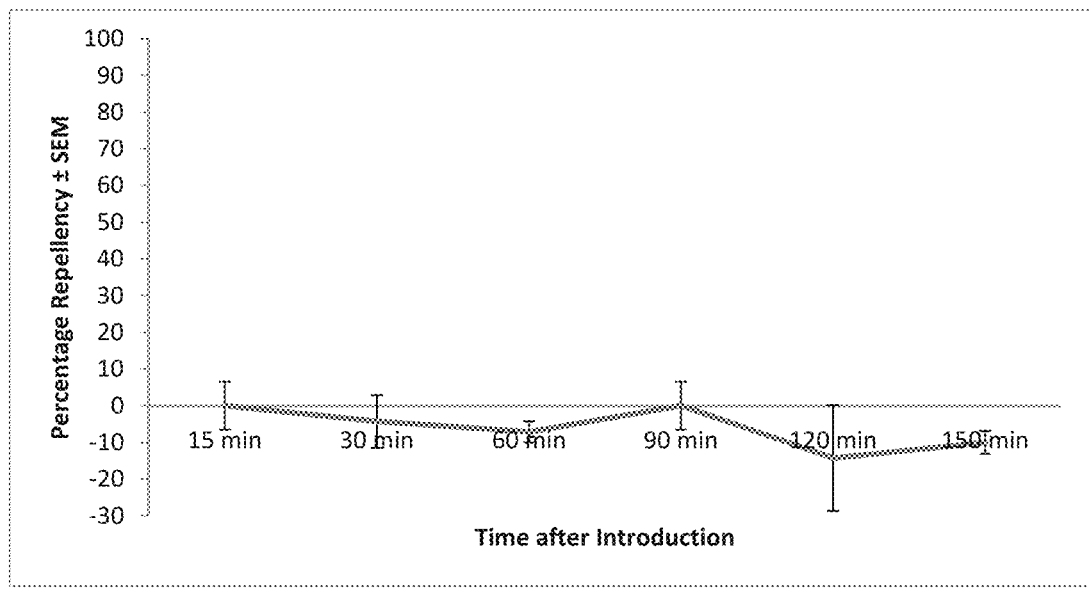
FIG. 7 is a graph showing the long-term percentage repellency of filter papers treated with 1 mL of acetone only at various time points. After treatment, these filter papers were air-dried for 5 hours before introducing them into the static air chamber for testing. This figure demonstrates that the control treatment does not cause any significant repellency after the solvent is allowed to dry for 5 hours before the introduction of the filter papers into the static air chamber.

The mean percentage repellency for each time point caused by the introduction of a filter paper treated with 1 mL of acetone alone (control) and allowed to air-dry for 5 hours is illustrated in FIG. 7. The percentage repellency caused by this treatment is 0% at 15 minutes after the introduction of mosquitoes into the chamber. The absence of statistically significant repellency values for all time points is representative for the solvent control treatment in this experimental system.

Figure 8:
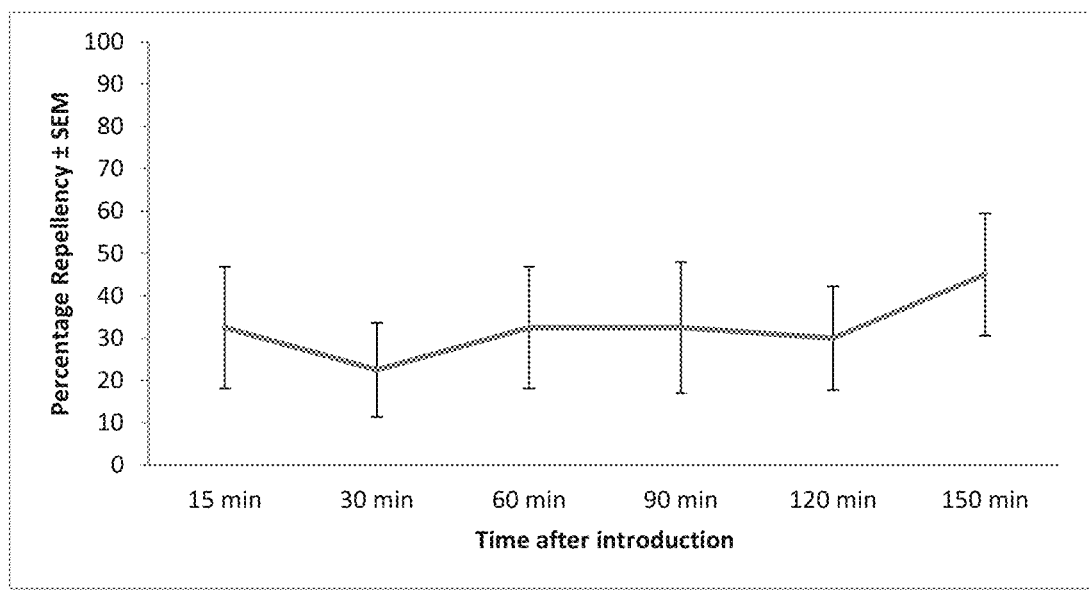
FIG. 8 is a graph showing the long-term percentage repellency of filter papers treated with 1 mL of 0.5% DEET in acetone at various time points. After treatment, these filter papers were air-dried for 5 hours before introducing them into the static air chamber for testing. This figure demonstrates that DEET, a compound used as a commercial standard for achieving the repellency of various arthropod species, causes percentage repellency in this system. This repellency, however, is slightly lower than when tested during the short-term assay described in Example 2 of this disclosure with a maximum percentage repellency of 45%.
Figure 9:
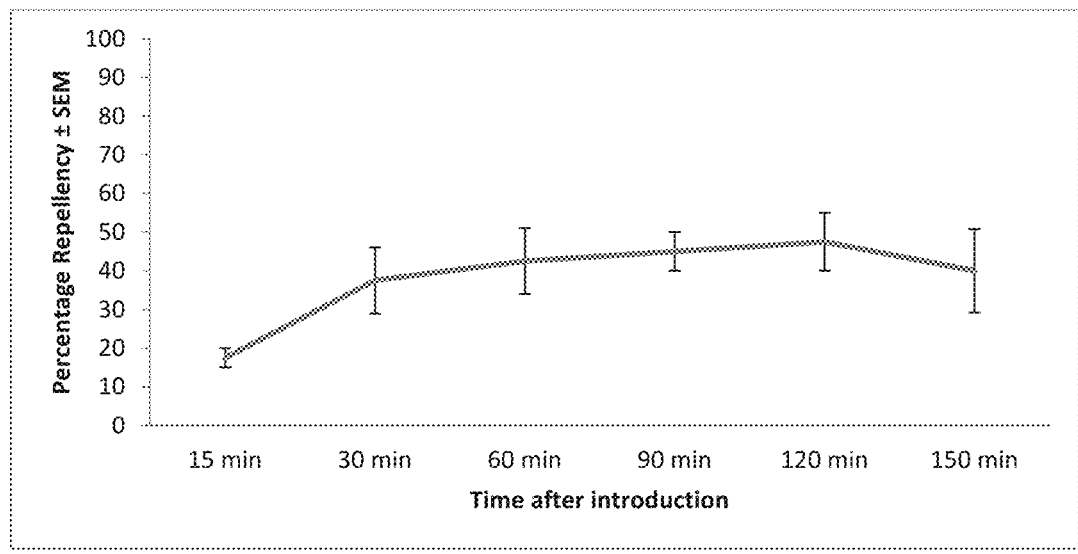
FIG. 9 is a graph showing the long-term percentage repellency of filter papers treated with 1 mL of 0.5% citronella oil (Ceylon) in acetone at various time points. After treatment, these filter papers were air-dried for 5 hours before introducing them into the static air chamber for testing. This figure demonstrates that citronella oil, an essential oil used as a commercial standard for achieving the repellency of various arthropod species, causes percentage repellency in this system. This repellency, however, reaches a maximum of approximately 47.5%.

The mean percentage repellency for each time point caused by the introduction of a filter paper treated with 1 mL of a 0.5% solution of N,N-diethyl-meta-toluaminde (DEET) and air-dried for 5 hours is illustrated in FIG. 8. The percentage repellency of DEET in this assay at 15 minutes after the introduction of mosquitoes was 32.5%±14.4. This treatment caused a percentage repellency of 22.5% at 30 minutes after introduction of mosquitoes into the chamber. After this time point, repellency values plateaued with a maximum percentage repellency of approximately 45%. In comparison the mean percentage repellency for each time point caused by the introduction of a filter paper treated with 1 mL of 0.5% citronella oil (Ceylon) in acetone and air-dried for 5 hours is illustrated in FIG. 9. The percentage repellency of citronella oil in this assay reaches a maximum of approximately 47.5%.

Figure 10:
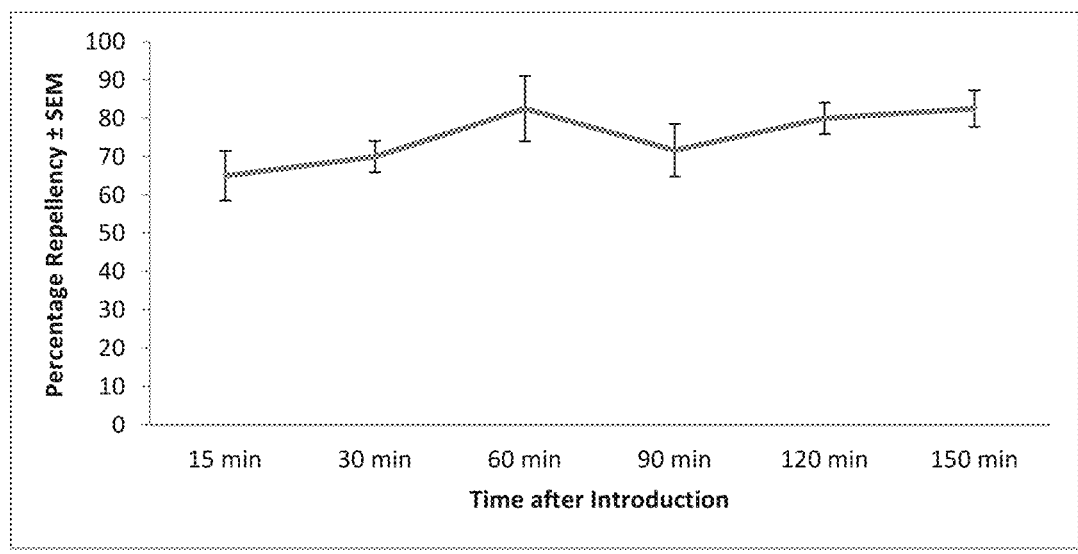
FIG. 10 is a graph showing the long-term percentage repellency of filter papers treated with 1 mL of 0.5% menthyl cyclopropanecarboxylate in acetone at various time points. After treatment, these filter papers were air-dried for 5 hours before introducing them into the static air chamber for testing. This figure demonstrates that menthyl cyclopropanecarboxylate causes percentage repellency in this system that is much greater than DEET after filter papers are allowed to air-dry for 5 hours.
Figure 11:
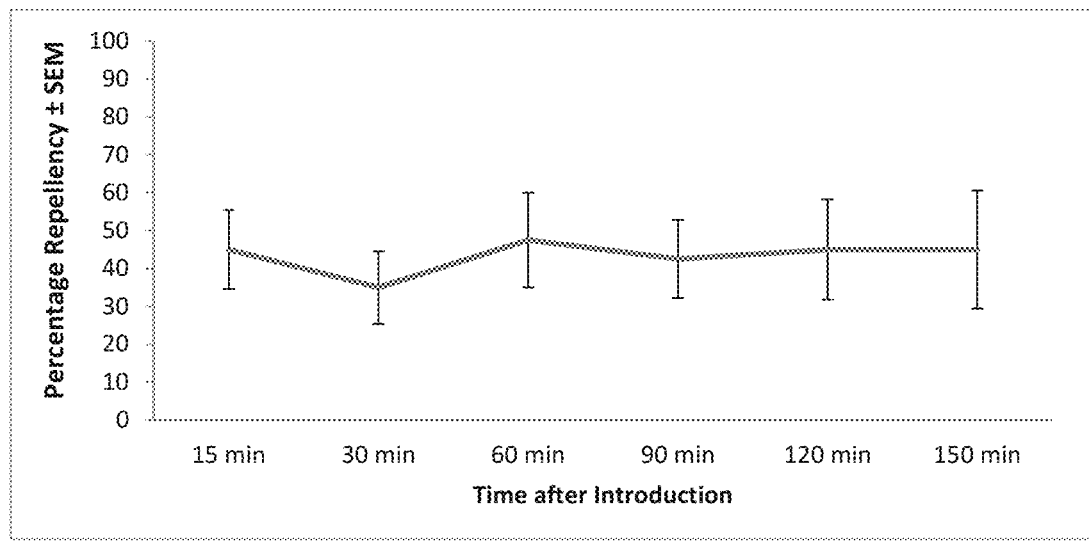
FIG. 11 is a graph showing the long-term percentage repellency of filter papers treated with 1 mL of 0.5% geranyl cyclopropanecarboxylate in acetone at various time points. After treatment, these filter papers were air-dried for 5 hours before introducing them into the static air chamber for testing. This figure demonstrates that geranyl cyclopropanecarboxylate causes percentage repellency in this system that is much greater than DEET after filter papers are allowed to air-dry for 5 hours.

For the monoterpenoid derivatives of the present invention synthesized and tested, a few representative figures were chosen to demonstrate the behavior of mosquitoes to these compounds in this system. FIG. 10 demonstrates the results for menthyl cyclopropanecarboxylate. Percentage repellency rapidly increased with a percentage repellency of 65% at 15 minutes, a value higher than the maximum percentage repellency caused by DEET (45%). This percentage repellency continued to increase to 82.5% at the 150-minute time point. Geranyl cyclopropanecarboxylate was another successful monoterpenoid derivative capable of repelling *Culex* mosquitoes to a high degree. FIG. 11 demonstrates the response of mosquitoes introduced into chambers that contained filter papers treated with this compound. Again, percentage repellency rapidly increased throughout the experimental interval achieving 45% and 47.5% repellency at 15 minutes and 60 minutes after the introduction of mosquitoes, respectively.

Figure 12:
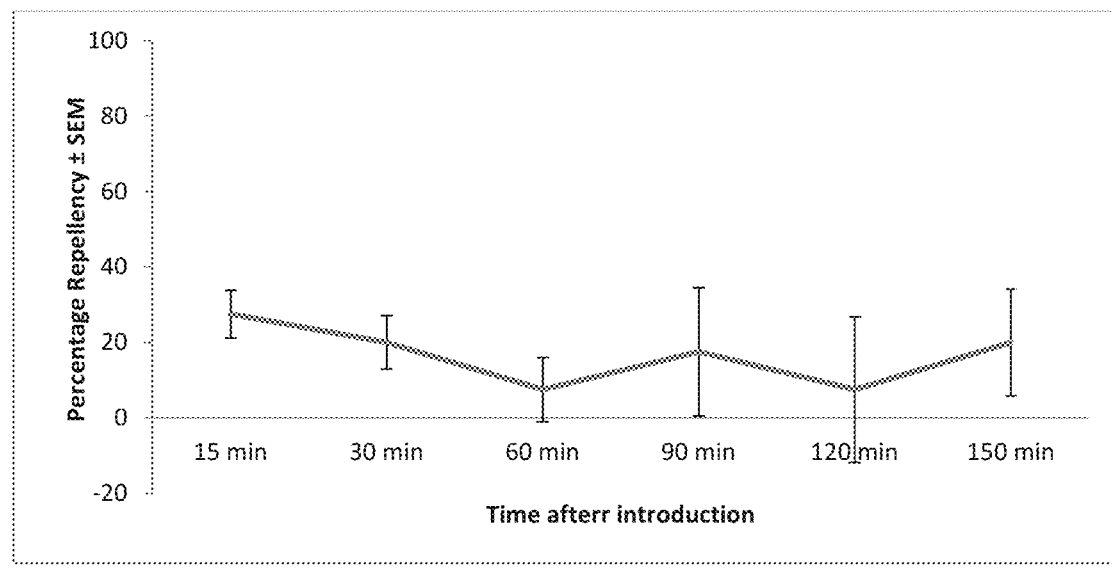
FIG. 12 is a graph showing the long-term percentage repellency of filter papers treated with 1 mL of 0.5% citronellyl pivalate in acetone at various time points. After treatment, these filter papers were air-dried for 5 hours before introducing them into the static air chamber for testing. This figure demonstrates that citronellyl pivalate causes percentage repellency in this system but with a different repellency character than the other compounds.

A range of repellent character was observed for the compounds synthesized. FIG. 12 represents the percentage repellency of citronellyl pivalate over the testing interval. Moreover, this range of activity is represented in Table 6, which includes repellency values for many of the compounds tested in the short-term repellency assay at respective time points chosen to highlight the repellent character immediately after introducing the treated filter paper (15-minute time point), in the middle of the testing interval (90-minute time point), and at the end of the testing interval (150-minute time point). Some compounds were capable of causing knockdown (KD), the inability to fly or orient in the upright direction, in this experimental setup. This character of a number of repellent compounds could suggest higher repellency character than what is detectable in this experimental system at these concentrations and time points. It is possible that these compounds are highly repellent (i.e., more efficacious at lower doses than the other compounds tested) or potentially insecticidal.

TABLE 6

Long-Term Percentage Repellency

| Compound Number | Compound Name | Long-term Percentage repellency | | |
|---|---|---|---|---|
| | | 15 min | 90 min | 150 min |
| — | N,N-diethyl-meta-toluamide (DEET) | 32.5 | 32.5 | 45 |
| — | p-menthane-3,8-diol | 7.5 | 5 | 5 |
| 1033B | menthyl cyclopropanecarboxylate | 65 | 71.7 | 82.5 |
| — | citronellol | 30 | 25 | 25 |
| 1034B | citronellyl isovalerate | 30 | 30 | 32.5 |
| 1035A | citronellyl cyclopropanecarboxylate | 70 | 80 | 62.5 |
| 1036A | citronellyl pivalate | 27.5 | 17.5 | 20 |
| 2119 | citronellyl cyclopentanecarboxylate | 20 | 55 | 45 |
| 2106 | citronellyl 1-methylcyclobutanecarboxylate | 15 | 10 | 15 |
| 1060D | propargyl citronellate | 15 | 62.5 | 77.5 |
| 1052S3 | 2-hydroxyethyl citronellate | 37.5 | 65 | 75 |
| 2170 | tert-prenyl citronellate | 2.5 | 7.5 | -2.5 |
| 2144 | 2-hydroxypropyl citronellate | 12.5 | 20 | 35 |
| 2183 | citronellyl levulinate | 35 | 45 | 55 |
| 2186 | citronellyl 2-furoate | 25 | 42.5 | 40 |
| 2192 | citronellyl difluoroacetate | 50 | 72.5 | 65 |
| 2204 | citronellyl isobutyrate | -5 | 7.5 | 10 |
| 3067 | citronellyl 3-oxocyclobutanecarboxylate | 12.5 | 0 | 25 |
| 3068 | citronellyl 3-methylcyclobutanecarboxylate | 22.5 | 32.5 | 42.5 |
| 1055B | thymyl isovalerate | 0 | 22.5 | 27.5 |
| 1055A | thymol cyclopropanecarboxylate | 0 | 32.5 | 52.5 |
| 1077B | thymyl 4-fluorobenzoate | KD | KD | KD |
| 1107A | thymyl formate | 25 | 17.5 | 22.5 |
| 1121A | thymyl 2-fluoroisobutyrate | 22.5 | 50 | 65 |
| 1142 | thymyl cyclobutanecarboxylate | KD | KD | KD |
| 2085 | thymyl cyclohexanecarboxylate | 17.5 | 35 | 50 |
| 1107B | carvacryl formate | 30 | 37.5 | 42.5 |
| 2020 | cyclopropylmethyl geranate | 40 | 45 | 40 |
| 2023A | geranyl cyclopropanecarboxylate | 45 | 42.5 | 45 |
| 2023B | neryl cyclopropanecarboxylate | 10 | 52.5 | 60 |
| 2033 | perillyl cyclobutanecarboxylate | 27.5 | KD | KD |
| 2039 | cinnamyl cyclopropanecarboxylate | 40 | 57.5 | 60 |

The long-term percentage repellency at 15 minutes, 90 minutes, and 150 minutes after the introduction of filter papers treated with 1 mL of a 0.5% solution in acetone of various monoterpenoid derivatives. These filter papers were air-dried for 5 hours before introducing them into the repellency experiment setup. A wide range of activity was observed among all the monoterpenoid derivatives tested. A number of the compounds caused higher percentage repellency values than both DEET and p-menthane-3,8-diol, the active compounds used to achieve repellency in a wide array of commercially available repellent products. Knockdown (KD) was used to indicate the potential of these compounds to cause immobility in mosquitoes tested in this experimental system. This effect could be an indication that these compounds are highly repellent and potentially insecticidal at the concentrations used in this experimental assay.

Example 4—Contact Irritancy Assay

Materials and Methods

Mosquitoes

Northern house mosquitoes (*Culex pipiens*), a primary carrier of West Nile virus in eastern North America, were obtained from an established colony in the Medical Entomology Laboratory in the Department of Entomology at Iowa State University of Science and Technology, Ames Iowa. Mosquito rearing was performed by established protocols that are maintained by the Medical Entomology Laboratory. Repellency bioassays were performed with adult female mosquitoes that were 5-7 days post-emergent. After emergence and prior to testing, adult mosquitoes were supplied with a piece of cotton that was soaked in a 10% sucrose solution ad libitum; the mosquitoes tested did not receive a blood meal and were starved for at least 12 hours before testing. Mosquitoes, prior to testing, were held at 27° C., 80% relative humidity, and on a 16:8 hr light:dark photoperiod.

Procedure

Figure 13:
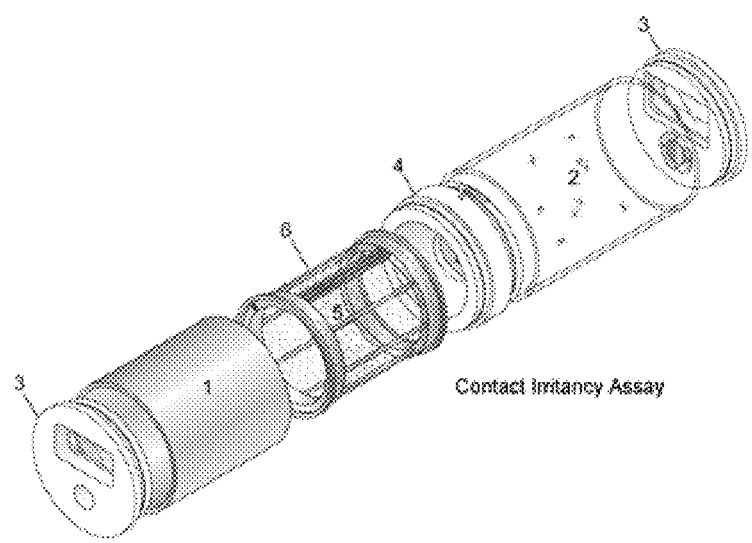
FIG. 13 is a schematic illustration showing an experimental device used to evaluate the efficacy of the compounds of the present invention to illicit contact irritancy.

Organza were cut to approximately 11.5 cm×8 cm to wrap around the inside of the contact irritancy chamber. This piece of organza was treated with 1.5 mL of 0.5% or 0.05% solution of test compound in acetone. This organza was allowed to air-dry for 15 minutes before introducing them into the chamber. Organza sheets were draped around the inside wall of the metallic chamber and fastened to the walls of the chamber with small magnets. Ten adult, unfed female mosquitoes were mouth aspirated and placed into the metallic half of the contact irritancy chamber as described by Greico et al., "A New Classification System for the Actions of IRS Chemicals Traditionally Used for Malaria Control," *PLoS ONE* (2007), which is hereby incorporated by reference in its entirety. The butterfly valve in the center of the repellency chamber was closed at this point to prevent the escape of mosquitoes into the clear "counting" chamber. After mosquitoes were allowed to acclimate to the containers for 30 seconds, the butterfly valves were opened for 10 minutes. This allowed mosquitoes to freely move between the chambers. After ten minutes, the butterfly valve was once again closed and the number of mosquitoes was counted in the clear "counting" chamber. This allowed for the evaluation of the irritancy of the compound toward adult female mosquitoes. For compounds that cause a high level of contact irritancy, more mosquitoes will migrate into the untreated clear "counting" chamber. Six replicates were completed for each treatment. Control treatments of solvent only were run alongside treatments every day in which testing occurred. Control mosquito escape values were pooled across multiple days and represent greater than 50 replicates. FIG. 13 is a schematic illustration representing the experimental device used to evaluate the efficacy of these compounds to illicit contact irritancy.

Repellency Data Analysis

The number of mosquitoes that escaped into the clear "counting" chamber was enumerated for each replicate. The number of escaping mosquitoes for each replicate was converted into a total percent escape number. Data was averaged across multiple replicates and presented with the standard error of the mean.

Results and Discussion

Figure 14:
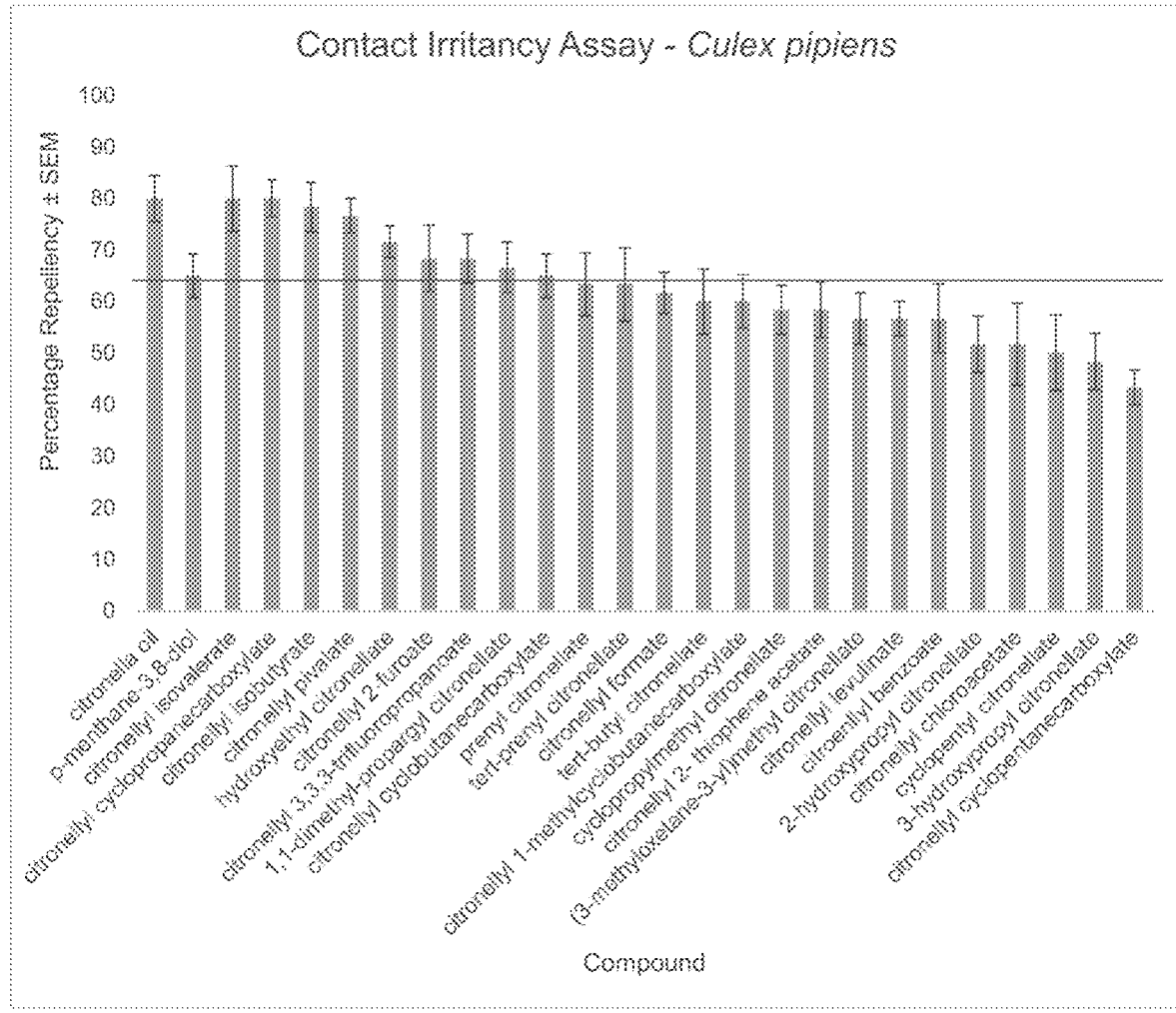
FIG. 14 is a graph showing the ability of selected monoterpenoid derivative compounds to cause contact irritancy, which could be an indication of contact repellency. The contact irritancy caused by most of the monoterpenoid derivative compounds of the present invention was higher than that of p-menthane-3,8-diol, a common active ingredient found in many commercially available repellents.

The average contact irritancy as evaluated by the percent escape of mosquitoes from the treated chamber was recorded for each of the compounds tested (FIG. 14). Many of the compounds tested caused a high level of contact irritancy in this particular assay when applied to organza netting as 1 mL of a 0.5% solution. After letting the solvent dry for approximately 10 minutes, these nets were introduced into the chamber with magnets used to ensure that they lined the walls of the exposure chamber. A majority of the monoterpenoid derivatives caused a higher percent escape than p-menthane-3,8-diol, which caused a percentage escape of approximately 65%. Moreover, the most successful repellent compounds performed similarly to citronella oil, which caused a percentage escape of 80%. The most successful monoterpenoid esters, citronellyl cyclopropanecarboxylate and citronelly cyclopropanecarboxylate, caused 80% escape in this assay as well. This data indicates that compounds of the present invention are capable of causing potent contact irritancy, a characteristic of the most successful commercial repellents.

Example 5—Human Skin Testing, Biting Deterrence

Materials and Methods

Mosquitoes

Female mosquitoes (*Aedes aegypti*) were reared according to the standard protocol at a temperature of 27.5±1° C., a relative humidity of 65-80% and a 12:12 hour photo period. The light period (450 Lux) was set from 7:00 to 19:00. After hatching from the eggs, larvae were kept in a water basin (30×30×10 cm) filled with a 1:1 mixture of tap- and deionized water with low oxygen content and fed with fish food flakes (Tetra Min®). Pupae were transferred to a cage (40×30×20 cm) provided with sugar solution (10% dextrose). Mosquitoes at an age of 5 to 10 days post-emergence were used for behavioral tests.

BioGents Test Cages

BioGents (BG) test cages are an in-house improvement of conventional test cages for the evaluation of mosquito repellents (Obermayr et al., "A Novel Test Cage with an Air Ventilation System as an Alternative to Conventional Cages for the Efficacy Testing of Mosquito Repellents," *J. Med. Entomol.* 47:1116-22 (2010) which is hereby incorporated by reference in its entirety). The cages have a volume of 27.000 cm$^3$ (41×41×16 cm). Four sides of a cage are made of acrylic glass, the floor is made of metal sheet, and the rear side is covered by a gauze sleeve. The floor sheet is equipped with a test window (size: 56 cm$^2$; 14.8×3.8 cm) for the exposure of the treated skin. In between tests, BG cages are connected to a ventilation system that provides clean, warm, and humid air (26±1° C., 65±5% R.H.) to remove remaining host odours and repellent volatiles from the air inside the cage. In the presented study, the ventilation system was not applied as mosquitoes were only tested once and then discarded. Each treated sleeve was tested on a fresh batch of mosquitoes. Each cage was filled with populations of 30 mosquitoes, lured out of their rearing cages by a natural stimulus (human hand) to ensure that only host-seeking females are used for the repellent tests Procedure All formulations have been stored at 4° C. Prior to testing, stock formulations were diluted v/v to final concentrations of 10% in 200 proof ethanol. Nylon stockings were cut into pieces of comparable size that could be worn on the lower arm like a sleeve. For each test formulations, 2 pieces were prepared—one was treated, while the other one remained untreated and was worn between skin and treated nylon sleeve.

From each test formulation 5 ml were filled into 25 ml glass flasks; immediately afterwards stockings were folded into the flasks and pushed into the liquid formulation with a clean spatula. Flasks were sealed and incubated in the fridge overnight. On the consecutive day, one of the treated nylon pieces was removed from the flasks and left to dry on a clean paper towel for at least 10 minutes or until the ethanol had evaporated. The drying process was conducted at 27° C. and 65% to 80%. One untreated nylon sleeve was attached to the forearm followed by the treated sleeve.

Prior to a repellent efficacy test, the biting activity of the test mosquitoes was verified with the other, untreated forearm of a volunteer (wearing an untreated nylon sleeve). To keep biting pressure on the untreated skin low, a modified spacer covered with fine mosquito netting was used in control tests. Mosquitoes were still attracted to the skin odours and landed on the net, however they were not able to reach the skin and pierce it. A minimum of 10 landings had to be observed in 30 seconds during tests with *Ae. aegypti*. In case of lowered biting activities, 5 to 10 new mosquitoes were added to the cage or 30 new mosquitoes are used. Mosquitoes were allowed to recover from control tests for 5 minutes. One of the treated sleeves was exposed at the test window for a maximum testing time of 2 minutes. The number of landing and biting mosquitoes was recorded. Tests were stopped with the occurrence of the FCB (first confirmed bite, one bite followed by another one). Efficacy tests were conducted with one volunteer (female, 40 years).

Results and Discussion

Repellent effects were clearly noticeable in tests of both 2-hydroxyethyl citronellate and 2-hydroxypropyl citronellate, represented in Table 7. Mosquitoes that landed on the treated nylon surfaces usually took off again quickly or just walked across the surface for a few seconds. In tests of 2-hydroxyethyl citronellate one bite occurred. However, the mosquito did not complete the blood meal and removed its proboscis after about 20 seconds. Some mosquitoes cleaned their proboscis after having made contact with the treated nylon surfaces. The 2-hydroxyethyl citronellate and 2-hydroxypropyl citronellate at a concentration of 10% look very promising as potential repellent compounds.

TABLE 7

Biting Responses of *Aedes aegypti* Exposed to Human Arm in Cage Covered with Treated or Untreated Nylon Stocking

| | Contacts | | | |
| --- | --- | --- | --- | --- |
| Sample | Short touch-down | Landing (mosquitoes sits for >3 sec) | Bites | Observations |
| Untreated Nylon (Control) | 0 | 13 | 10/29 sec | |
| Nylon treated with 10% 2-hydroxyethyl citronellate | 12 | 3 | 1/120 sec (98% bite reduction) | Visible repelient effects (quick take off, cleaning behavior) |
| Nylon treated with 10% 2-hydroxypropyl citronellate | 18 | 2 | 0/120 sec (100% bite reduction) | Visible repelient effects (quick take off, cleaning behavior) |

Example 6—Minimum Effective Dosage Testing, Human Skin

Materials and Methods

Mosquitoes

The test mosquitoes were female *Aedes aegypti* (Orlando strain, 1952) from the colony maintained at United States Department of Agriculture-Agricultural Research Service-Center for Medical, Agricultural and Veterinary Entomology (USDA-ARS-CMAVE) in Gainesville, Fla. Pupae were obtained from the colony and newly emerged mosquitoes were maintained on 10% sugar water and kept in laboratory cages at an ambient temperature of 28±1° C. and RH of 35-60%. Host seeking behavior was pre-selected in nulliparous female mosquitoes aged 6-10 days, indicated by flight upwind towards a potential host, from stock cages using a hand-draw box and trapped in a collection trap.

Procedure

After 500 (±10%) females were collected in the trap, they were transferred to a test cage (approximately 59,000 $cm^3$ with dimensions 45×37.5×35 cm) and allowed to acclimatize for 17.5 (±2.5) min before testing was initiated. Just prior to the experiment, the pieces of treated cloth are removed from the vials and stapled onto card stock tabs (5×3 cm). Each piece of the cards and the assembly were hung on a drying rack using masking tape for 3-5 min. Participants in the study used latex gloves to pull a nylon stocking over their arm. A Velcro™-sealed vinyl sleeve was then placed over the forearm. The sleeve had a 32-$cm^2$ (4×8 cm) window to allow attractive skin odors to escape and draw mosquitoes to that open area. The purpose of the nylon stocking was to produce a barrier between the dried cloth and the skin, thereby avoiding direct contact of chemical to skin. The dried cloth assembly was affixed over the opening in the sleeve and held in place with masking tape. Participants then inserted their arm with the sleeve and patch into a screened cage that contained female *Ae. Aegypti* mosquitoes. Tests were conducted on each control or treated patch for 1 min. A control patch (acetone solvent only, then dried) was tested prior to the start of experiments and evaluation of the same untreated control patch after every 10 tests. If 5 landings were not received on the control patch in 30 s, then tests were discontinued for 60 min. At the conclusion of testing the control patch was tested again. If five landings were not received within 30 s, the data for the replicate was discarded. When testing a patch treated with a candidate repellent, if approximately 1% or 5 mosquito bites were received during this one minute test, this compound was considered to have failed, i.e., was not repellent at that concentration. If a treated cloth patch received 0-4 bites within a minute, then it was considered as passed, i.e., repellent at that concentration of the test compound. The median concentration patch was tested in the first round and treated patches were then tested successively at higher or lower concentrations depending upon whether the previous patch failed or passed, respectively.

The time interval between each tested patch was <90 seconds until 10 successive tests had been conducted. If appreciable, mortality had occurred during testing, the number of knocked down mosquitoes are estimated and additional female mosquitoes are added to the cage to keep the available mosquitoes at approximately 500. The estimate of the MED was the lowest concentration that passed for each candidate. Observed MED values for each candidate compound were averaged across participants and reported as a mean MED±standard error.

Results and Discussion

Numerous compounds were screened against *Aedes aegypti* to determine their minimum effective dosage when applied to nylon stockings. The minimum effective dosage corresponds to amount of each compound that is required to prevent 1% of mosquitoes from landing and biting within a one-minute interval. Of the compounds screened, all but one were capable of producing repellent effects at a discrete dosage as indicated in Table 8. Of the various compounds screened, the citronellates and geranates were the most efficacious. Of the various compounds screened, two compounds caused repellency at levels that were statistically equivalent to DEET. 2-hydroxyethyl citronellate and 2-hydroxypropyl citronellate were capable of repelling mosquitoes at 0.039 and 0.055 $mg/cm^3$, respectively. When taking into account the variability among subjects and between compounds, these compounds performed similarly to DEET, despite having numerically higher minimum effective dosage values.

TABLE 8

*Aedes aegypti* Minimum Effective Dosage ($mg/cm^2$)

| | Subject 1 | Subject 2 | Subject 3 | Average | Std. Dev. | Std. Error | High Dose ($mg/cm^2$) | Proportion to DEET |
|---|---|---|---|---|---|---|---|---|
| 2-hydroxyethyl geranate | 0.187 | 0.375 | 0.187 | 0.250 | 0.109 | 0.063 | 1.5 | 13.140 |
| 2-hydroxypropyl cinnamate | n/a | 0.375 | 0.375 | 0.375 | 0.000 | 0.000 | 1.5 | 19.737 |
| 3-hydroxypropyl cinnamate | 0.750 | 1.500 | 0.750 | 1.000 | 0.433 | 0.250 | 1.5 | 52.632 |
| 2-hydroxypropyl geranate | 0.047 | 0.047 | 0.047 | 0.047 | 0.000 | 0.000 | 1.5 | 2.474 |
| 3-hydroxypropyl geranate | 0.187 | 0.094 | 0.094 | 0.125 | 0.054 | 0.031 | 1.5 | 6.579 |
| 2-hydroxypropyl citronellate | 0.047 | 0.047 | 0.023 | 0.039 | 0.014 | 0.008 | 1.5 | 2.053 |
| 3-hydroxypropyl citronellate | 0.094 | 0.094 | 0.023 | 0.070 | 0.041 | 0.024 | 1.5 | 3.702 |
| 2-hydroxyethyl citronellate | 0.023 | 0.094 | 0.047 | 0.055 | 0.036 | 0.021 | 1.5 | 2.877 |
| 2-hydroxyethyl cinnamate | n/a | n/a | 0.094 | | | | 1.5 | 0.000 |
| DEET | 0.023 | 0.023 | 0.011 | 0.019 | 0.007 | 0.004 | 1.5 | 1.000 | n/a = compound ineffective at highest available dose

Conclusions (Examples 2-6)

The compounds of the present invention synthesized and tested here are highly successful at repelling mosquitoes. A majority of these compounds caused a higher percentage repellency than both DEET and p-menthane-3,8-diol in this testing, both of which are used as the standard active ingredients in the most successful arthropod repellency products available on the market. Because of the greater efficacy of many of these compounds than both DEET and p-menthane-3,8-diol at the same application rate of 1 mL of a 0.5% solution in acetone in this experimental system, it is possible that these compounds could achieve similar or greater levels of repellency than both DEET and p-menthane-3,8-diol at even lower amounts used in current commercial products. Just as DEET and p-menthane-3,-8-diol are capable of repelling a variety of pest arthropod species, these compounds could potentially repel a variety of important pest arthropod species in the agricultural, urban, veterinary, and public health arenas.

Although some embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound of formula (A) as follows:

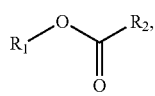
(A)

wherein
R$_1$ is a monoterpenoid moiety selected from the group consisting of

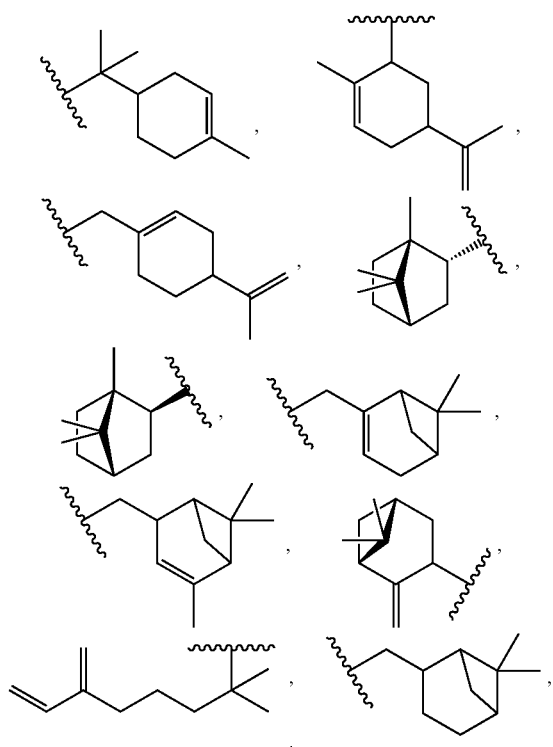

and

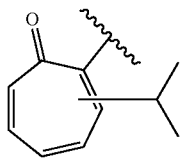

or phenylpropanoid moiety selected from the group consisting of

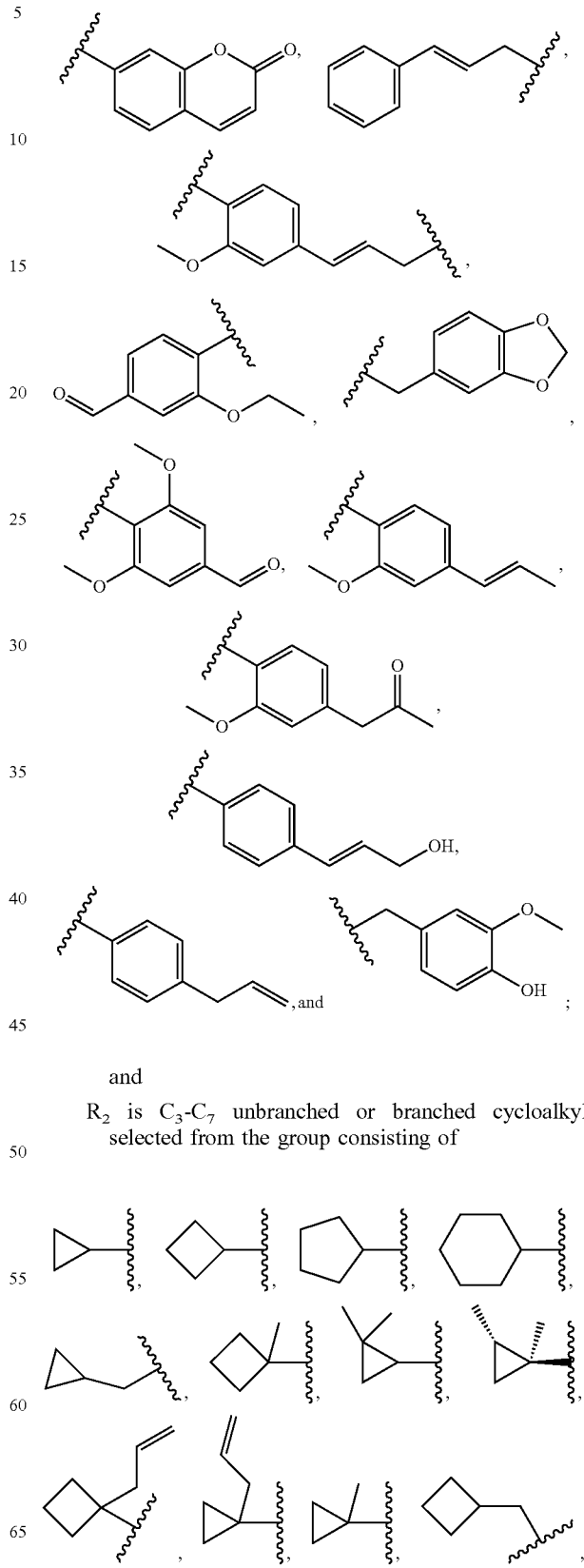

and

R$_2$ is C$_3$-C$_7$ unbranched or branched cycloalkyl selected from the group consisting of

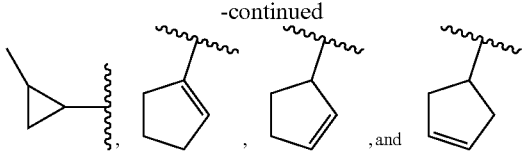

2. The compound of claim 1, wherein $R_1$ is a monoterpenoid moiety.

3. The compound of claim 1, wherein $R_1$ is a phenylpropanoid moiety.

4. The compound of claim 1, wherein the compound is selected from the group consisting of: myrtenyl cyclopropanecarboxylate, perillyl cyclopropanecarboxylate, perillyl cyclobutanecarboxylate, cinnamyl cyclopropanecarboxylate, cinnamyl cyclobutanecarboxylate, α-terpinyl cyclopropanecarboxylate, α-terpinyl cyclobutanecarboxylate, perillyl cyclohexanecarboxylate, perillyl cyclopentanecarboxylate, bornyl cyclopropanecarboxylate, bornyl cyclobutanecarboxylate, isobornyl cyclopropanecarboxylate, isobornyl cyclobutanecarboxylate, myrtenyl cyclobutanecarboxylate, 7-(cyclopropanecarboxoyloxy)coumarin, 7-(cyclobutanecarboxoyloxy)coumarin, 7-(cyclopentanecarboxoyloxy)coumarin, carvyl cyclopropanecarboxylate, carvyl cyclobutanecarboxylate, and carvyl cyclopentanecarboxylate.

5. A composition comprising:

a carrier and (i) a compound of formula (A) as follows:

$$R_1\text{—O—C(=O)—}R_2 \quad (A)$$

wherein $R_1$ is a monoterpenoid moiety selected from the group consisting of

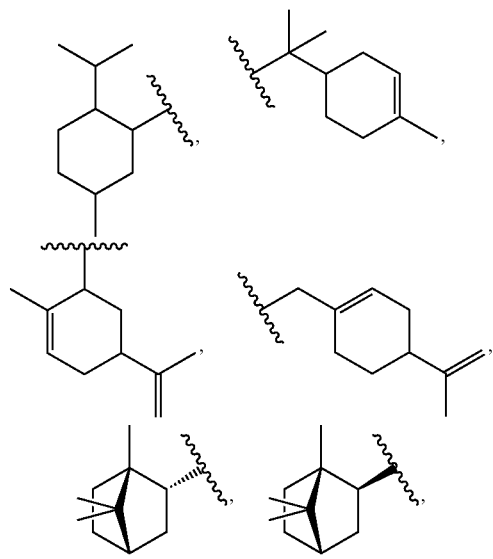

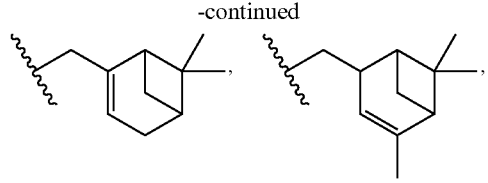

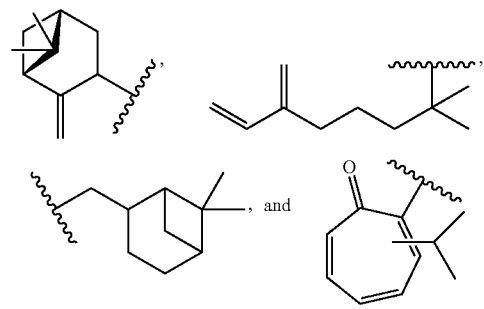

or phenylpropanoid moiety selected from the group consisting of

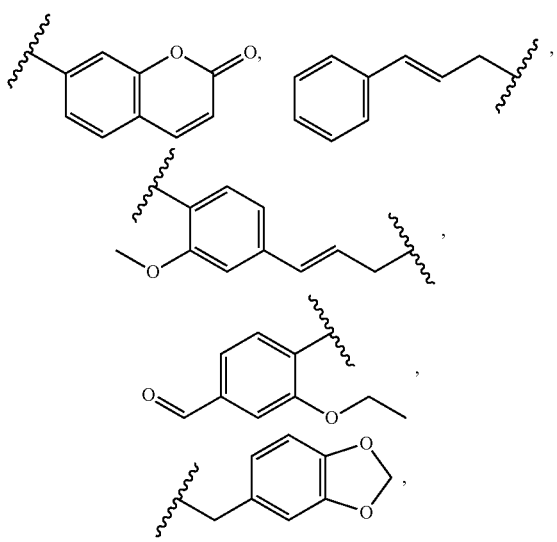

$R_2$ is $C_3$-$C_7$ unbranched or branched cycloalkyl, selected from the group consisting of

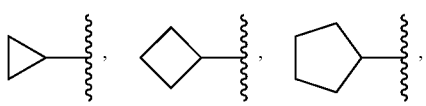

-continued

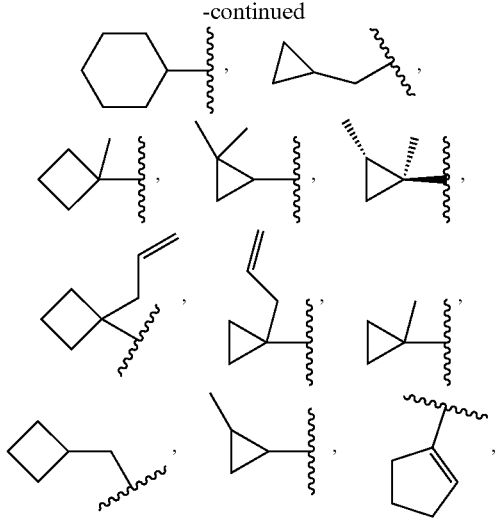

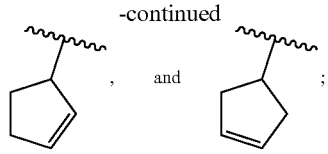

wherein the composition is in the form of a lotion, spray, or cream.

6. The composition of claim 5, wherein the compound is a single enantiomer or diastereomer.

7. The composition of claim 5, wherein the compound is in a racemic or diastereomeric mixture.

8. The composition of claim 5, wherein the carrier is selected from a solid, liquid, and gas.

9. The composition of claim 5 further comprising:

a fragrance, perfume, or cologne.

* * * * *